United States Patent
Schwartz et al.

(10) Patent No.: US 9,937,154 B2
(45) Date of Patent: Apr. 10, 2018

(54) USE OF TELMISARTAN TO PREVENT AND TREAT GRAFT VERSUS HOST DISEASE AND OTHER ALLOIMMUNE AND AUTOIMMUNE DISEASES

(71) Applicant: Hackensack University Medical Center, Hackensack, NJ (US)

(72) Inventors: David Schwartz, Baltimore, MD (US); Sujatha Iyengar, Baltimore, MD (US)

(73) Assignee: Hackensak University Medical Center, Hackensack, NJ (US)

( * ) Notice: Subject to any disclaimer, the term of this patent is extended or adjusted under 35 U.S.C. 154(b) by 0 days.

(21) Appl. No.: 15/173,079

(22) Filed: Jun. 3, 2016

(65) Prior Publication Data

US 2016/0361300 A1 Dec. 15, 2016

Related U.S. Application Data

(60) Provisional application No. 62/173,810, filed on Jun. 10, 2015.

(51) Int. Cl.
*A61K 31/4184* (2006.01)
*A61K 9/00* (2006.01)
(Continued)

(52) U.S. Cl.
CPC ........ *A61K 31/4184* (2013.01); *A61K 9/0053* (2013.01); *A61K 9/20* (2013.01);
(Continued)

(58) Field of Classification Search
CPC .. A61K 31/4184; A61K 31/551; A61K 45/06; A61K 9/0053; A61K 9/20;
(Continued)

(56) References Cited

U.S. PATENT DOCUMENTS

| 4,105,027 A | 8/1978 | Lundquist |
| 4,192,309 A | 3/1980 | Paulsen |

(Continued)

FOREIGN PATENT DOCUMENTS

WO 9116038 A1 10/1991

OTHER PUBLICATIONS

Yoshioka K, et al, Overexpression of Small GTP-binding Protein RhoA Promotes Invasion of Tumor Cells1, Cancer Res. 59(8): 2004-2010 (1999).

(Continued)

*Primary Examiner* — Savitha M Rao
(74) *Attorney, Agent, or Firm* — McCarter & English LLP

(57) ABSTRACT

The described invention relates to methods for preventing or treating graft-versus-host disease while preserving a graft-versus-tumor effect, increasing survival of, preserving alloreactivity, or a combination thereof in a patient with a tumor receiving a transplant. The described methods comprise administering to the patient a therapeutic amount of a pharmaceutical composition comprising a Rho kinase inhibitor compound, e.g., telmisartan or related angiotensin receptor blockers, and a pharmaceutically acceptable excipient. The therapeutic amount may be effective to attenuate graft-versus-host disease and to preserve the graft-versus-tumor effect of the transplant.

19 Claims, 7 Drawing Sheets

(51) Int. Cl.
*A61K 9/20* (2006.01)
*A61K 31/551* (2006.01)
*A61K 45/06* (2006.01)
*G01N 33/564* (2006.01)
*C12Q 1/48* (2006.01)
*G01N 33/574* (2006.01)

(52) U.S. Cl.
CPC ............ *A61K 31/551* (2013.01); *A61K 45/06* (2013.01); *C12Q 1/485* (2013.01); *G01N 33/564* (2013.01); *G01N 33/57484* (2013.01); *G01N 2333/47* (2013.01); *G01N 2333/5421* (2013.01); *G01N 2333/55* (2013.01); *G01N 2333/70578* (2013.01); *G01N 2400/50* (2013.01); *G01N 2800/245* (2013.01); *G01N 2800/52* (2013.01)

(58) Field of Classification Search
CPC ............... C12Q 1/485; G01N 2333/47; G01N 2333/5421; G01N 2333/55; G01N 2333/70578; G01N 2400/50; G01N 2800/245; G01N 2800/52; G01N 33/564; G01N 33/57484
See application file for complete search history.

(56) References Cited

U.S. PATENT DOCUMENTS

| | | | |
|---|---|---|---|
| 4,227,522 | A | 10/1980 | Paulsen |
| 4,627,432 | A | 12/1986 | Newell et al. |
| 4,811,731 | A | 3/1989 | Newell et al. |
| 5,035,237 | A | 7/1991 | Newell et al. |
| 6,921,527 | B2 | 7/2005 | Platz et al. |
| 9,051,320 | B1 | 6/2015 | Evans |
| 2006/0078615 | A1 | 4/2006 | Kohlrausch |
| 2013/0029948 | A1 | 1/2013 | Roppe et al. |
| 2013/0150326 | A1* | 6/2013 | Roppe ................. C07D 209/30 514/64 |

OTHER PUBLICATIONS

Zhu F, et al., Rho kinase inhibitor fasudil suppresses migration and invasion though down-regulating the expression of VEGF in lung cancer cell line A549, Med Oncol. 28(2): 565-571 (2011).
Hewitt CW et al., Federation of American Societies for Experimental Biology, FASEB J. 3: 5233 (1989).
Alberts B, et al. "Chapter 24: The adaptive immune system." Molecular Biology of the Cell, 4th Edition, Garland Science, New York (2002), 60 pgs.
Alevriadou BR, CAMs and Rho small GTPases: gatekeepers for leukocyte transendothelial migration. Focus on "VCAM-1-mediated Rac signaling controls endothelial cell-cell contacts and leukocyte transmigration", Am J Physiol Cell Physiol. 285(2): C250-252 (2003).
Antin JH, T-cell depletion in GVHD: less is more?, Blood. 117(23): 6061-6062 (2011).
Arab HH, Et Al., Telmisartan Attenuates Colon Inflammation, Oxidative Perturbations and Apoptosis in a Rat Model of Experimental Inflammatory Bowel Disease, PLoS One. 9(5): e97193 (2014).
Arck P, et al., Is there a 'gut-brain-skin axis'?, PetraExp Dermatol. 19(5): 401-405 (2010).
Bahr IN, et al., High-Dose Treatment With Telmisartan Induces Monocytic Peroxisome Proliferator-Activated Receptor-g Target Genes in Patients With the Metabolic Syndrome, Hypertension. 58(4):725-732 (2011).
Bardi G, et al., FEBS Lett. 542(1-3): 79-83 (2003).
Barreiro O, et al., Dynamic interaction of VCAM-1 and ICAM-1 with moesin and ezrin in a novel endothelial docking structure for adherent leukocytes, J Cell Biol. 157(7): 1233-1245 (2002).

Battaglia M, et al., Rapamycin Promotes Expansion of Functional CD4CD25FOXP3 Regulatory T Cells of Both Healthy Subjects and Type 1 Diabetic Patientsl, J Immunal. 177(12): 8338-8347 (2006).
Benais-Pont G, et al.' Identification of a tight junction-associated guanine nucleotide exchange factor that activates Rho and regulates paracellular permeability, J Cell Biol. 160(5): 729-740 (2003).
Bivalacqua TJ, et al., RhoARho-kinase suppresses endothelial nitric oxide synthase in the penis: A mechanism for diabetes-associated erectile dysfunction, Proc Natl Acad Sci USA. 101(24): 9121-9126 (2004).
Bourguignon LY, et al., Rho-Kinase (ROK) Promotes CD44v3,8_10-Ankyrin Interaction and Tumor Cell Migrationin Metastatic Breast Cancer Cells, Cell Motil Cytoskeleton. 43(4): 269-287 (1999).
Brunstein CG, et al., Infusion of ex vivo expanded T regulatory cells in adults transplanted with umbilical cord blood: safety profile and detection kineticsBlood. 117(3): 1061-1070 (2011).
Chapter 1 of Goodman and Gilman's The Pharmacological Basis of Therapeutics, 10th Edition, McGraw-Hill, New York (2001).
Chen X, et al, A critical role for the retinoic acid signaling pathway in the pathophysiology of gastrointestinal graft-versus-host disease, Blood. 121(19): 3970-3980 (2013).
Chetty VT, et al, Metabolic effects of telmisartan in subjects with abdominal obesity: A prospective randomized controlled trial, Blood Pressure. 23(1): 54-60 (2014).
Cianchetti S, et al., Anti-inflammatory and anti-oxidant properties of telmisartan in cultured human umbilical vein endothelial cells, Atherosclerosis. 198(1): 22-28 (2008).
Cooke KR, et al., LPS antagonism reduces graft-versus-host disease and preserves graft-versus-leukemia activity after experimental bone marrow transplantation, J Clin Invest. 107(12): 1581-1589 (2001).
Croft DR, et al., Conditional ROCK Activation in vivo Induces Tumor Cell Dissemination and Angiogenesis, cancer Res. 64(24): 8994-9001 (2004).
Deeg HJ, How I treat refractory acute GVHD, Blood. 109(10): 4119-4126 (2007).
Desai-Mehta A, et al., Hyperexpression of CD40 ligand by B and T cells in human lupus and its role in pathogenic autoantibody production, J Clin Invest. 97(9): 2063-2073 (1996).
Dignan FL, et al, Diagnosis and management of acute graft-versus-host disease, Br J Haematol. 158(1):30-45 (2012).
Engelhardt BG, et al., Regulatory T cell expression of CLA or a4b7 and skin or gut acute GVHD outcomes, Bone Marrow Transplant. 46(3): 436-442 (2011).
Engelhardt BG, et al., Tissue-specific regulatory T cells: biomarker for acute graft-vs-host disease and survival, Exp Hematol. 40(12): 974-982 (2012).
Eriguchi Y, et al., Graft-versus-host disease disrupts intestinal microbial ecology by inhibiting Paneth cell production of a-defensins, Blood. 120(1): 223-231 (2012).
Etienne S, et al., ICAM-1 Signaling Pathways Associated with Rho Activation in Microvascular Brain Endothelial Cells1, J Immunol. 161(10): 5755-5761 (1998).
Fanning SL, et al., Unraveling Graft-versus-Host Disease and Graft-versusLeukemia Responses Using TCR V(3 Spectratype Analysis in a Murine Bone Marrow Transplantation Model, J Immunol. 190(1): 447-457 (2013).
Ferrara JL, et al., Regenerating islet-derived 3-alpha is a biomarker of gastrointestinal graft-versus-host disease, Blood. 118(25): 6702-6708 (2011).
Ferrara JLM, et al., Graft-versus-Host Disease Lancet. 373(9674): 1550-1561 (2009).
Forclaz, A, et al., Angiotensin II Receptor Blockade Is There Truly a Benefit of Adding an ACE Inhibitor?, Hypertension. 41(1), 31-36 (2003).
Fukumoto Y, et al., Anti-ischemic Effects of Fasudil, a Specific Rho-Kinase Inhibitor, in Patients With Stable Effort Angina, J Cardiovasc Pharmacal. 49(3): 117-121 (2007).
Garcia-Mata R, et al., The invisible hand: regulation of RHO GTPases by RHOGDIs, Nat Rev Mol Cell Biol. 12(8): 193-504(2011).

(56) References Cited

OTHER PUBLICATIONS

Goulmy E, et al., Mismatches of Minor Histocompatibility Antigens Between HLA-Identical Donors and Recipients and the Development of Graft-Versus-Host Disease After Bone Marrow Transplantation N. Engl J Med. 334(5): 281-285 (1996).
Hata Y, et al., Antiangiogenic Properties of Fasudil, a Potent Rho-kinase Inhibitor, Jpn J Ophthalmol. 52(1): 16-23 (2008).
Hess AD, Chronic graft-versus-host disease: a breakdown of self-tolerance?, Blood. 105(12): 4548-4549 (2005).
Hewitt CW et al., Composite Tissue (LIMB) Allografts in Rats: III. Development of Donor-Host Lymphoid Chimeras in Long-Term Survivors, Transplantation. 41:39 (1986);.
Hewitt CW et al., Development of Stable Mixed T Cell Chimerism and Transplantation Tolerance Without Immune Modulation in Recipients of Vascularized Bone Marrow Allografts, Transplantation. 50: 766-772 (1990).
Hewitt CW et al., Lymphocyte Chimerism in a Full Allogeneic Composite Tissue (Rat-Limb) Allograft Model Prolonged With Cyclosporine, Transplant Proc. 20: 272 (1988).
Hill GR, Ferrara JL, The primacy of the gastrointestinal tract as a target organ of acute graft-versus-host disease: rationale for the use of cytokine shields in allogeneic bone marrow transplantation, Blood. 95(9): 2754-2759 (2000).
Hilmi I, et al, Endotoxemia is common following abdominal organ transplantation and is associated with reperfusion and rejection, J Organ Dysfunction. 5(4): 254-260 (2009).
Holler E, et al, The Role of Bacteria and Pattern Recognition Receptors in GvHD, Int J Inflam. 2010: 814326 (2010).
Ikeda T, et al, Usefulness of the endotoxin activity assay as a biomarker to assess the severity of endotoxemia in critically ill patients, Innate Immun. 20(8): 881-887 (2014).
Nokuchi K, et al., J Cardiovasc Pharmacol. 44(3): 275-277 (2004).
International Search Report for Application No. PCT/US16/35799 dated Sep. 6, 2016.
Yengar S, et al, Treatment with a Rho Kinase Inhibitor Improves Survival from Graft-Versus-Host Disease in Mice after MHC-Haploidentical Hematopoietic Cell Transplantation, Biol Blood Marrow Transplant. 20(8): 1104-1111 (2014).
Jacobsohn DA, et al., Graft-versus-host disease Weight loss and malnutrition in patients with chronic graft-versushost disease, Bone Marrow Transplant. 29(3): 231-236 (2002).
Janeway, CA Jr., Semin Immunol. 1(1): 13-20 (1989).
Jenq RR, et al., Regulation of intestinal inflammation by microbiota following allogeneic bone marrow transplantation J Exp Met 209(5): 903-911 (2012).
Kamai T, et al, Significant Association of Rho/ROCK Pathway with Invasion and Metastasis of Bladder Cancer1, Olin Cancer Res. 9(7): 2632-2641 (2003).
Kapur R, et al., B-cell involvement in chronic graft-versus-host disease, Haematologica. 93(11): 1702-1711 (2008).
Pidala J, Graft-vs-Host Disease Following Allogeneic Hematopoietic Cell Transplantation Cancer Control. 18(4): 268-276 (2011).
Przepiorka D, et al., Bone Marrow Transplant. 15(6):825-828 (1995).
Reddy P, Ferrara JLM, Mouse models of graft-versus-host disease. Feb. 28, 2009. In: StemBook (Internet). Cambridge (MA): Harvard Stem Cell Institute; 2008).
Reshef R, et al., Blockade of Lymphocyte Chemotaxis in Visceral Graft-versus-Host Disease, N. Engl J Med. 367 (2): 135-145 (2012).
Rezvani AR and Storb RF, Separation of graft-vs.-tumor effects from graft-vs.-host Disease in allogeneic hematopoietic cell transplantation J. Autoimmun. 30(3): 172-179 (2008).
Riento K, Ridley AJ, Rocks:Multifunctional Kinases in Cell Behaviour, Nat Rev Mol Cell Biol. 4(6): 446-456 (2003).
Ringden O, et al, Effect of acute and chronic GVHD on relapse and survival after reduced-intensity conditioning allogeneic transplantation for myeloma, Bone Marrow Transplant. 47(6): 831-837 (2012).
Ringden O, et al., The allogeneic graft-versus-cancer effect, Br J Haematol. 147(5): 614-633 (2009).
Rolink AG et al., The Autoantigen-Binding B Cell Repertoires of Normal and of Chronically Graft-Versus-Host-Diseased Mice, J Exp Med. 165: 1675-1687 (1987).
Romaschin AD, et al., Bench-to-bedside review: Clinical experience with the endotoxin activity assay, Crit Care. 16(6): 248 (2012).
Sahaie, Marshall CJ, Rock and Dia have opposing effects on adherens junctions downstream of Rho, Nat Cell Biol. 4(6): 408-415 (2002).
Sanada Y, et al, Impact of endotoxin measured by an endotoxin activity assay during liver transplantation, J Surg Res.180(2): 349-355 (2013).
Sanchez-Madrid F, Del Pozo Ma, Leukocyte polarization in cell migration and immune interactions, EMBO J. 18 (3): 501-511 (1999).
Sawhney AS, et al., Bioerodible Hydrogels Based on Photopolymerized Poly(ethylene glycol)-co-poly(a-hydroxy acid) Diacrylate Macromers, Macromolecules. 26(4): 581-587 (1993).
Schumacher H, Mancia G, The Safety profile of telmisartan as monotherapy or combined with hydrochlorothiazide: A retrospective analysis of 50 studies, Blood Press Suppl. 1:32-40 (2008).
Schwartz, RH, T Cell Anergy, Annu Rev Immunol:, 21: 305-334 (2003).
Sharpe M, et al., Telmisartan A Review of its Use in Hypertension, Drugs 61(10):1501-1529 (2001).
Shimokawa H, et al, Anti-anginal Effect of Fasudil, a Rho-Kinase Inhibitor, in Patients With Stable Effort Angina: A Multicenter Study, J Cardiovasc Pharmacol. 40(5): 751-761 (2002).
Signori A, et al, Chronic GVHD is associated with lower relapse risk irrespective of stem cell source among patients receiving transplantation from unrelated donors, Bone Marrow Transplant. 47(11): 1474-1478 (2012).
Siragusa M, Sessa WC, Telmisartan Exerts Pleiotropic Effects in Endothelial Cells and Promotes Endothelial Cell Duiescence and Survival, Arterioscler Thromb Vasc Biol. 33(8): 1852-1860 (2013).
Smith A, et al., LFA-1-induced T cell migration on ICAM-1 involves regulation of MLCK-mediated attachment and Rock dependent detachment, J Cell Sci. 116(Pt 15): 3123-3133 (2003).
Somlyo A V, et al, Rho-Kinase Inhibitor Retards Migration and in Vivo Dissemination of Human Prostate Cancer Cells, Biochem Biophys Res Commun. 269(3): 652-659 (2000).
Somlyo AV, et al., Faseb J., Rho kinase and matrix metalloproteinase inhibitors cooperate to inhibit angiogenesis and growth of human prostate cancer xenotransplants, 17(2): 223-234 (2003).
Song EK, et al., Rosiglitazone prevents graft-versus-host disease (GVHD), Transpl Immunol. 27(2-3): 128-137 (2012).
Street CA, Bryan BA, Rho kinase proteins—pleiotropic modulators of cell survival and apoptosis, Anticancer Res. 31(11): 3645-3657 (2011).
Taams LS, et al, Human anergic/suppressive CD4+CD25+ T cells: a highly differentiated and apoptosis-prone population, Eur J Immunol. 31(4):1122-1131 (2001).
Takata K, et al, Fasudil-induced hypoxia-inducible factor-1A degradation disrupts a hypoxia-driven vascular endothelial growth factor autocrine mechanism in endothelial cells, Mol Cancer Ther. 7(6): 1551-1561 (2008).
Tapash K. Ghosh et al. 'Transdermal and Topical Drug Delivery Systems, eds., 1997, pp. 249-297.
Tominaga T, et al, Inhibition of PMA-induced, LFA-I-dependent Lymphocyte Aggregation by ADP Ribosylation of the Small Molecular Weight GTP Binding Protein, rho, J Cell Biol. 120(6): 1529-1537 (1993).
Usui T, et al., Inhibition of Corneal Neovascularization by Blocking the Angiotensin II Type 1 Receptor, Invest Ophthalmol Vis Sci. 49(10): 4370-4376 (2008).
Van Buul JD, Hordijk PL, Signaling in Leukocyte Transendothelial Migration, Arterioscler Thromb Vasc Biol. 24 (5):824-833 (2004).
Vander Lugt MT, et al., ST2 as a Marker for Risk of Therapy-Resistant Graft-versus-Host Disease and Death, N Engl J Med. 369(6): 529-539 (2013).
Vicari RM, et al., Efficacy and Safety of Fasudil in Patients With Stable Angina, J Am Coll Cardiol. 46(10): 1803-1811 (2005).

(56) References Cited

OTHER PUBLICATIONS

Vishnubhotla R, et al., Rock-II mediates colon cancer invasion via regulation of MMP-2 and MMP-13 at the site of invadopodia as revealed by multiphoton imagingLab Invest. 87(11): 1149-1158 (2007).
Von Bonin M, et al., Therapy of acute graft-versus-host disease, Cell Ther Transplant. 2(6): 10.3205/ctt-2010-en-000057.01 (2010).
Walcher D, et al, Ivabradine Reduces Chemokine-Induced CD4-Positive LymphocyteMigration, Hypertension. 51 (2): 259-266 (2008).
Wang DS, et al, Enhancement of migration and invasion of hepatoma cells via a Rho GTPase signaling pathway, World J Gastroenterol. 10(2): 299-302 (2004);.
Wang Y, et al., ROCK Isoform Regulation of Myosin Phosphatase and Contractility in Vascular Smooth Muscle Cells, Circ Res. 104(4): 531-540 (2009).
Wang, Q., G.M. Garrity, J.M. Tiedje, J.R. Cole. Naïve Bayesian Classifier for Rapid Assignment of rRNA Sequences into the New Bacterial Taxonomy 2007 Naive Bayesian classifier for rapid assignment of rRNA sequences into the new bacterial taxonomy. Appl. Environ. Microbiol. 73:5261-5267, doi:1O.1128/Aem.00062-07).
Ward Y, et al, The GTP binding proteins Gem and Rad are negative regulators of the Rho-Rho kinase pathway, J Cell Biol. 157(2): 291-302 (2002).
Washida N, et al, Rho-kinase inhibition ameliorates peritoneal fibrosis and angiogenesis in a rat model of peritoneal sclerosis, Nephrol Dial Transplant. 26(9): 2770-2779 (2011).
Wheeler AP, Ridley AJ, Why three Rho proteins? RhoA, RhoB, RhoC, and cell motility, Exp Cell Res. 301(1): 43-49 (2004).
White WB, Comparative Effects of Telmisartan in the Treatment of Hypertension J Clin Hypertens. 4: 20-25 (2002).
Wilson DB et al, Idiotypic Regulation of T Cells in GraftVersus-Host Disease and Autoimmunity, Immunol Rev. 107: 159-177 (1989).
Witzenrath M, et al, Rho-kinase and contractile apparatus proteins in murine airway hyperresponsiveness, Exp Toxicol Pathol. 60(1): 9-15 (2008).
Wolff D, et al., Consensus Conference on Clinical Practice in Chronic GVHD: Second-Line Treatment of Chronic Graft-versus-Host Disease, Biol Blood Marrow Transplant. 17(1): 1-17 (2011).
Wong CC, et al., Deleted in Liver Cancer 1 (DLC1) Negatively Regulates Rho/ROCK/MLC Pathway in Hepatocellular Carcinoma, PLoS One. 3(7):e2779 (2008).
Xue F, et al., Blockade of Rho/Rho-associated coiled coil-forming kinase signaling can prevent progression of hepatocellular carcinoma in matrix metalloproteinase-dependent manner, Hepatol Res. 38(8): 810-817 (2008).
Ying H, et al, The Rho kinase inhibitor fasudil inhibits tumor progression in human and rat tumor models, Mol Cancer Ther. 5(9): 2158-2164 (2006).
Yoneda A, et al, the Rho kinases I and II regulate different aspects of myosin II activity, J Cell Biol. 170(3): 443-453 (2005).
Kennedy MJ, Hess AD, Autologous graft-versus-host disease, Med Oncol. 12(3): 149-156 (1995).
Kishi T, et al., Rho-Kinase Inhibitor Improves Increased Vascular Resistance and Impaired Vasodilation of the Forearm in Patients With Heart Failure, Circulation. 111(21): 2741-2747 (2005).
Kobayashi N, et al., Cardioprotective Mechanism of Telmisartan via PPAR-?-eNOS Pathway in Dahl Salt-Sensitive Hypertensive RatsAm J Hypertens. 21(5): 576-581 (2008).
Komanduri KV, Targeting neovascularization in GVHD, Blood. 121(17): 3303-3304 (2013).
Kronenberg, M, Rudensky A, Regulation of immunity by self-reactive T cells, Nature. 435(7042): 598-604 (2005).
Kuno M, et al, Rho-kinase inhibitors decrease TGF-b-stimulated VEGF synthesis through stress-activated protein kinase/c-Jun N-terminal kinase in osteoblasts, Biochem Pharmacol. 77(2): 196-203 (2009).
Langer R. "New methods of drug delivery." Science. 249(4976): 1527-1533 (1990).
Lee JH et al, Roles of p-ERM and Rho-ROCK signaling in lymphocyte polarity and uropod formation, J Cell Biol. 167(2): 327-337 (2004).
Lee SJ, et al., High-resolution donor-recipient HLAmatching contributes to the success of unrelated donor marrow transplantation, Blood. 110(13): 4576-4583 (2007).
Lee SJ, et al., Severity of chronic graft-versus-host disease: association with treatment-related mortality and relapse, Blood. 100(2): 406-414 (2002).
Leonhardt F, et al., Inflammatory neovascularization during graft-versus-host disease is regulated by av integrin and miR-100, Blood. 121(17): 3307-3318 (2013).
Levine JE, et al., Acute graft-versus-host disease biomarkers measured during therapy can predict treatment outcomes: a Blood and Marrow Transplant Clinical Trials Network study, Blood. 119(16): 3854-3860 (2012).
Levine JE, et al., Clinical Applications for Biomarkers of Acute and Chronic Graft-versus-Host Disease, Biol Blood Marrow Transplant. 18(1 Suppl): S116-S124 (2012).
Li B, et al., Involvement of Rho/ROCK signalling in small cell lung cancer migration through human brain microvascular endothelial cells, FEBS Lett. 580(17): 4252-4260 (2006).
Liu C, et al, Targeting the Shift from M1 to M2 Macrophages in Experimental Autoimmune Encephalomyelitis Mice Treated with Fasudil, PLoS OneE. 8(2): e54841 (2013).
Liu Z, et al, Treatment with telmisartan/rosuvastatin combination has a beneficial synergistic effect on ameliorating Th17/Treg functional imbalance in hypertensive patients with carotid atherosclerosis, Atherosclerosis. 233(1): 291-299 (2014).
Lozupone, C., M. Hamady, R. Knight, 2006, UniFrac-an online tool for comparing microbial community diversity in a phylogenetic context. BMC Bioinformatics. 7:371. doi: 10. 118611471-2105-7-371.
Luzuy S et al, Autoimmunity After Induction of Neonatal Tolerance to Alloantigens: Role of B Cell Chimerism and FI Donor B Cell Activation, J Immunol. 146: 4420-4426 (1986).
LV M, et al, Ceruloplasmin Is a Potential Biomarker for aGvHD following Allogeneic Hematopoietic Stem Cell Transplantation, PLoS One. 8(3):e58735 (2013).
Lämmermann T, et al, Rapid leukocyte migration by integrinindependent flowing and squeezing, Nature. 453 (7191): 51-55 (2008).
Magurran, A.E. 2004. Measuring Biological Diversity. Blackwell Pub., Malden, MA.2004, pgs. 1-70.
Marshall JC, et al, Diagnostic and Prognostic Implications of Endotoxemia in Critical Illness: Results of the Medic Study, J Infect Dis. 190(3): 527-534 (2004).
Marshall SR, Technology Insight: ECP for the treatment of GvHD—can we offer selective immune control without generalized immunosuppression?, Nat Clin Pract Oncol. 3(6): 302-314 (2006).
Masumoto A, et al., Suppression of Coronary Artery Spasm by the Rho-Kinase Inhibitor Fasudil in Patients With Vasospastic Angina, Circulation. 105(13): 1545-1547 (2002).
Michel MC, et al., Safety of Telmisartan in Patients with Arterial Hypertension an Open-Label Observational Study, Drug Saf. 27(5):335-344 (2004).
Mihaescu A, et al., Rho kinase signalling mediates radiation-induced inflammation and intestinal barrier dysfunction, Br J Surg. 98(1): 124-131 (2011).
Ming XF, et al., Rho GTPase/Rho Kinase Negatively Regulates Endothelial Nitric Oxide Synthase Phosphorylation through the Inhibition of Protein Kinase B/Akt in Human Endothelial Cells, Mol Cell Biol. 22(24): 8467-8477 (2002).
Mizukami Y, et al., Hypoxic Regulation of Vascular Endothelial Growth Factor through the Induction of Phosphatidylinositol 3-Kinase/Rho/ROCK and c-Myc, J Biol Chem. 281(20): 13957-13963 (2006).
Mohri M, et al, Rho-Kinase Inhibition With Intracoronary Fasudil Prevents Myocardial Ischemia in Patients With Coronary Microvascular Spasm, J Am Coll Cardiol. 41(1): 15-19 (2003).

(56) References Cited

OTHER PUBLICATIONS

Morgan-Fisher M, et al., Regulation of ROCK Activity in Cancer, J Histochem Cytochem. 61(3):185-198 (2013).
Mueller BK, et al., Rho Kinase, A Promising Drug Target for Neurological Disorders, Nat Rev Drug Discov. 4(5): 387-398 (2005).
Mueller T, Dieplinger B, Expert Rev Mol Diagn. 13(1): 13-30 (2013).
Nagai N, et al, Selective Suppression of Pathologic, but Not Physiologic, Retinal Neovascularization by Blocking the Angiotensin II Type 1 Receptor, Invest Ophthalmol Vis Sci. 46(3): 1078-1084 (2005).
Nakabayashi H, Shimizu K, HA1077, a Rho kinase inhibitor, suppresses glioma-induced angiogenesis by targeting the Rho-Rock and the mitogen-activated protein kinase kinase/extracellular signal-regulated kinase (MEK/ERK) signal pathways , Cancer Sci. 102(2): 393-399 (2011).
Nohria A, et al., Rho Kinase Inhibition Improves Endothelial Function in Human Subjects With Coronary Artery Disease, Circ Res. 99(12): 1426-1432 (2006).
Noma K, et al., ROCK1 mediates leukocyte recruitment and neointima formation following vascular injury, J Clin Invest. 118(5): 1632-1644 (2008).
Ogawa T, et al., Rho-Associated Kinase Inhibitor Reduces Tumor Recurrence After Liver Transplantation in a Rat Hepatoma Model, Am J Transplant. 7(2): 347-355 (2007).
Olson MF, Applications for ROCK kinase inhibition, Curr Opin Cell Biol. 20(2): 242-248 (2008).
Otsuka T, et al., Vasodilatory Effect of Subsequent Administration of Fasudil, a Rho-Kinase Inhibitor, Surpasses That of Nitroglycerin at the Concentric Coronary Stenosis in Patients With Stable Angina Pectoris, Circ J. 70(4): 402-408 (2006).
Ozeki K, et al., Telmisartan Inhibits Cell Proliferation by Blocking Nuclear Translocation of ProHB-EGF C-Terminal Fragment in Colon Cancer CellsPLoS One. 8(2): e56770 (2013).
Paczesny S, Discovery and validation of graft-versus-host disease biomarkers, Blood. 121(4): 585-594 (2013).
Patel PA, Patravale VB, Commercial Telmisartan Tablets: A Comparative Evaluation with Innovator Brand Micardis Int J Pharm Sci Res. 1(8): 282-292 (2010).
Patterson AE, Komgold R, Infusion of Select Leukemia-Reactive TCR Vβ+ T Cells Provides Graft-Versus-Leukemia Responses With Minimization of Graft-Versus-Host Disease Following Murine Hematopoietic Stem Cell Transplantation, Biol Blood Marrow Transplant. 7(4): 187-196 (2001).
Paul WE, "Chapter 1: The immune system: an introduction." Fundamental Immunology, 4th Edition, Lippincott-Raven Publishers, Philadelphia (1999), 20 pgs.
Pavletic SZ, Fowler DH, Are we making progress in GVHD prophylaxis and treatment? Hematology Am Soc of Hematol Educ Program. 2012: 251-264 (2012).
Penack O, et al, Graft-versus-host disease: regulation by microbe-associated molecules and innate immune receptors, Blood. 115(10): 1865-1872 (2010).
Penack O, et al, Inhibition of Neovascularization to Simultaneously Ameliorate Graft-vs-Host Disease and Decrease Tumor Growth, J Natl Cancer Inst. 102(12): 894-908 (2010).
Penack O, et al, The importance of neovascularization and its inhibition for allogeneic hematopoietic stem cell transplantation, Blood. 117(16): 4181-4189 (2011).
Petrovic A, et al, LPAM (a4b7 integrin) is an important homing integrin on alloreactive T cells in the development of intestinal graft-versus-host disease, Blood. 103(4): 1542-1547 (2004).
Pidala J, et al., Overlap subtype of chronic graft-versus-host disease is associated with an adverse prognosis, functional impairment, and inferior patient-reported outcomes: a Chronic Graft-versus-Host Disease Consortium studyHaematologica. 97(3): 451-458 (2012).

\* cited by examiner

A. Survival of irradiated B6C3F1 mice receiving ATBM + T cells +/- fasudil

B. Weight of surviving F1 hosts over time

ATBM n=n'=n"=18; ATBM+T+fasudil n=26, n'=21, n"=19
ATBM + T n=24, n'=9, n"=8; Irradiated n=10, n'=n"=0

USE OF TELMISARTAN TO PREVENT AND TREAT GRAFT VERSUS HOST DISEASE AND OTHER ALLOIMMUNE AND AUTOIMMUNE DISEASES

CROSS-REFERENCE TO RELATED APPLICATION

This application claims the benefit of priority to U.S. Provisional Application No.: 62/173,810 filed on Jun. 10, 2015, the entire contents of which are incorporated by reference herein.

STATEMENT OF GOVERNMENT FUNDING

This invention was made with government support under 1R21AI092501-01 awarded by the National Institutes of Health. The government has certain rights in the invention.

FIELD OF THE INVENTION

The described invention generally relates to Graft vs. Host Disease (GVHD) and other alloimmune and autoimmune diseases.

BACKGROUND OF THE INVENTION

Allogeneic hematopoietic cell transplantation (HCT) is a potentially curative therapy for patients with hematologic malignancies. A significant obstacle to success following this therapeutic approach is the onset of Graft versus Host Disease (GVHD) syndromes, which pose a significant threat of morbidity, escalated and prolonged immunosuppressive therapy, organ dysfunction, impaired quality of life, and ultimately an increased risk for mortality.

Immunologic Response

The ability of an individual's immune responses to distinguish between his/her own antigens and foreign antigens is termed self-tolerance. The occasional breakdown of this self-tolerance can result in serious autoimmune diseases. Conversely, under certain conditions a foreign antigen acts as a tolerogen, establishing a state in which the animal fails to develop an immune reaction. Tolerance and immunity are alternative responses; it follows that tolerance is specific and is directed to particular antigenic determinants.

Graft-Versus-Host Disease (GVHD)

Immune tolerance of donor T cells to the host is broken in Graft-versus-host disease (GVHD), an immunological complication associated with high dose cancer treatment followed by allogeneic bone marrow and stem cell transplantation. Hess A D, Blood. 105(12): 4548-4549 (2005). Acute GVHD caused by mature donor lymphocyte alloreactivity to host tissue antigens is a major cause of morbidity and mortality following allogeneic blood and marrow transplantation (BMT). Multiple organs can be involved, including the skin, liver, and lungs, but the main cause of death appears to be damage to the intestinal tract (IT) small and large bowel, resulting in sepsis, diarrhea, and shock. Hill G R, Ferrara J L, Blood. 95(9): 2754-2759 (2000); Chen X, et al., Blood. 121(19): 3970-3980 (2013). A prominent finding is that GVHD disrupts IT microbial communities by inhibiting Paneth cell production of antimicrobial α-defensins. Eriguchi Y, et al., Blood. 120(1): 223-231 (2012).

A conceptual model for GVHD suggests that the disease is composed of phases that include tissue damage from conditioning therapy and activation of antigen-presenting cells, activation of donor T cells resulting in differentiation and migration, and finally an effector phase in which host tissue damage is mediated by inflammatory cytokines, such as TNFα and IL-1, and effector cells, most notably cytotoxic T cells. Pidala J, Cancer Control. 18(4): 268-276 (2011). It is additionally complicated by disturbances in pathways of immunological reconstitution and failure to acquire immunological tolerance, thereby resulting in both alloimmune and autoimmune attacks on multiple host tissues. Pavletic S Z, Fowler D H, Hematology Am Soc of Hematol Educ Program. 2012: 251-264 (2012).

Consistent with a 2005 National Institutes of Health (NIH) Consensus Conference, classification of GVHD is based on clinical presentation rather than time of onset. Pidala J, et al., Haematologica. 97(3): 451-458 (2012).

Acute GVHD manifestations include erythematosus or maculopapular rash, nausea and vomiting or diarrhea and cholestatic hepatitis, and historically were limited to within 100 days following HCT. Grading for acute GVHD divides acute GVHD into four stages based on the extent of involvement of the skin, liver and gastrointestinal tract. In stage I, there is a skin rash over <25% of the body, bilirubin is measured at 26-60 μmol/L, with a gut fluid loss of 500-1000 mL/day. In stage II, a skin rash covers 25-50% of the body, the bilirubin is measured at 61-137 μmol/L, and the gut loses from 1000-1500 mL/day. Stage III is characterized by involving >50% of the skin, the bilirubin is measured at 138-257 μmol/L, and the gut has lost more than 1500 mL/day. Stage IV is characterized by bullae desquamation (blisters with shedding of epidermal cells) of skin, the bilirubin exceeds >257 μmol/L, and the gut fluid loss is >2500 mL/day or ileus (disruption of the normal propulsive ability of the gastrointestinal tract; bowel obstruction).

Acute GVHD manifestations occurring more than 100 days after hematopoietic cell transplantation are classified as "persistent", "recurrent", or "late onset" acute GVHD, depending on the antecedent history of acute GVHD and absence of other chronic GVHD manifestations. Pidala J, et al., Haematologica. 97(3): 451-458 (2012).

Classic chronic GVHD, which can result in multiple clinical features involving multiple sites (eyes, gastrointestinal tract, liver, lungs, heart, bone marrow and kidneys), is defined by diagnostic manifestations of chronic GVHD without characteristic features of acute GVHD, with extensive skin involvement, elevated bilirubin, gastrointestinal tract involvement and progressive onset from acute GVHD as poor prognostic findings. Pidala J, et al., Haematologica. 97(3): 451-458 (2012).

An overlap subtype of GVHD, which displays features of both chronic and acute GVHD, is a condition with an adverse prognosis, functional impairment, and significantly higher symptom burden. Patients with acute features have significantly higher non-relapse mortality and lower overall survival rates. These patients suffer significant and diverse functional impairments compared to those with classic chronic GVHD, suggesting a systemic functional impairment beyond the more direct ramifications of concurrent acute GVHD manifestations. Pidala J, et al., Haematologica. 97(3): 451-458 (2012).

One of the major determinants for development and severity of acute GVHD in human transplantation is disparity in major and minor histocompatibility antigens, with an increasing number of mismatched antigens predicting greater risk of acute GVHD and nonrelapse mortality. Goulmy E, et al., N. Engl J Med. 334(5): 281-285 (1996); Lee S J, et al., Blood. 110(13): 4576-4583 (2007). Polymorphism in non-HLA genes, including cytokines such as tumor necrosis factor (TNF), interleukin 10 (IL-10), interferon gamma, KIR polymorphism, and NOD2/CARD15 gene polymorphism, also may contribute to the development and severity of acute GVHD. Pidala J, Cancer Control. 18(4): 268-276 (2011).

There are several hypotheses as to mechanisms of chronic GVHD pathogenesis: (1) thymic damage, in part mediated by prior acute GVHD, may impair the process of negative selection by thymic medullary epithelial cells that eliminate pathogenic T cells responsible for immunity; (2) the potential role of transforming growth factor-beta (TGF-β) has been supported by amelioration of chronic GVHD manifestations after neutralization of this cytokine in murine models, and the clinical observation of an inverse relationship between TGF-β signaling in CD4 and CD8 cells and the risk of chronic GVHD; and (3) B cells may play a role in chronic GVHD pathogenesis. Pidala J, Cancer Control. 18(4): 268-276 (2011).

Current Therapeutic Strategies

Approximately 50% of individuals that receive an allogeneic donor transplant will develop some degree of GVHD, and it is not clear that a major improvement has occurred in the ability to prevent or treat GVHD. Pavletic S Z, Fowler D H, Hematology Am Soc of Hematol Educ Program. 2012: 251-264 (2012).

Fatal GVHD, manifesting as chronic inflammatory destruction of the gut, lungs, skin, and other organs, can be completely abrogated in animals and humans by careful depletion of mature lymphocytes from the donor bone marrow graft prior to transplantation. However, when this approach has been taken in patients being treated for various cancers, the incidence of tumor relapse is greatly increased, due to the loss of graft vs. tumor effect (GVTE), which is characterized by an immune response to a graft recipient's tumor cells by a donor's transplanted immune cells in the bone marrow or peripheral blood. In fact, an inverse correlation exists between the severity of GVHD and the incidence of tumor relapse. Ringdén O, et al., Bone Marrow Transplant. 47(6): 831-837 (2012); Lee S J, et al., Blood. 100(2): 406-414 (2002); Signori A, et al., Bone Marrow Transplant. 47(11): 1474-1478 (2012).

Donor immune cells that have been implicated in the GVTE include CD4+ T cells, CD8+ T cells and natural killer (NK) cells. These cells are believed to use Fas-dependent killing and perforin degranulation to eradicate malignant cells. In addition to immune cells, cytokines such as interleukin-2 (IL-2), interferon-γ (IFN-γ) and tumor necrosis factor-α (TNF-α) have been shown to potentiate GVTE. Ringdén O, et al., Br J Haematol. 147(5): 614-633 (2009).

Control of GVHD, with maintenance of GVTE, is the goal of current management, which relies heavily on steroid immunosuppression. Marshall S R, Nat Clin Pract Oncol. 3(6): 302-314 (2006). Glucocorticoids such as methylprednisolone or prednisone combined with cyclosporine are used to treat acute GVHD, but adverse effects with corticosteroids include increased risk of infections, hyperglycemia, psychosis, and myopathy. Prolonged use of corticosteroids can cause osteoporosis, cataract formation, and aseptic bone necrosis.

Clinical trials investigating GVHD unresponsive to steroid treatment have reported success with the following treatments: daclizumab, etanercept, extracorporeal photopheresis, infliximab, mycophenolate mofetil, pentostatin, rituximab, tacrolimus, thalidomide, and imatinib mesylate. Von Bonin M, et al., Cell Ther Transplant. 2(6): 10.3205/ctt-2010-en-000057.01 (2010); Wolff D, et al., Biol Blood Marrow Transplant. 17(1): 1-17 (2011). Other approaches, include antithymocyte globulin, denileukin diftitox, monoclonal antibodies (such as alemtuzumab), sirolimus, oral nonabsorbable corticosteroids such as budesonide or beclomethasone dipropionate, intra-arterial corticosteroids, and infusions of mesenchymal stem cells. Dignan F L, et al., Br J Haematol. 158(1):30-45 (2012); Deeg H J, Blood. 109(10): 4119-4126 (2007). None of these approaches has thus far proved satisfactory.

A solution for overcoming GVHD while preserving GVTE appears to be possible. In mice, several different strategies for preventing intestinal tract (IT) damage have been observed to reduce or eliminate GVHD mortality while preserving systemic alloreactivity and GVTE.

One strategy is to identify tumor specific antigens (TSAs) and the T cell clones recognizing them, so that these may be selectively expanded, while all other alloreactive clones are removed. Patterson A E, Korngold R, Biol Blood Marrow Transplant. 7(4): 187-196 (2001); Fanning S L, et al., J Immunol. 190(1): 447-457 (2013). The limited number of well-defined TSAs is an obstacle to this approach. So, too, is the removal of alloreactivity, which comprises a much broader, stronger, and less readily evaded response repertoire than that generated against a single TSA.

Four general strategies can be envisioned for protecting the gut against GVHD while preserving general alloreactivity: 1) Reduce accumulation of alloreactive effector lymphocytes at the most vulnerable IT sites via tighter endothelial barriers, decreased diapedesis and motility of alloreactive T cells (Teffs) (e.g., Th17 and Th1), and/or decreased gut-specific homing. 2) Inhibit IT neovascularization by donor derived endothelial cells (ECs) differentiating from precursors (EPCs) under hypoxic conditions—recently revealed to be a major source of IT pathology during GVHD. Komanduri K V, Blood. 121(17): 3303-3304 (2013); Leonhardt F, et al., Blood. 121(17): 3307-3318 (2013); Penack O, et al., Blood. 117(16): 4181-4189 (2011); Penack O, et al., J Natl Cancer Inst. 102(12): 894-908 (2010). 3) Activate and expand allospecific IT regulatory T cells (Tregs) to suppress the inflammatory and cytotoxic responses of effector T cells (Teffs) (e.g., Th17 and Th1) in a localized manner. In this scenario, Tregs protect the most vulnerable GVHD sites (gut mucosa), while alloreactive Teffs (e.g., Th17 and Th1) remain in circulation throughout the rest of the body, available to encounter and eliminate residual host derived tumor cells. 4) Reduce intestinal leakage of bacteria and bacterial products such as endotoxin, which induce local and systemic inflammation at sites of GVHD.

The potential utility of the first approach is supported by dramatically reduced GVHD in mice receiving allogenic cells from donors genetically defective for gut homing integrin α4β7 (Petrovic A, et al., Blood. 103(4): 1542-1547 (2004)), or retinoic acid receptors which transduce signals leading to α4β7 upregulation. Chen X, et al., Blood. 121 (19): 3970-3980 (2013). Comparable protection against IT GVHD was seen when allograft donor lymphocytes were depleted of α4β7+ populations prior to transplantation. Petrovic A, et al., Blood. 103(4): 1542-1547 (2004). In these three cases where α4β7 mediated gut homing cells were absent, host syngeneic tumors were still strongly rejected. In transplant patients, maraviroc (a CCR5 blocker) prevented IT GVHD and acute (within 100 days) death, but was associated with ~20% greater relapse at 1 year (vs. historical controls)—not statistically significant, but suggestive of immune suppression with respect to GVTE, perhaps due to the widespread distribution of CCR5 on immune cells. Reshef R, et al., N Engl J Med. 367(2): 135-145 (2012).

The potential utility of the second strategy (inhibition of neovascularization) is supported by analogous mouse studies with anti-vascular endothelial (VE)-cadherin mAb, which reduced IT neovascularization and IT GVHD while leaving anti-tumor alloreactivity intact. Penack O, et al., J Natl Cancer Inst. 102(12): 894-908 (2010).

The third approach also appears promising, based on clinical studies. Recently, an inverse correlation between Tregs bearing IT homing receptors α4β7 and acute GVHD in patients has been demonstrated. Engelhardt B G, et al., Bone Marrow Transplant. 46(3): 436-442 (2011); Engelhardt B G, et al., Exp Hematol. 40(12): 974-982 (2012). Addition of donor Tregs (not α4β7 selected) suppressed GVHD without significant early interference with anti-tumor immunity. Brunstein C G, et al., Blood. 117(3): 1061-1070 (2011).

The fourth approach has been supported by numerous pre-clinical and clinical studies showing reduced GVHD in mice and patients pre-treated with gut sterilization, or in some cases, pro-biotics prior to allogeneic transplantation, and by studies showing that inhibition of rho kinase prevents intestinal leak syndrome after irradiation. Mihaescu A, et al., Br J Surg. 98(1): 124-131 (2011).

Rho Associated Coiled-Coil Kinase (ROCK) Proteins

Cancer-associated changes in cellular behavior, such as modified cell-cell contact, increased migratory potential, and generation of cellular force, all require alteration of the cytoskeleton. Rho-associated coiled-coil kinase (ROCK) proteins belong to the protein kinase A, G, and C family (AGC family) of classical serine/threonine protein kinases, a group that also includes other regulators of cell shape and motility, such as citron Rho-interacting kinase (CRIK), dystrophia myotonica protein kinase (DMPK), and the myotonic dystrophy kinase-related Cdc42-binding kinases (MRCKs). The main function of ROCK signaling is regulation of the cytoskeleton through the phosphorylation of downstream substrates, leading to increased actin filament stabilization and generation of actin-myosin contractility. Morgan-Fisher M, et al., J Histochem Cytochem. 61(3):185-198 (2013).

Two homologous mammalian serine/threonine kinases, Rho-associated protein kinases I and II (ROCK I and II), are key regulators of the actin cytoskeleton acting downstream of the small GTPase Rho. ROCK I (alternatively called ROK β) and ROCK II (also known as Rho kinase or ROK α) are 160-kDa proteins encoded by distinct genes. The mRNA of both kinases is ubiquitously expressed, but ROCK I protein is mainly found in organs such as liver, kidney, and lung, whereas ROCK II protein is mainly expressed in muscle and brain tissue. The two kinases have the same overall domain structure and have 64% overall identity in humans, with 89% identity in the catalytic kinase domain. Both kinases contain a coiled-coil region (55% identity) containing a Rho-binding domain (RBD) and a pleckstrin homology (PH) domain split by a C1 conserved region (80% identity) (See FIG. 1). Despite a high degree of homology between the two ROCKs, as well as the fact that they share several common substrates, studies have shown that the two ROCK isoforms also have distinct and non-redundant functions. For example, ROCK I has been shown to be essential for the formation of stress fibers and focal adhesions, whereas ROCK II is required for myosin II-dependent phagocytosis.

ROCKs exist in a closed, inactive conformation under quiescent conditions, which is changed to an open, active conformation by the direct binding of guanosine triphosphate (GTP)-loaded Rho. Morgan-Fisher M, et al., J Histochem Cytochem. 61(3):185-198 (2013). Rho is a small GTPase which functions as a molecular switch, cycling between guanosine diphosphate (GDP) and guanosine triphosphate (GTP) bound states under signaling through growth factors or cell adhesion receptors. Morgan-Fisher M, et al., J Histochem Cytochem. 61(3):185-198 (2013). GTPases are hydrolase enzymes that bind and hydrolyze GTP. In a similar way to ATP, GTP can act as an energy carrier, but it also has an active role in signal transduction, particularly in the regulation of G protein activity. G proteins, including Rho GTPases, cycle between an inactive GDP-bound and an active GTP-bound conformation (See FIG. 2). The transition between the two conformational states occurs through two distinct mechanisms: activation by GTP loading and inactivation by GTP hydrolysis. GTP loading is a two-step process that requires the release of bound GDP and its replacement by a GTP molecule. Nucleotide release is a spontaneous but slow process that has to be catalyzed by RHO-specific guanine nucleotide exchange factors (RHOGEFs), which associate with RHO GTPases and trigger release of the nucleotide. The resulting nucleotide-free binary complex has no particular nucleotide specificity. However, the cellular concentration of GTP is markedly higher than that of GDP, which favors GTP loading, resulting in the activation of RHO GTPases.

Conversely, to turn off the switch, GTP has to be hydrolyzed. This is facilitated by RHO-specific GTPase-activating proteins (RHOGAPs), which stimulate the intrinsically slow hydrolytic activity of RHO proteins. Although guanine nucleotide exchange factors (GEFs) and GTPase-activating proteins (GAPs) are the canonical regulators of this cycle, several alternative mechanisms, such as post-translational modifications, may fine-tune the RHO switch. In addition, inactive RHO GTPases are extracted by RHO-specific guanine nucleotide dissociation inhibitors (RHOGDIs) from cell membranes to prevent their inappropriate activation and to protect them from misfolding and degradation. Garcia-Mata R, et al., Nat Rev Mol Cell Biol. 12(8): 493-504 (2011).

Many proteins aid in activating and inhibiting ROCK I and ROCK II. Table 1 shows molecules that regulate ROCK by direct binding. Morgan-Fisher M, et al., J Histochem Cytochem. 61(3):185-198 (2013). For example, small GTP-binding protein RhoA (which controls cell adhesion and motility through organization of the actin cytoskeleton and regulation of actomyosin contractility) (Yoshioka K, et al., Cancer Res. 59(8): 2004-2010 (1999)), RhoB (which is localized primarily on endosomes, has been shown to regulate cytokine trafficking and cell survival) and RhoC (which may be more important in cell locomotion) (Wheeler A P, Ridley A J, Exp Cell Res. 301(1): 43-49 (2004)), associate with and activate the ROCK proteins. Other GTP binding proteins, such as RhoE, Ras associated with diabetes (Rad) and Gem (a member of the RGK family of GTP-binding proteins within the Ras superfamily possessing a ras-like core and terminal extensions whose expression inhibited ROK beta-mediated phosphorylation of myosin light chain and myosin phosphatase, but not LIM kinase (see Ward Y, et al., J Cell Biol. 157(2): 291-302 (2002)), inhibit ROCK, binding at sites distinct from the canonical Ras binding domain (RBD). Association with the PDK1 kinase promotes ROCK I activity by blocking RhoE association.

TABLE 1

Molecules that Regulate ROCK by Direct Binding

| Partner | Binding Site on ROCK | Outcome of Interaction | Cell Types | References |
|---|---|---|---|---|
| ROCK I | | | | |
| PDK1 | aa 375-415 | Retention of ROCK I at the plasma membrane. Increases cortical actin-myosin contractility and increases amoeboid migration. Prevents negative regulation of ROCKI activity by RhoE. PDK1 does not affect ROCK I kinase activity. | (H) Malignant melanoma, (R) breast cancer, (H) squamous cell carcinoma | Pinner and Sahal 2008 |
| MYBPH | aa 17-535 | Reduces MLC phosphorylation. Decreases single-cell motility leading to reduced lung adenocarcinoma invasion and metastasis. | (H) Lung adenocarcinoma | Hosono et al. 2011 |
| RhoE | aa 1-420 | Stress fiber disassembly and suppresses hepatocellular carcinoma motility and invasiveness. In competition with PDK1 for the same binding site on ROCK I. Regulates ROCK I kinase activity. | (H) Squamous cell and (H) hepatocellular carcinoma, (H) malignant melanoma | Riento et al. 2003; Pinner and Sahal 2008; Ma W et al. 2012 |
| Shroom2 | aa 593-1062 | Shroom2 and ROCK interact and regulate endothelial cell contractility. Reduced Shroom 2 mRNA levels have been linked to human colorectal cancer. | (H, M) Endothelial cells | Dunlop et al. 2012; Farber et al. 2011 |
| ROCK II | | | | |
| Coronin IB | aa 1135-1381 | Inhibits ROCK II signaling to myosin | (H) Breast adenocarcinoma | Rana and Worthylake 2012 |
| CRMP-2L and -2S | aa 1-543 | CRMP-2(L) inhibits ROCK II activity, resulting in alteration of cell migration, actin cytoskeleton organization, and decreased fibronectin matrix assembly | (H) Colon and breast adenocarcinoma, (R) fibroblasts, (Ca) kidney epithelial cells | Yoneda et al. 2012 |
| Raf1 | aa 1-543 | Reduces ROCK kinase activity. Promotes STAT3/myc activation and dedifferentiation in Ras-induced skin tumors. Regulates cell motility. | (M) Skin carcinoma, (M) primary keratinocytes, (M) fibroblasts | Ehrenreiter et al. 2005, 2009; Piazzolla et al., 2005; Niault et al. 2009 |
| Dynamin 1 | aa 1135-1381 | Overexpression studies showed that dynamin I is necessary for appropriate ROCK II action on the actin cytoskeleton in neuronal cells. | (R) Brain extract | Turnuslime et al. 2009 |
| MLCP | aa 354-775 | ROCK II phosphorylates MBS and inactivates MLCP. | (R) Smooth muscle cells | Kimura et al. 1996; Wang et al. 2009 |
| Myosin II | aa 1152-1388 | Overexpression studies showed myosin II to anchor ROCK II to stress fibers | (P)Brain extract, (M, R) fibroblasts | Kawabata et al. 2004 |
| NPM/B23 | aa 5-553 | Enhances ROCK II activity. Leads to centrosome amplification. | (M) Fibroblasts | Ma Z et al. 2006; Ferretti et al. 2010 |
| P80 CRMP-1 | aa 1-543 | Overexpression studies showed p80 CRMP-1 inhibits activity of recombinant ROCK II kinase domain. ROCK II phosphorylates p80 CRMP-1. | (R) Brain extract | Leung et al. 2002 |

TABLE 1-continued

Molecules that Regulate ROCK by Direct Binding

| Partner | Binding Site on ROCK | Outcome of Interaction | Cell Types | References |
|---|---|---|---|---|
| ROCK I and II | | | | |
| Gem | aa 787-976 (ROCK I), Full length ROCK II | Overexpression studies showed that Gem abolishes ROCK I-dependent MLC phosphorylation but not LIMK activation. Prevents ROCK I-mediated cell rounding and neurite retraction in neuroblastoma cells. Binds ROCK II. | (H) Neuroblastoma | Ward et al. 2002 |
| Rad | aa 787-976 (ROCK I), aa 807-976 ROCK II | Overexpression studies showed that Rad binding prevents ROCK II-mediated cell rounding and neurite retraction in neuroblastoma cells. Binds ROCK I. | (H) Neuroblastoma | Ward et al. 2002 |
| Morgana/chp I | Full-length | Binds and reduces ROCK II kinase activity. Inhibits ROCK II-NPM interaction. Binds ROCK I containing complexes. | (H) Embryonic kidney cells, (M) embryonic fibroblasts | Ferretti et al. 2010 |
| Shroom 3 | aa 726-926 (ROCK I), aa 698-957 (ROCK II) | Recruitment of the ROCKs to apical junctions. Increases MLC phosphorylation at apical junctions. Shroom3-ROCK interaction is crucial for neuroepithelial cell arrangement and remodeling. | (C, M) Embryos, (Ca) kidney epithelial cells | Nishimura and Takeichi 2008 |

CRMP, collapsing response mediator protein; LIMK, LIM domain kinase; MBS, myosin binding subunit; MLC, myosin light chain; MLCP, myosin light chain phosphatase; MYBPH, myosin binding protein H; NPM, nucleophosmin/B23; PDK1, phosphoinositide-dependent kinase I; ROCK, Rho-associated protein kinase.
Canine (Ca), chick (C), human (H), mouse (M), porcine (P), or rat (R).

ROCK activation leads to a concerted series of events that promote force generation and morphological changes. These events contribute directly to a number of actin-myosin mediated processes, such as cell motility, adhesion, smooth muscle contraction, neurite retraction and phagocytosis. In addition, ROCK kinases play roles in proliferation, differentiation, apoptosis and oncogenic transformation, although these responses can be cell type-dependent. Olson M F, Curr Opin Cell Biol. 20(2): 242-248 (2008).

ROCK I and ROCK II promote actin-myosin mediated contractile force generation through the phosphorylation of numerous downstream target proteins, including ezrin/radixin/moesin (ERM), the LIM-kinases (LIMK), myosin light chain (MLC), and MLOC phosphatase (MLCP). ROCK phosphorylates LIM kinases-1 and -2 (LIMK1 and LIMK2) at conserved threonines in their activation loops, increasing LIMK activity and the subsequent phosphorylation of cofilin proteins, which blocks their F-actin-severing activity. ROCK also directly phosphorylates the myosin regulatory light chain, myosin light chain II (MLC), and the myosin binding subunit (MYPT1) of the MLC phosphatase to inhibit catalytic activity. Many of these effects are also amplified by ROCK-mediated phosphorylation and activation of the Zipper-interacting protein kinase (ZIPK), a serine/threonine kinase which is involved in the regulation of apoptosis, autophagy, transcription, translation, actin cytoskeleton reorganization, cell motility, smooth muscle contraction and mitosis, which phosphorylates many of the same substrates as ROCK (See FIG. 3).

The phosphorylation of MLC by ROCK provides the chemical energy for actin-myosin ratcheting, and also phosphorylates myosin light chain phosphatase (MLCP), thereby inactivating MLCP and preventing its dephosphorylation of MLC. Thus, ROCK promotes actin-myosin movement by activation and stabilization. Other known substrates of ROCK include the cytoskeleton related proteins such as the ERM proteins, and focal adhesion kinase (FAK). The ERM proteins function to connect transmembrane proteins to the cytoskeleton. Street C A, Bryan B A, Anticancer Res. 31(11): 3645-3657 (2011).

ROCK has been Linked to Apoptosis, Cell Survival, and Cell Cycle Progression

Rho-ROCK signaling has been implicated in cell cycle regulation. Rho-ROCK signaling increases cyclin D1 and Cip1 protein levels, which stimulate G1/S cell cycle progression. Morgan-Fisher M, et al., J Histochem Cytochem. 61(3):185-198 (2013). Polyploidization naturally occurs in megakaryocytes due to an incomplete mitosis, which is related to a partial defect in Rho-ROCK activation, and leads to an abnormal contractile ring lacking myosin IIA.

Rho-ROCK signaling also has been linked to apoptosis and cell survival. During apoptosis, ROCK I and ROCK II are altered to become constitutively-active kinases. Through proteolytic cleavage by caspases (ROCK I) or granzyme B (ROCK II), a carboxyl-terminal portion is removed that normally represses activity. Interaction with phosphatidyl inositol (3,4,5)-triphosphate ($PIP_3$) provides an additional regulatory mechanism by localizing ROCK II to the plasma membrane where it can undertake spatially restricted activities, i.e. the regulation by localization of enzymatic activity. Phosphorylation at multiple specific sites by polo-like kinase 1 was found to promote ROCK II activation by RhoA. Olson M F, Curr Opin Cell Biol. 20(2): 242-248 (2008). Additional Serine/Threonine and Tyrosine kinases may also regulate ROCK activity given that more phosphorylations have been identified. Olson M F, Curr Opin Cell Biol. 20(2): 242-248 (2008). Specifically, protein oligomerization induces N-terminal trans-phosphorylation. Riento K, Ridley A J, Nat Rev Mol Cell Biol. 4(6): 446-456 (2003). Other direct activators include intracellular second messengers such as arachidonic acid and sphingosylphosphorylcholine which can activate ROCK independently of Rho. Furthermore, ROCK I activity can be induced during apoptosis. Mueller B K, et al., Nat Rev Drug Discov. 4(5): 387-398 (2005).

ROCK protein signaling reportedly acts in either a pro- or anti-apoptotic fashion depending on cell type, cell context and microenvironment. For instance, ROCK proteins are essential for multiple aspects of both the intrinsic and extrinsic apoptotic processes, including regulation of cytoskeletal-mediated cell contraction and membrane blebbing, nuclear membrane disintegration, modulation of Bcl2-family member and caspase expression/activation and phagocytosis of the fragmented apoptotic bodies (FIG. 4). Mueller B K, et al., Nat Rev Drug Discov. 4(5): 387-398 (2005). In contrast, ROCK signaling also exhibits pro-survival roles (FIG. 4). Though a wealth of data exists to suggest both pro- and anti-survival roles for ROCK proteins, the molecular mechanisms that modulate these pleiotropic roles are largely unknown. Street C A, Bryan B A, Anticancer Res. 31(11): 3645-3657 (2011).

The importance of the cytoskeleton for various cellular functions, combined with the pleiotropy of ROCK targeted phosphorylation, accounts for the wide range of animal models in which ROCK inhibitors, such as Y-27632, have shown beneficial effects. These include experimental asthma, Alzheimer's disease, Parkinson's disease, systemic lupus erythematosis, cardiovascular disease, organ transplant, diabetes, and erectile dysfunction, among others. Olson M F, Curr Opin Cell Biol. 20(2): 242-248 (2008).

Data from ROCK I knockout mice supports their use to treat cardiovascular diseases. Using a variety of models that mimic chronic high blood pressure, partial or full deletion of ROCK I reduced cardiac fibrosis without affective cardiomyocyte hypertrophy. In addition, pressure overload was less effective at inducing cardiomyocyte apoptosis in ROCK I$^{-/-}$ mice relative to controls, suggesting a role for ROCK I in myocardial failure. Olson M F, Curr Opin Cell Biol. 20(2): 242-248 (2008).

Despite the considerable interest and the development of numerous potent ROCK inhibitors by different groups, there is little information in the literature reporting clinical trials with selective ROCK inhibitors. Olson M F, Curr Opin Cell Biol. 20(2): 242-248 (2008).

Selective ROCK inhibitors have not been extensively investigated in humans; only Fasudil® (also known as HA-1077) has been the subject of clinical trials. However, other ROCK inhibitors have been studied in the laboratory setting. Each ROCK inhibitor has different characteristics and specificity for the ROCK proteins. Examples of known ROCK inhibitors include, but are not limited to, Y-27632 2HCl (R&D Systems Inc., Minneapolis, Minn.), Triazovivin® (StemRD, Burlingame, Calif.), Slx-2119 (MedChem Express, Namiki Shoji Cop., LTD), WF-536 [(+)-®-4-(1-aminoethyl)-N-(4-pyridyl) benzamide monohydrochloride] (Mitsubishi Pharma Corporation, Osaka, Japan), RK1-1447 (University of South Florida, Tampa, Fla., and Moffitt Cancer Center, Tampa, Fla.; Pireddu R, et al. "Pyridylthiazole-based ureas as inhibitors of Rho associated protein kinases (ROCK1 and 2)." Medchemcomm. 2012; 3(6):699-709.), Fasudil® (Asahi-KASEI Corp., Osaka, Japan), Fasudil® hydrochloride (R&D Systems Inc., Minneapolis, Minn.), GSK429286A (R&D Systems Inc., Minneapolis, Minn.), Rockout® (EMD Millipore, Philadelphia, Pa.), SR 3677 dihydrochloride (R&D Systems Inc., Minneapolis, Minn.); SB 772077B (R&D Systems Inc., Minneapolis, Minn.), AS 1892802 (R&D Systems Inc., Minneapolis, Minn.), H 1152 dihydrochloride (R&D Systems Inc., Minneapolis, Minn.), GSK 269962 (R&D Systems Inc., Minneapolis, Minn.), HA 1100 hydrochloride (R&D Systems Inc., Minneapolis, Minn.), and Glycyl-H-1152 dihydrochloride (R&D Systems Inc., Minneapolis, Minn.).

For example, GSK429286A is a selective inhibitor of both ROCK I and ROCK II with an IC$_{50}$ of 14 nM and 63 nM, respectively. Rockout® is a cell-permeable indolopyridine compound that acts as a selective, reversible, and ATP-competitive inhibitor of ROCK with an IC$_{50}$ of 25 µM; however, it does not inhibit the activation of ROCK (although it has been shown to affect cell migration, inhibit blebbing and decrease stress fibers). SR 3677 dihydrochloride is a selective ROCK inhibitor having IC$_{50}$ values of 3 and 56 nM for ROCK II and ROCK I, respectively. SB 772077B dihydrochloride is a ROCK inhibitor with an IC$_{50}$ value of 5.6 nM for ROCK I and ROCK II. AS 1892802 is an ATP-competitive ROCK inhibitor (IC$_{50}$ values are 52 and 122 nM for human ROCK II and human ROCK I) and exhibits analgesic effects in rat models of inflammatory and noninflammatory arthritic pain. H 1152 dihydrochloride is a ROCK inhibitor that displays high selectivity over the other protein kinases (IC$_{50}$ value for ROCK II is 0.012 µM). GSK 269962 is a ROCK inhibitor that exhibits IC$_{50}$ values of 1.6 and 4 nM for ROCK I and ROCK II, respectively, and further displays greater than 30 fold selectivity for ROCK against a panel of serine/threonine kinases. Additionally, GSK 269962 has been shown to induce vasorelaxation in preconstricted rat aorta and lower blood pressure in a rat model of hypertension. HA 1100 hydrochloride is a cell-permeable active metabolite of Fasudil®, which produces ATP-competitive and reversible inhibition of ROCK and is about 100-fold selective over a range of other protein kinases (IC$_{50}$ value of ROCK II is 575.44 nM and of ROCK I 758.58 nM (both human ROCK proteins)). Additionally, HA 1100 hydrochloride has been shown to inhibit neutrophil migration and produces potent vasodilatory effects in vivo. Glycyl-H-1152 dihydrochloride is a glycyl analog of the ROCK inhibitor H 1152 dihydrochloride that displays improved ROCK II selectivity (IC$_{50}$ value is 0.0118 µM for ROCK II).

The isoquinoline derivative Fasudil® (and its monohydrochloride salt) is a cell-permeable Ca$^{2+}$ antagonist that inhibits Rho-associated Kinase (ROCK II) having an IC$_{50}$=1.6 µM. It was created as one of a series of compounds that inhibited PKA and PKC, but is significantly more potent for ROCK, with an IC$_{50}$ at least 10-fold lower than for other kinases. However, its critical target has not been identified. Although ROCK is more potently inhibited by Fasudil® than related kinases such as PKA and PKC, and many effects of Fasudil® have been reproduced in model systems by structurally distinct inhibitors such as Y-27632, it has been hypothesized that the clinical effects of Fasudil® may actually result from the inhibition of other kinases or result from the combined inhibition of ROCK plus additional kinases, such as ZIPK or LIMK. Olson M F, Curr Opin Cell Biol. 20(2): 242-248 (2008). In animal models, Fasudil® has been shown to be effective in reversing blood vessel spasm and constriction that may occur after an episode of bleeding into the subarachnoid space surrounding the brain, a condition termed subarachnoid hemorrhage (SAH). Post-marketing surveillance studies on SAH patients have found that in over 1400 patients examined Fasudil® was well tolerated and safe. These findings have encouraged Fasudil® clinical trials for additional indications. Olson M F, Curr Opin Cell Biol. 20(2): 242-248 (2008).

Clinical trials with Fasudil® have focused on indications linked to the cardiovascular system. For example, human trials have been carried out to assess the efficacy of Fasudil® in: acute ischemic stroke, cerebral blood flow, stable angina pectoris, coronary artery spasm, heart failure-associated vascular resistance and constriction, pulmonary arterial hypertension essential hypertension, atherosclerosis and aortic stiffness. Clinical trials in the United States currently are underway to determine whether Fasudil® would be useful in treating atherosclerosis and hypercholesterolemia (ClinicalTrials.gov Identifier: NCT00120718), and Reynaud's phenomenon (ClinicalTrials.gov Identifier: NCT00498615), which is a vasospastic disorder that causes painful, pale and cold extremities. Olson M F, Curr Opin Cell Biol. 20(2): 242-248 (2008).

MLC phosphorylation is also important in the context of cell motility and signal transduction. Over the past 15 years, numerous cell functions have been revealed to be ROCK dependent, including leukocyte chemotaxis, diapedesis, cytokine secretion and responsiveness (Noma K, et al., J Clin Invest. 118(5): 1632-1644 (2008); Lämmermann T, et al., Nature. 453(7191): 51-55 (2008); Smith A, et al., J Cell Sci. 116(Pt 15): 3123-3133 (2003); Van Buul J D, Hordijk P L, Arterioscler Thromb Vasc Biol. 24(5): 824-833 (2004); Benais-Pont G, et al., J Cell Biol. 160(5): 729-740 (2003); Li B, et al., FEBS Lett. 580(17): 4252-4260 (2006); Nohria A, et al., Circ Res. 99(12): 1426-1432 (2006); Bardi G, et al., FEBS Lett. 542(1-3): 79-83 (2003); Lee J H, et al., J Cell Biol. 167(2): 327-337 (2004)), and tumor cell invasiveness and metastasis. Xue F, et al., Hepatol Res. 38(8): 810-817 (2008); Wong C C, et al., PLoS One. 3(7): e2779 (2008); Ogawa T, et al., Am J Transplant. 7(2): 347-355 (2007); Wang D S, et al., World J Gastroenterol. 10(2): 299-302 (2004); Vishnubhotla R, et al., Lab Invest. 87(11): 1149-1158 (2007); Kamal T, et al., Clin Cancer Res. 9(7): 2632-2641 (2003); Sahai E, Marshall C J, Nat Cell Biol. 4(6): 408-415 (2002); Croft D R, et al., Cancer Res. 64(24): 8994-9001 (2004); Mizukami Y, et al., J Biol Chem. 281 (20): 13957-13963 (2006); Somlyo A V, et al., FASEB J. 17(2): 223-234 (2003); Somlyo A V, et al., Biochem Biophys Res Commun. 269(3): 652-659 (2000); Ying H, et al., Mol Cancer Ther. 5(9): 2158-2164 (2006); Bourguignon L Y, et al., Cell Motil Cytoskeleton. 43(4): 269-287 (1999). Additional targets of ROCK serine/threonine kinase activity include cytoskeletal ezrin, radixin, moesin, and focal adhesion kinase. Barreiro O, et al., J Cell Biol. 157(7): 1233-1245 (2002). Further, ROCK inhibits endothelial nitric oxide synthase (eNOS) production of NO, (Bivalacqua T J, et al., Proc Natl Acad Sci USA. 101(24): 9121-9126 (2004); Ming X F, et al., Mol Cell Biol. 22(24): 8467-8477 (2002)) thus, decreasing blood flow in NO regulated vascular beds. ROCK inhibition, therefore, increases blood flow in NO regulated vasculature, and also appears to enhance the integrity of endothelial barriers, decreasing capillary leakage and endothelial cell apoptosis. (Noma K, et al., J Clin Invest. 118(5): 1632-1644 (2008); Lämmermann T, et al., Nature. 453(7191): 51-55 (2008); Smith A, et al., J Cell Sci. 116(Pt 15): 3123-3133 (2003); Van Buul J D, Hordijk P L, Arterioscler Thromb Vasc Biol. 24(5): 824-833 (2004); Benais-Pont G, et al., J Cell Biol. 160(5): 729-740 (2003); Li B, et al., FEBS Lett. 580(17): 4252-4260 (2006); Nohria A, et al., Circ Res. 99(12): 1426-1432 (2006); Bardi G, et al., FEBS Lett. 542(1-3): 79-83 (2003); Lee J H, et al., J Cell Biol. 167(2): 327-337 (2004); Tominaga T, et al., J Cell Biol. 120(6): 1529-1537 (1993); Sánchez-Madrid F, del Pozo M A, EMBO J. 18(3): 501-511 (1999); Alevriadou B R, Am J Physiol Cell Physiol. 285(2): C250-252 (2003). Additionally, ROCK inhibition antagonizes vascular endothelial growth factor (VEGF) by more than one pathway. Etienne S, et al., J Immunol. 161(10): 5755-5761 (1998); Zhu F, et al., Med Oncol. 28(2): 565-571 (2011); Nakabayashi H, Shimizu K, Cancer Sci. 102(2): 393-399 (2011); Washida N, et al., Nephrol Dial Transplant. 26(9): 2770-2779 (2011); Kuno M, et al., Biochem Pharmacol. 77(2): 196-203 (2009); Takata K, et al., Mol Cancer Ther. 7(6): 1551-1561 (2008); Hata Y, et al., Jpn J Ophthalmol. 52(1): 16-23 (2008). Finally, recent findings indicate that, in the context of experimental autoimmune encephalomyelitis, ROCK inhibition promotes Treg differentiation by shifting macrophages from M1 to the Treg inducing M2 phenotype. Liu C, et al., PLoS OneE. 8(2): e54841 (2013).

A tenuous connection of cytoskeletal proteins to the pathology of GVHD has been suggested. Studies have reported that the presence of autoantibodies and alloantibodies to cytoskeletal proteins (microfilaments, microtubules and intermediate filaments) correlates with disease severity. Anti-cytoskeletal intermediate filament antibodies have been reported. Kapur R, et al., Haematologica. 93(11): 1702-1711 (2008). In patients with extensive cGVHD with generalized skin involvement and/or lung fibrosis, higher levels of anti-PDGFR antibodies have been detected; these antibodies were shown to activate the Ha-Ras, ERK1/2, ROS signal transduction cascade, leading to increased type I collagen-gene expression. Kapur R, et al., Haematologica. 93(11): 1702-1711 (2008).

Telmisartan

Telmisartan (Micardis®, Boehringer Ingelheim) is an FDA approved and licensed angiotensin receptor blocker (ARB). It has been safely used for over eighteen (18) years as an anti-hypertensive drug. Immune suppression has not been reported as an increased risk during the post-marketing period. The anti-hypertensive effects of telmisartan are now thought to reflect the combination of ARB activity, PPARγ activation, and ROCK inhibition. Telmisartan has been found to be an agonist for peroxisome proliferator activated receptor gamma (PPARγ). PPARγ, also known as the glitazone receptor, or NR1C3 (nuclear receptor subfamily 1, group C, member 3) is a member of a group of nuclear receptor protein that function as transcription factors, and play essential roles in the regulation of cellular differentiation, development, metabolism, and tumorigenesis. PPARγ agonists (e.g. glitazones) are used as insulin sensitizing drugs to treat type 2 diabetes, and also have anti-hyperlipidemia benefits. More recently, anti-inflammatory functions of PPARγ agonists have been elucidated, some of which appear to be due to reduction in the activity of ROCK. Telmisartan has been found to be as potent an inhibitor of ROCK as Y-27632, a specific ROCK inhibitor. Kobayashi N, et al., Am J Hypertens. 21(5): 576-581 (2008).

Because recognition of telmisartan as a PPARγ agonist has been slow, and its potency as a ROCK inhibitor is not widely appreciated, its potential as a GVHD attenuator has not been explored. Additionally, there may be concerns that any positive effects will not be cleanly attributable to a single mechanism of action. However, protection from GVHD by the ROCK inhibitor, Fasudil®, similar in potency and mechanism of action to Y-27632, has been demonstrated. Iyengar S, et al., Biol Blood Marrow Transplant.

20(8): 1104-1111 (2014). Fasudil® and Y-27632 have been much more extensively studied than telmisartan, over the past two decades, with respect to the three potentially protective mechanisms envisioned. Fasudil® occupies the ATP binding pocket of ROCK's enzymatically functional kinase domain, thereby preventing phosphorylation of myosin light chain II (MLC) and MLC phosphatase (MLCP). Riento K, Ridley A J, Nat Rev Mol Cell Biol. 4(6): 446-456 (2003); Yoneda A, et al., J Cell Biol. 170(3): 443-453 (2005); Wang Y, et al., Circ Res. 104(4): 531-540 (2009). Phosphorylation of MLC activates it for actin filament binding and ratcheting, while phosphorylation of MLCP prevents this enzyme from de-phosphorylating (inactivating) MLC. Thus, ROCK potentiates smooth muscle contraction from two angles, both inhibited by Fasudil®. This explains Fasudil®'s anti-spasmodic properties on arterial smooth muscle, and its anti-hypertensive effects in pre-clinical and clinical studies (Vicari R M, et al., J Am Coll Cardiol. 46(10): 1803-1811 (2005); Shimokawa H, et al., J Cardiovasc Pharmacol. 40(5): 751-761 (2002); Fukumoto Y, et al., J Cardiovasc Pharmacol. 49(3): 117-121 (2007); Otsuka T, et al., Circ J. 70(4): 402-408 (2006); Masumoto A, et al., Circulation. 105(13): 1545-1547 (2002); Mohri M, et al., J Am Coll Cardiol. 41(1): 15-19 (2003); Inokuchi K, et al., J Cardiovasc Pharmacol. 44(3): 275-277 (2004); Kishi T, et al., Circulation. 111(21): 2741-2747 (2005)), as well as anti-asthmatic effects in OVA induced asthma models. Witzenrath M, et al., Exp Toxicol Pathol. 60(1): 9-15 (2008). Fasudil®, unavailable for clinical use in Europe or USA, has been safely used in Japan and other Asian countries for almost two decades without evidence of immune suppression.

Additionally, rosiglitazone, a specific PPARγ agonist, has been shown to suppress GVHD inflammation in a similar mouse model although survival curves were not followed. Song E K, et al., Transpl Immunol. 27(2-3): 128-137 (2012). Telmisartan has been shown to have a protective effect against rat colitis, a condition that shares common pathways with GVHD. Arab H H, et al., PLoS One. 9(5): e97193 (2014).

Telmisartin has been shown to abrogate lymphocyte chemotaxis, in part by abrogation of SDF-1 induced chemotaxis. Walcher D, et al., Hypertension. 51(2): 259-266 (2008). Additionally, telmisartan may maintain gut endothelial barriers by protecting endothelial cells (ECs) from inflammation mediated destruction. Cianchetti S, et al., Atherosclerosis. 198(1): 22-28 (2008); Siragusa M, Sessa W C, Arterioscler Thromb Vasc Biol. 33(8): 1852-1860 (2013). Telmisartan has also been shown to prevent neovascularization in corneal systems. Usui T, et al., Invest Ophthalmol Vis Sci. 49(10): 4370-4376 (2008); Nagai N, et al., Invest Ophthalmol Vis Sci. 46(3): 1078-1084 (2005). Finally, telmisartan has been shown to increase the ratio of protective Tregs:autoreactive Th17 cells (Liu Z, et al., Atherosclerosis. 233(1): 291-299 (2014)), and a very recent report demonstrates anti-inflammatory effects of telmisartan in the setting of chemically induced acute colitis. Arab H H, et al., PLoS One. 9(5): e97193 (2014). Multiple genetic pathways activated by inflammation and oxidative stress, along with inflammatory cell infiltrates and gross pathology of weight loss and diarrhea, were attenuated by pre-treatment with telmisartan.

A recent study has shown that telmisartan may inhibit cell proliferation in colon cancer cells induced by disrupting nuclear translocation of C-terminal fragments of proheparin-binding epidermal growth factor like growth factor. Ozeki K, et al., PLoS One. 8(2): e56770 (2013).

Clinical Experience with Micardis® Brand of Telmisartan

The antihypertensive effects of Micardis® brand telmisartan have been demonstrated in multiple placebo-controlled clinical trials, studying a range of 20 to 160 mg; one of these examined the antihypertensive effects of telmisartan and hydrochlorothiazide in combination. Micardis® package insert. Ingelheim, Germany: Boehringer Ingelheim Int'l.; 2014. The studies involved a total of 1773 patients with mild to moderate hypertension (diastolic blood pressure of 95 to 114 mm Hg), 1031 of which were treated with telmisartan. Following once daily administration of telmisartan, the magnitude of blood pressure reduction from baseline after placebo subtraction was approximately (SBP/DBP) 6-8/6 mm Hg for 20 mg, 9-13/6-8 mm Hg for 40 mg, and 12-13/7-8 mm Hg for 80 mg telmisartan doses. Larger doses (up to 160 mg) did not appear to cause a further decrease in blood pressure.

The incidence of symptomatic orthostasis after the first dose in all controlled trials was low (0.04%). Upon initiation of antihypertensive treatment with telmisartan, blood pressure was reduced after the first dose, with a maximal reduction achieved by about four (4) weeks. Most of the blood pressure lowering effect was observed within the first two (2) weeks of treatment. With cessation of treatment with Micardis® tablets, blood pressure gradually returned to baseline values over a period of several days to one (1) week. The antihypertensive effect of telmisartan is not influenced by patient age, gender, weight, or body mass index. Blood pressure response in African American patients (usually a low-renin population) is noticeably less than that in Caucasian patients.

Drug Interactions and Cautions for Telmisartan

Telmisartan is contraindicated during pregnancy, and no subjects should be enrolled if there is a chance of pregnancy during the telmisartan treatment phase of a clinical trial.

In patients with an activated renin-angiotensin system, such as volume- or salt-depleted patients (e.g., those being treated with high doses of diuretics), symptomatic hypotension may occur after initiation of therapy with telmisartan. Patients should be taken off their non-telmisartan antihypertensives for two (2) days prior to administration of telmisartan. Blood chemistries, blood pressure, and urination frequency should be monitored to ensure adequate hydration and normokalemia prior to starting telmisartan.

Hyperkalemia may occur in patients on telmisartan, particularly in patients with advanced renal impairment, heart failure, on renal replacement therapy, or on potassium supplements, potassium-sparing diuretics, potassium-containing salt substitutes or other drugs that increase potassium levels.

As the majority of telmisartan is eliminated by biliary excretion, patients with biliary obstructive disorders or hepatic insufficiency can be expected to have reduced clearance.

As a consequence of inhibiting the renin-angiotensin-aldosterone system, changes in renal function may occur in susceptible individuals. In patients whose renal function may depend on the activity of the renin-angiotensin-aldosterone system (e.g., patients with severe congestive heart failure or renal dysfunction), treatment with angiotensin receptor antagonists has been associated with oliguria and/or progressive azotemia and (rarely) with acute renal failure and/or death.

In patients who are elderly, volume-depleted (including those on diuretic therapy), or with compromised renal function, co-administration of NSAIDs, including selective COX-2 inhibitors, with telmisartan, may result in deterioration of renal function, including possible acute renal failure. These effects are usually reversible.

Drugs without known telmisartan interactions include: acetaminophen, amlodipine, glyburide, simvastatin, hydrochlorothiazide, warfarin, and ibuprofen.

Telmisartan is not metabolized by the cytochrome P450 system and has no effects in vitro on cytochrome P450 enzymes, except for some inhibition of CYP2C19. Telmisartan is not expected to interact with drugs that inhibit cytochrome P450 enzymes; it is also not expected to interact with drugs metabolized by cytochrome P450 enzymes, except for possible inhibition of the metabolism of drugs metabolized by CYP2C19.

Adverse Events for Telmisartan

The most common adverse events (≥1%) reported in hypertension trials of Micardis® are back pain, sinusitis, and diarrhea (see Table 2). When Micardis® was used for the reduction of cardiovascular risk, the serious adverse events (≥1%) were intermittent claudication and skin ulcer. The incidence of adverse events was not dose-related and did not correlate with gender, age, or race of patients.

TABLE 2

Adverse Events Occurring at an Incidence of ≥1% in Patients Treated with MICARDIS ® and at a Greater Rate Than Patients Treated with Placebo

| | Telmisartan n = 1455 (%) | Placebo n = 380 (%) |
|---|---|---|
| Upper respiratory tract infection | 7 | 6 |
| Back pain | 3 | 1 |
| Sinusitis | 3 | 2 |
| Diarrhea | 3 | 2 |
| Pharyngitis | 1 | 0 |

In addition to these adverse events, the following events occurred at a rate of ≥1% but were at least as frequent in the placebo group: influenza-like symptoms, dyspepsia, myalgia, urinary tract infection, abdominal pain, headache, dizziness, pain, fatigue, coughing, hypertension, chest pain, nausea, and peripheral edema. Discontinuation of therapy because of adverse events was required in 2.8% of 1455 patients treated with Micardis® tablets and 6.1% of 380 placebo patients in placebo-controlled clinical trials. The incidence of cough occurring with telmisartan in 6 placebo-controlled trials was identical to that noted for placebo-treated patients (1.6%).

Pharmacokinetics of Telmisartan

Following oral administration, peak concentrations (Cmax) of telmisartan are reached in 0.5 to 1 hour after dosing. Food slightly reduces the bioavailability of telmisartan, with a reduction in the area under the plasma concentration-time curve (AUC) of about 6% with the 40 mg tablet and about 20% after a 160 mg dose. The absolute bioavailability of telmisartan is dose dependent. At 40 and 160 mg the bioavailability is 42% and 58%, respectively. The pharmacokinetics of orally administered telmisartan are nonlinear over the dose range 20 to 160 mg, with greater than proportional increases of plasma concentrations ($C_{max}$ and AUC) with increasing doses. Telmisartan shows bi-exponential decay kinetics with a terminal elimination half-life of approximately 24 hours. Trough plasma concentrations of telmisartan with once daily dosing are about 10 to 25% of peak plasma concentrations. Telmisartan has an accumulation index in plasma of 1.5 to 2.0 upon repeated once daily dosing.

Telmisartan is highly bound to plasma proteins (>99.5%), mainly albumin and orosomucoid. Plasma protein binding is constant over the concentration range achieved with recommended doses. The volume of distribution for the highly lipophilic telmisartan is approximately 500 liters indicating additional tissue binding.

Following either intravenous or oral administration of $^{14}C$-labeled telmisartan, most of the administered dose (>97%) is eliminated unchanged in feces via biliary excretion; only minute amounts are found in urine (0.91% and 0.49% of total radioactivity, respectively).

To date, no ideal treatment or therapy exists that is effective to modulate GVHD pathology while preserving GVTE, following allogenic BMT.

The described invention provides methods for treating and preventing GVHD, increasing subject survival and preserving alloreactivity of transplanted T cells in transplant patients comprising administering a therapeutic amount of telmisartan, wherein the therapeutic amount may be effective to reduce the incidence of GVHD and to preserve GVTE in a patient receiving a transplant.

SUMMARY OF THE INVENTION

According to one aspect, the described invention provides a method for treating a patient with a tumor receiving a transplant comprising administering to the patient a therapeutic amount of a pharmaceutical composition comprising: (i) a Rho kinase inhibitor compound; and (ii) a pharmaceutically acceptable carrier, wherein the therapeutic amount may be effective to attenuate graft-versus-host disease (GVHD) while preserving a graft-versus-tumor effect (GVTE).

According to some embodiments, the GVHD is acute. According to some embodiments, the GVHD is chronic.

According to some embodiments, the transplant is allogeneic. According to some embodiments, the transplant is xenogeneic. According to anther embodiment, the transplant is a bone marrow transplant. According to some embodiments, the transplant is a vascularized composite allotransplant (VCA).

According to some embodiments, the pharmaceutical composition further comprises a ROCK inhibitor. According to some embodiments, the pharmaceutical composition further comprises an angiotensin receptor blocker (ARB). According to some embodiments, the pharmaceutical composition further comprises a peroxisome proliferator activated receptor gamma (PPARγ) agonist.

According to some embodiments, the Rho kinase inhibitor compound is telmisartan.

According to some embodiments, the administering to the patient is orally. According to some embodiments, the administering to the patient is parenterally.

According to some embodiments, the therapeutic amount of the pharmaceutical composition is effective to increase patient survival; to preserve alloreactivity; or (c) to increase the ratio of Treg:alloreactive Teffectors; to reduce tumor burden, reduce tumor growth, reduce tumor progression, reduce tumor proliferation, increase survival, or a combination thereof.

According to some embodiments, the tumor is a nonhematologic solid tumor. According to some embodiments, the tumor is a selected from the following group consisting of an adenoma, a blastoma, a carcinoma, a lymphoma, a melanoma, and a sarcoma.

According to some embodiments, the therapeutic amount of the pharmaceutical composition is effective to improve weight recovery following GVHD-related weight loss.

According to one aspect, the described invention provides a method of predicting and monitoring progression of GVHD in a patient with a tumor receiving a transplant comprising: (i) obtaining pre-transplant and post-transplant liquid samples from the patient; (ii) detecting from the pre-transplant and post-transplant whole blood samples biomarkers for GVHD, quantifying and comparing the amounts of biomarkers in the pre-transplant and post-transplant whole blood samples; (iii) predicting and correlating the degree of GVHD progression in the patient based on increased biomarker levels in the post-transplant liquid samples; and treating the patient with a therapeutically effective regimen to reduce the GVHD progression.

According to some embodiments, the liquid sample is selected from the following group: serum, plasma, and whole blood.

According to some embodiments, the biomarker is selected from the following group: elafin, IL-8, TNFR1, HGF, reg3a, IL-2RA, ST2, and Lipid A endotoxin.

According to some embodiments, the therapeutically effective regimen to reduce the GVHD progression comprises administering a pharmaceutical composition comprising a therapeutic amount of a Rho kinase inhibitor compound, wherein the therapeutic amount is effective to increase patient survival; to preserve alloreactivity; to increase the ratio of Treg:alloreactive Teffectors; to reduce tumor burden, to reduce tumor growth, to reduce tumor progression, to reduce tumor proliferation, to increase survival, or a combination thereof.

According to some embodiments of the regimen, the Rho kinase inhibitor compound is telmisartan.

DETAILED DESCRIPTION OF THE INVENTION

Figure 1:
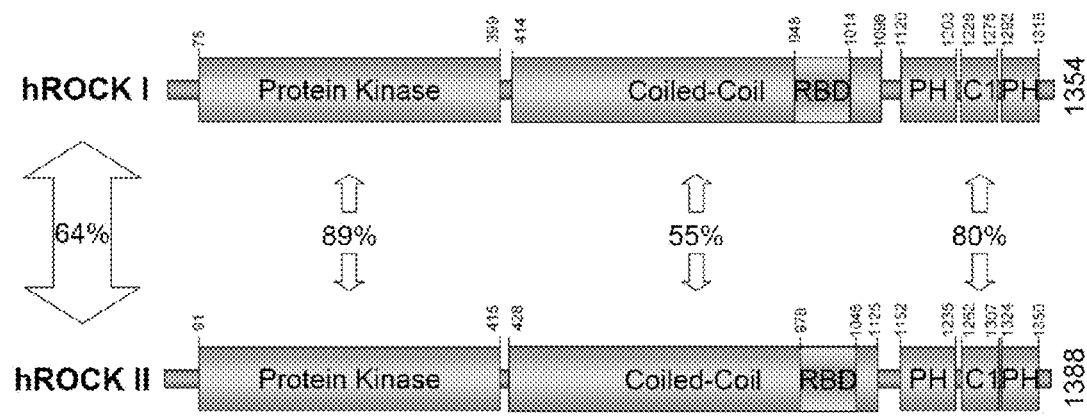
FIG. 1 is a diagram of ROCK functional domains. Common functional domains in human ROCK I and ROCK II with the positions of starting and ending residues as annotated by NCBI. The percentage identities between matched regions were determined by pairwise BLAST comparisons. RBD=Rho Binding Domain. PH=Pleckstrin Homology domain. C1=Protein kinase C conserved region 1. The representations are not to scale. Olson M F, Curr Opin Cell Biol. 20(2): 242-248 (2008).
Figure 2:
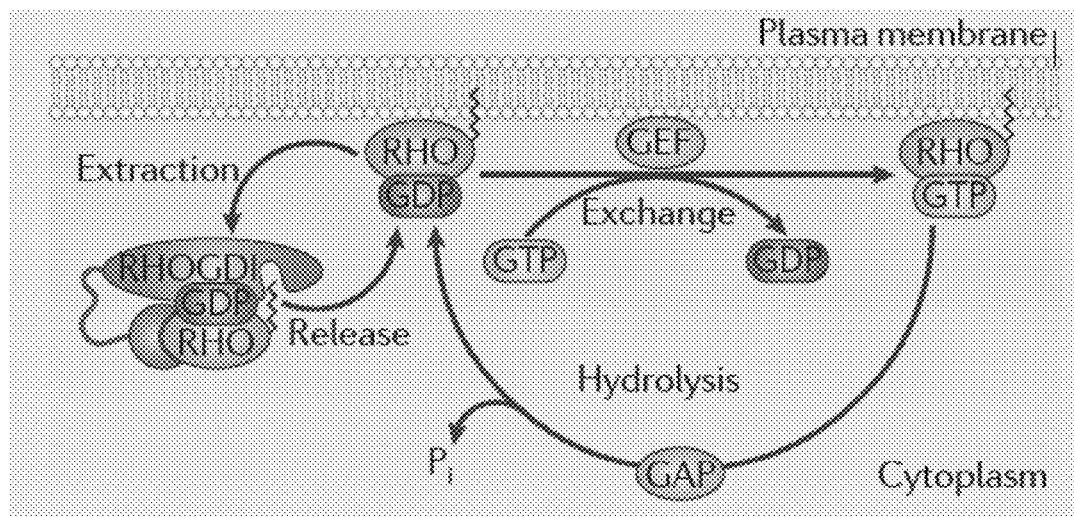
FIG. 2 is a diagram of the Rho switch. ($P_i$=inorganic phosphate).
Figure 3:
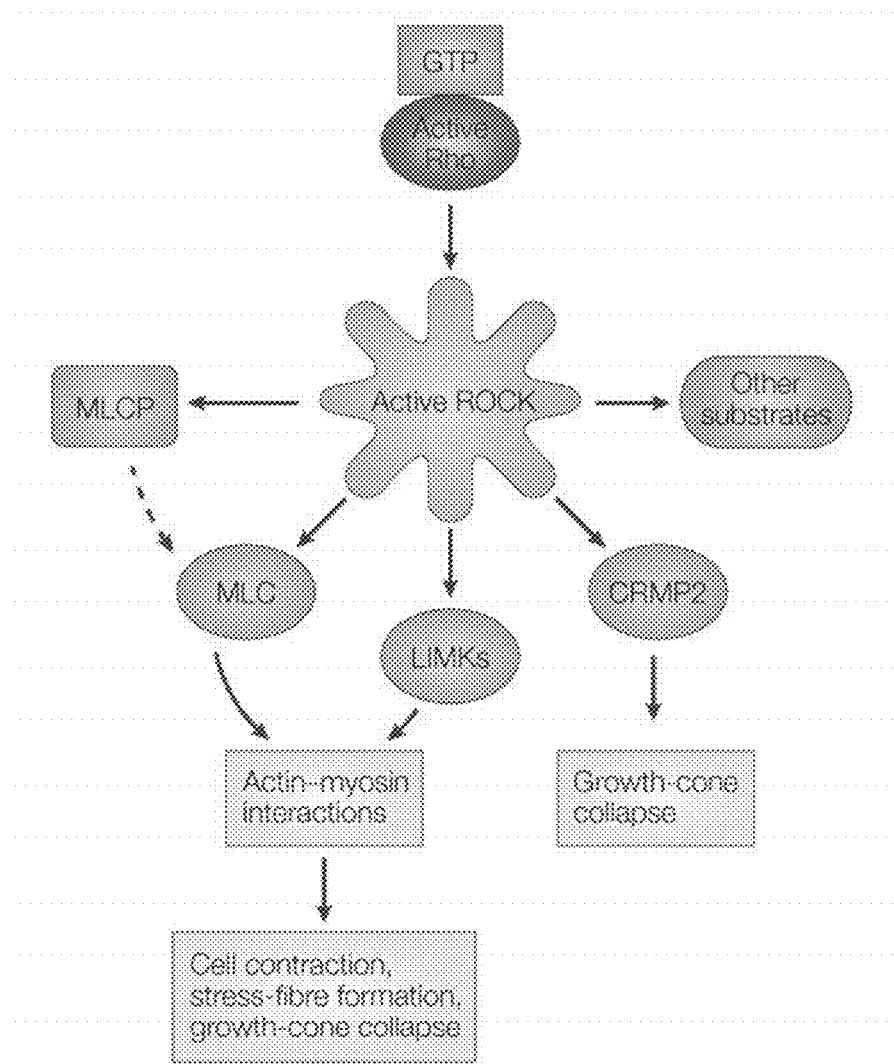
FIG. 3 is a diagram of the upstream and downstream targets of ROCK. Activation of ROCK by GTP-bound Rho leads to phosphorylation of various target proteins, particularly those that regulate actin-myosin contractility. One of the main ROCK substrates is myosin light chain (MLC). Phosphorylation of MLC results in stress-fiber formation and increased cellular contractility. ROCKII also phosphorylates collapsin response mediator protein 2 (CRMP2), a neuronal protein with a role in growth-cone collapse. MLCP, myosin light chain phosphatase; LIMK, LIM kinase.
Figure 4:
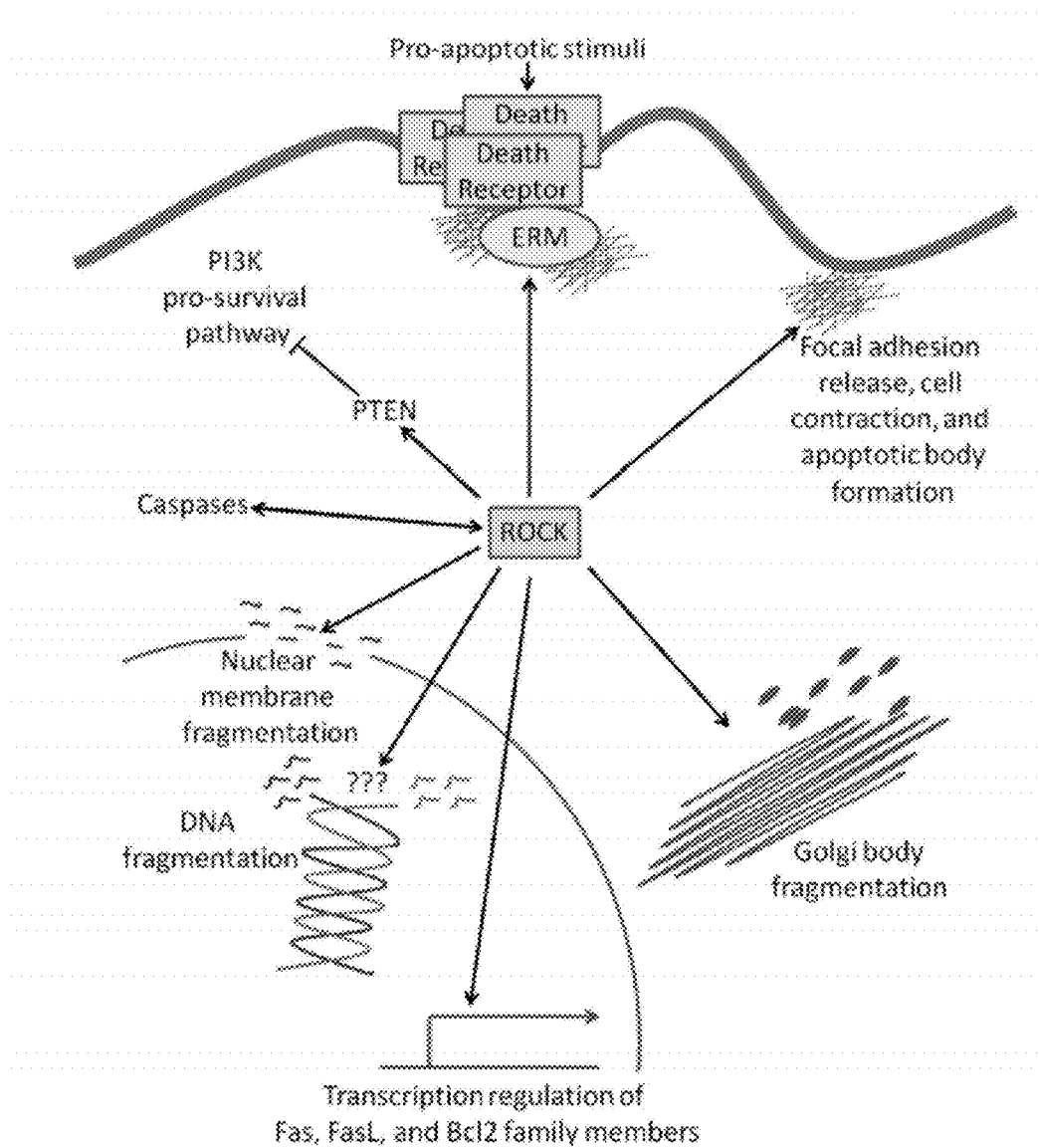
FIG. 4 diagrammatically illustrates ROCK's role in apoptosis. ROCK proteins are activated by caspase cleavage and promote the cleavage of procaspases into their active caspase forms. ROCK activity is necessary for multiple aspects of both intrinsic and extrinsic apoptosis including death receptor activation via ezrin, radixin, and moesin (ERM) proteins, apoptotic bleb and body formation, nuclear and organelle fragmentation, and DNA fragmentation. Moreover, ROCK phosphorylates and inhibits phosphatase and tensin homology (PTEN), thus blocking the pro-survival phosphoinositide 3-kinase (PI3K) pathway.

The described invention can be better understood from the following description of exemplary embodiments, taken in conjunction with the accompanying figures and drawings. It should be apparent to those skilled in the art that the described embodiments provided herein are merely exemplary and illustrative and not limiting.

Potential Benefits

The primary potential benefit of the described invention is reduction in the incidence or severity of acute GVHD, without a diminution in the desired GVTE after allogeneic HSC transplantation. According to some embodiments, administration of a therapeutic amount of a pharmaceutical composition comprising a ROCK inhibitor (i.e., telmisartan) may be effecting to reduce the incidence or severity of acute GVHD, which will result in a decrease in the use of corticosteroids used in the management of acute GVHD, and a resulting decrease in complications of corticosteroid use including immunosuppression, opportunistic viral and fungal infections, steroid myopathy, cataract formation, and avascular necrosis of the bone.

According to some embodiments, the described invention provides a method for attenuating graft-versus-host disease (GVHD) while preserving graft-versus-tumor effect (GVTE) in a patient receiving a transplant comprising administering to the patient a therapeutic amount of a pharmaceutical composition comprising: (i) a Rho kinase (ROCK) inhibitor compound; and (ii) a pharmaceutically acceptable carrier. Transplants include allogeneic or xenogeneic hematopoietic cells, tissue grafts, including solid organs containing lymphoid tissues, and transfusions of unirradiated blood products. According to some embodiments, the GVHD is acute. According to some embodiments, the GVHD is chronic. According to some embodiments, the transplant is a bone marrow transplant. According to some embodiments, the transplant is allogeneic. According to some embodiments, the transplant is xenogeneic. According to some embodiments, the transplant is a vascularized composite allotransplant (VCA). According to some embodiments, the ROCK inhibitor compound is telmisartan. According to some embodiments, the administering to the patient is orally. According to some embodiments, the administering to the patient is parenterally.

According to another aspect, the described invention provides a method for increasing survival of a patient receiving a transplant comprising administering to the patient a therapeutic amount of a pharmaceutical composition comprising: (i) a ROCK inhibitor compound; and (ii) a pharmaceutically acceptable excipient, wherein the therapeutic amount is effective to attenuate GVHD and preserve GVTE in the patient. According to some embodiments, the GVHD is acute. According to some embodiments, the GVHD is chronic. According to some embodiments, the transplant is a bone marrow transplant. According to some embodiments, the transplant is allogeneic. According to some embodiments, the transplant is xenogeneic. According to some embodiments, the transplant is a VCA. According to some embodiments, the ROCK inhibitor compound is telmisartan. According to some embodiments, the administering to the patient is orally. According to some embodiments, the administering to the patient is parenterally.

According to another aspect, the described invention provides a method for preserving alloreactivity in a patient receiving a transplant comprising administering to the patient a therapeutic amount of a pharmaceutical composition comprising: (i) a ROCK inhibitor compound; and (ii) a pharmaceutically acceptable excipient, wherein the therapeutic amount is effective to attenuate GVHD and preserve GVTE in the patient. According some embodiments, the GVHD is acute. According to some embodiments, the GVHD is chronic. According to some embodiments, the transplant is a bone marrow transplant. According some embodiments, the transplant is allogeneic. According to some embodiments, the transplant is xenogeneic. According to some embodiments, the transplant is a VCA. According to some embodiments, the ROCK inhibitor compound is telmisartan. According to some embodiments, the administering to the patient is orally. According to some embodiments, the administering to the patient is parenterally.

According to some embodiments, blocking hypoxia-induced neovascularization with telmisartan or other agents capable of decreasing IT hypoxia and neovascularization may be effective to reduce GVHD while leaving antitumor alloreactivity intact.

According to some embodiments, selective injection of a therapeutic amount of α4β7 Tregs may be beneficial with respect to IT GVHD without suppressing systemic GVTE. According to some embodiments, a therapeutic amount of telmisartan may increase the ratio of Treg:alloreactive Teffectors.

According to some embodiments, a therapeutic amount of telmisartan may be effective to exert an anti-tumor effect. According to some embodiments, the method may be useful to treat nonhematologic solid tumors, e.g., adenomas, blastomas, carcinomas, lymphomas, melanomas, and sarcomas, and other solid tumors in tissues including, but not limited to the brain, breast, colon, kidney, liver, and lung.

According to some embodiments, a therapeutic amount of telmisartan may be effective to improve weight recovery following GVHD-related weight loss in subjects receiving a transplant with donor T cells, relative to control subjects receiving a transplant with donor T cells, but not receiving a therapeutic amount of telmisartan.

According to some embodiments, non-responsive IT GVHD may be correlated with biomarkers, e.g., elafin, IL-8, TNFR1, HGF, reg3a, IL-2RA, or ST2. According to some embodiments, a therapeutic amount of telmisartan may result in the need for less immune suppression in subjects receiving a transplant. According to some embodiments, knowledge gained about the correlations of bio markers with GVHD may permit more efficient and sparing use of potent immuno-suppressive steroids or cytotoxic agents. According to some embodiments, if telmisartan does not suppress GVHD, one or more of our selected markers may exhibit statistical correlation with development of GVHD.

According to some embodiments ROCK inhibition in humans may correlate with telmisartan in vivo biological activity (e.g., lowering of blood pressure), and may also correlate with suppression of GVHD.

Definitions

Various terms used throughout this specification shall have the definitions set out herein.

The term "activation" or "lymphocyte activation" refers to stimulation of lymphocytes by specific antigens, nonspecific mitogens, or allogeneic cells resulting in synthesis of RNA, protein and DNA and production of lymphokines; it is followed by proliferation and differentiation of various effector and memory cells. For example, a mature B cell can be activated by an encounter with an antigen that expresses epitopes that are recognized by its cell surface immunoglobulin Ig). The activation process may be a direct one, dependent on cross-linkage of membrane Ig molecules by the antigen (cross-linkage-dependent B cell activation) or an indirect one, occurring most efficiently in the context of an intimate interaction with a helper T cell ("cognate help process"). T-cell activation is dependent on the interaction of the TCR/CD3 complex with its cognate ligand, a peptide bound in the groove of a class I or class II MHC molecule. The molecular events set in motion by receptor engagement are complex. Among the earliest steps appears to be the activation of tyrosine kinases leading to the tyrosine phosphorylation of a set of substrates that control several signaling pathways. These include a set of adapter proteins that link the TCR to the ras pathway, phospholipase Cγ1, the tyrosine phosphorylation of which increases its catalytic activity and engages the inositol phospholipid metabolic pathway, leading to elevation of intracellular free calcium concentration and activation of protein kinase C, and a series of other enzymes that control cellular growth and differentiation. Full responsiveness of a T cell requires, in addition to receptor engagement, an accessory cell-delivered costimulatory activity, e.g., engagement of CD28 on the T cell by CD80 and/or CD86 on the antigen presenting cell (APC). The soluble product of an activated B lymphocyte is immunoglobulins (antibodies). The soluble product of an activated T lymphocyte is lymphokines.

The term "administering" as used herein includes in vivo administration, as well as administration directly to tissue ex vivo. Generally, compositions can be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired, or can be locally administered by means such as, but not limited to, injection, implantation, grafting, topical application, or parenterally.

The term "allogeneic" as used herein refers to being genetically different although belonging to or obtained from the same species.

The term "alloreactivity" as used herein refers to a strong primary T cell response against allelic variants of major histocompatibility complex (MHD) molecules in a species. Alloreactivity is manifested in the rejection of tissue grafts between individuals of the same species.

The term "allotolerance" as used herein means tolerance towards cells received by allogeneic transplants.

The term "attenuate" as used herein means to reduce the force, effect, or value of.

The term "autoimmune disorder" or "autoimmune syndrome" as used herein refers to a condition that occurs when the immune system mistakenly attacks and destroys self components of healthy body tissue. An autoimmune disorder may affect one or more organ or tissue types. Organs and tissues commonly affected by autoimmune disorders include: blood vessels, connective tissues, endocrine glands such as the thyroid or pancreas, joints, muscles, red blood cells, and skin.

CD3 (TCR complex) is a protein complex composed of four distinct chains. In mammals, the complex contains a CD3γ chain, a CD3δ chain, and two CD3ε chains, which associate with the T cell receptor (TCR) and the ζ-chain to generate an activation signal in T lymphocytes. Together, the TCR, the ζ-chain and CD3 molecules comprise the TCR complex. The intracellular tails of CD3 molecules contain a conserved motif known as the immunoreceptor tyrosine-based activation motif (ITAM), which is essential for the signaling capacity of the TCR. Upon phosphorylation of the ITAM, the CD3 chain can bind ZAP70 (zeta associated protein), a kinase involved in the signaling cascade of the T cell.

The term "chemokine" as used herein refers to a class of chemotactic cytokines that signal leukocytes to move in a specific direction. The terms "chemotaxis" or "chemotactic" refer to the directed motion of a motile cell or part along a chemical concentration gradient towards environmental conditions it deems attractive and/or away from surroundings it finds repellent.

The term "condition", as used herein, refers to a variety of health states and is meant to include disorders or diseases caused by any underlying mechanism or injury.

The term "cytokine" as used herein refers to small soluble protein substances secreted by cells, which have a variety of effects on other cells. Cytokines mediate many important physiological functions, including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins including interleukin 2 (IL-2), as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The term "disease" or "disorder," as used herein, refers to an impairment of health or a condition of abnormal functioning.

The term "drug" as used herein refers to a therapeutic agent or any substance used in the prevention, diagnosis, alleviation, treatment, or cure of disease.

The term "enzymatic activity" as used herein refers to the action of an enzyme (meaning a protein that catalyzes a specific chemical reaction) on its target. It is quantified as the amount of substrate consumed (or product formed) in a given time under given conditions. The term "turnover number" as used herein refers to the number of molecules of substrate that can be converted into product per catalytic site of a given enzyme.

The term "Gem" as used herein refers to a member of the Ras/GTPase superfamily thought to regulate, for example, $Ca^{2+}$ channels, chromosome alignment, spindle length control, mitotic progression and influence cell morphology by antagonizing the actions of ROCK I.

The term "graft" as used herein, refers to any tissue or organ for transplantation. It includes, but is not limited to, a self-tissue transferred from one body site to another in the same individual ("autologous graft"), a tissue transferred between genetically identical individuals or sufficiently immunologically compatible to allow tissue transplant ("syngeneic graft"), a tissue transferred between genetically different members of the same species ("allogeneic graft" or "allograft"), and a tissue transferred between different species ("xenograft").

The term "graft versus host" as used herein, refers to a systemic autoimmune syndrome resulting from cells of an engrafted hematopoietic-cell transplant mounting an immune response against the host. In human recipients of bone marrow, chronic GVHD syndrome is a major clinical problem, leading to fibrosis, pathology and autoantibodies, which can result in immune dysfunction, increased risk of infection, potentially serious impaired organ function, and poor quality of life. The syndrome occurs even in recipients of autologous marrow, although in a milder form. See, e.g. Kennedy M J, Hess A D, Med Oncol. 12(3): 149-156 (1995). Acute GVHD is a clinical syndrome caused by T cell-mediated recognition of minor histocompatibility antigens followed by organ-specific vascular adhesion, migration, proliferation, cytokine release, and direct cell-mediated attack on normal tissues. Chronic GVHD is more complex, incorporating both conventional T-cell effector functions, as well as humoral and antigen-presenting effects of B cells. Antin J H, Blood. 117(23): 6061-6062 (2011).

The term "growth" as used herein refers to a process of becoming larger, longer or more numerous, or an increase in size, number, or volume.

The term "hematopoietic-cell transplantation" (HCT) is used herein to refer to blood and marrow transplantation (BMT), a procedure that involves infusion of cells (hematopoietic stem cells; also called hematopoietic progenitor cells) to reconstitute the hematopoietic system of a patient.

The term "inhibit" and its various grammatical forms, including, but not limited to, "inhibiting" or "inhibition", are used herein to refer to reducing the amount or rate of a process, to stopping the process entirely, or to decreasing, limiting, or blocking the action or function thereof. Inhibition can include a reduction or decrease of the amount, rate, action function, or process of a substance by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%.

The term "inhibitor" as used herein refers to a second molecule that binds to a first molecule thereby decreasing the first molecule's activity. Enzyme inhibitors are molecules that bind to enzymes thereby decreasing enzyme activity. The binding of an inhibitor can stop a substrate from entering the active site of the enzyme and/or hinder the enzyme from catalyzing its reaction. Inhibitor binding is either reversible or irreversible. Irreversible inhibitors usually react with the enzyme and change it chemically, for example, by modifying key amino acid residues needed for enzymatic activity. In contrast, reversible inhibitors bind non-covalently and produce different types of inhibition depending on whether these inhibitors bind the enzyme, the enzyme-substrate complex, or both. Enzyme inhibitors often are evaluated by their specificity and potency.

The term "injury," as used herein, refers to damage or harm to a structure or function of the body caused by an outside agent or force, which can be physical or chemical.

The term "immunomodulatory cell(s)" as used herein refer(s) to cell(s) that are capable of augmenting or diminishing immune responses by expressing chemokines, cytokines and other mediators of immune responses.

The term "inflammatory cytokines" or "inflammatory mediators" as used herein refers to the molecular mediators of the inflammatory process, which may modulate being either pro- or anti-inflammatory in their effect. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, pro-inflammatory cytokines, including, but not limited to, interleukin-1-beta (IL-1β), interleukin-4 (IL-4), interleukin-6 (IL-6), interleukin-8 (IL-8), tumor necrosis factor-alpha (TNF-α), interferon-gamma (IF-γ), and interleukin-12 (IL-12).

The term "interleukin (IL)" as used herein refers to a cytokine secreted by, and acting on, leukocytes. Interleukins regulate cell growth, differentiation, and motility, and stimulates immune responses, such as inflammation. Examples of interleukins include interleukin-1 (IL-1), interleukin 2 (IL-2), interleukin-1β (IL-1β), interleukin-6 (IL-6), interleukin-8 (IL-8), and interleukin-12 (IL-12).

The term "kinase" as used herein refers to a type of enzyme that transfers phosphate groups from high-energy donor molecules to specific target molecules or substrates. High-energy donor groups can include, but are not limited, to GTP and ATP.

The term "Kaplan Meier plot" or "Kaplan Meier survival curve" as used herein refers to the plot of probability of clinical study subjects surviving in a given length of time while considering time in many small intervals. The Kaplan Meier plot assumes that: (i) at any time subjects who are censored (i.e., lost) have the same survival prospects as subjects who continue to be followed; (ii) the survival probabilities are the same for subjects recruited early and late in the study; and (iii) the event (e.g., death) happens at the time specified. Probabilities of occurrence of event are computed at a certain point of time with successive probabilities multiplied by any earlier computed probabilities to get a final estimate. The survival probability at any particular time is calculated as the number of subjects surviving divided by the number of subjects at risk. Subjects who have died, dropped out, or have been censored from the study are not counted as at risk.

The term "lymphocyte" refers to a small white blood cell formed in lymphatic tissue throughout the body and in normal adults making up about 22-28% of the total number of leukocytes in the circulating blood that plays a large role in defending the body against disease. Individual lymphocytes are specialized in that they are committed to respond to a limited set of structurally related antigens. This commitment, which exists before the first contact of the immune system with a given antigen, is expressed by the presence on the lymphocyte's surface membrane of receptors specific for determinants (epitopes) on the antigen. Each lymphocyte possesses a population of receptors, all of which have identical combining sites. One set, or clone, of lymphocytes differs from another clone in the structure of the combining region of its receptors and thus differs in the epitopes that it can recognize. Lymphocytes differ from each other not only in the specificity of their receptors, but also in their functions.

Two broad classes of lymphocytes are recognized: the B-lymphocytes (B-cells), which are precursors of antibody-secreting cells, and T-lymphocytes (T-cells).

B-Lymphocytes

B-lymphocytes are derived from hematopoietic cells of the bone marrow. A mature B-cell can be activated with an antigen that expresses epitopes that are recognized by its cell surface. The activation process may be direct, dependent on cross-linkage of membrane Ig molecules by the antigen (cross-linkage-dependent B-cell activation), or indirect, via interaction with a helper T-cell, in a process referred to as cognate help. In many physiological situations, receptor cross-linkage stimuli and cognate help synergize to yield more vigorous B-cell responses. Paul W E, "Chapter 1: The immune system: an introduction." Fundamental Immunology, 4$^{th}$ Edition, Lippincott-Raven Publishers, Philadelphia (1999).

Cross-linkage dependent B-cell activation requires that the antigen express multiple copies of the epitope complementary to the binding site of the cell surface receptors because each B-cell expresses Ig molecules with identical variable regions. Such a requirement is fulfilled by other antigens with repetitive epitopes, such as capsular polysaccharides of microorganisms or viral envelope proteins. Cross-linkage-dependent B-cell activation is a major protective immune response mounted against these microbes. Paul W E, "Chapter 1: The immune system: an introduction." Fundamental Immunology, 4$^{th}$ Edition, Lippincott-Raven Publishers, Philadelphia (1999).

Cognate help allows B-cells to mount responses against antigens that cannot cross-link receptors and, at the same time, provides costimulatory signals that rescue B cells from inactivation when they are stimulated by weak cross-linkage events. Cognate help is dependent on the binding of antigen by the B-cell's membrane immunoglobulin (Ig), the endocytosis of the antigen, and its fragmentation into peptides within the endosomal/lysosomal compartment of the cell. Some of the resultant peptides are loaded into a groove in a specialized set of cell surface proteins known as class II major histocompatibility complex (MHC) molecules. The resultant class II/peptide complexes are expressed on the cell surface and act as ligands for the antigen-specific receptors of a set of T-cells designated as CD4+ T-cells. The CD4+ T-cells bear receptors on their surface specific for the B-cell's class II/peptide complex. B-cell activation depends not only on the binding of the T cell through its T cell receptor (TCR), but this interaction also allows an activation ligand on the T-cell (CD40 ligand) to bind to its receptor on the B-cell (CD40) signaling B-cell activation. In addition, T helper cells secrete several cytokines that regulate the growth and differentiation of the stimulated B-cell by binding to cytokine receptors on the B cell. Paul W E, "Chapter 1: The immune system: an introduction." Fundamental Immunology, 4$^{th}$ Edition, Lippincott-Raven Publishers, Philadelphia (1999).

During cognate help for antibody production, the CD40 ligand is transiently expressed on activated CD4+ T helper cells, and it binds to CD40 on the antigen-specific B cells, thereby transducing a second costimulatory signal. The latter signal is essential for B cell growth and differentiation and for the generation of memory B cells by preventing apoptosis of germinal center B cells that have encountered antigen. Hyperexpression of the CD40 ligand in both B and T cells is implicated in the pathogenic autoantibody production in human SLE patients. Desai-Mehta A, et al., J Clin Invest. 97(9): 2063-2073 (1996).

T-Lymphocytes

T-lymphocytes derive from precursors in hematopoietic tissue, undergo differentiation in the thymus, and are then seeded to peripheral lymphoid tissue and to the recirculating pool of lymphocytes. T-lymphocytes or T cells mediate a wide range of immunologic functions. These include the capacity to help B cells develop into antibody-producing cells, the capacity to increase the microbicidal action of monocytes/macrophages, the inhibition of certain types of immune responses, direct killing of target cells, and mobilization of the inflammatory response. These effects depend on their expression of specific cell surface molecules and the secretion of cytokines. Paul W E, "Chapter 1: The immune system: an introduction." Fundamental Immunology, $4^{th}$ Edition, Lippincott-Raven Publishers, Philadelphia (1999).

T cells differ from B cells in their mechanism of antigen recognition. Immunoglobulin, the B cell's receptor, binds to individual epitopes on soluble molecules or on particulate surfaces. B-cell receptors see epitopes expressed on the surface of native molecules. Antibody and B-cell receptors evolved to bind to and to protect against microorganisms in extracellular fluids. In contrast, T cells recognize antigens on the surface of other cells and mediate their functions by interacting with, and altering, the behavior of these antigen-presenting cells (APCs). There are three main types of antigen-presenting cells in peripheral lymphoid organs that can activate T cells: dendritic cells, macrophages and B cells. The most potent of these are the dendritic cells, whose only function is to present foreign antigens to T cells. Immature dendritic cells are located in tissues throughout the body, including the skin, gut, and respiratory tract. When they encounter invading microbes at these sites, they endocytose the pathogens and their products, and carry them via the lymph to local lymph nodes or gut associated lymphoid organs. The encounter with a pathogen induces the dendritic cell to mature from an antigen-capturing cell to an antigen-presenting cell (APC) that can activate T cells. APCs display three types of protein molecules on their surface that have a role in activating a T cell to become an effector cell: (1) MHC proteins, which present foreign antigen to the T cell receptor; (2) costimulatory proteins which bind to complementary receptors on the T cell surface; and (3) cell-cell adhesion molecules, which enable a T cell to bind to the antigen-presenting cell (APC) for long enough to become activated. Alberts B, et al. "Chapter 24: The adaptive immune system." Molecular Biology of the Cell, 4th Edition, Garland Science, New York (2002).

T-cells are subdivided into two distinct classes based on the cell surface receptors they express. The majority of T cells express T cell receptors (TCR) consisting of α and β chains. A small group of T cells express receptors made of γ and δ chains. Among the α/β T cells are two important sublineages: those that express the coreceptor molecule CD4 (CD4+ T cells); and those that express CD8 (CD8+ T cells). These cells differ in how they recognize antigen and in their effector and regulatory functions.

CD4+ T cells are the major regulatory cells of the immune system. Their regulatory function depends both on the expression of their cell-surface molecules, such as CD40 ligand whose expression is induced when the T cells are activated, and the wide array of cytokines they secrete when activated.

T cells also mediate important effector functions, some of which are determined by the patterns of cytokines they secrete. The cytokines can be directly toxic to target cells and can mobilize potent inflammatory mechanisms.

In addition, T cells particularly CD8+ T cells, can develop into cytotoxic T-lymphocytes (CTLs) capable of efficiently lysing target cells that express antigens recognized by the CTLs. Paul W E, "Chapter 1: The immune system: an introduction." Fundamental Immunology, $4^{th}$ Edition, Lippincott-Raven Publishers, Philadelphia (1999).

T cell receptors (TCRs) recognize a complex consisting of a peptide derived by proteolysis of the antigen bound to a specialized groove of a class II or class I MHC protein. The CD4+ T cells recognize only peptide/class II complexes while the CD8+ T cells recognize peptide/class I complexes. Paul W E, "Chapter 1: The immune system: an introduction." Fundamental Immunology, $4^{th}$ Edition, Lippincott-Raven Publishers, Philadelphia (1999).

The TCR's ligand (i.e., the peptide/MHC protein complex) is created within antigen-presenting cells (APCs). In general, class II MHC molecules bind peptides derived from proteins that have been taken up by the APC through an endocytic process. These peptide-loaded class II molecules are then expressed on the surface of the cell, where they are available to be bound by CD4+ T cells with TCRs capable of recognizing the expressed cell surface complex. Thus, CD4+ T cells are specialized to react with antigens derived from extracellular sources. Paul W E, "Chapter 1: The immune system: an introduction." Fundamental Immunology, $4^{th}$ Edition, Lippincott-Raven Publishers, Philadelphia (1999).

In contrast, class I MHC molecules are mainly loaded with peptides derived from internally synthesized proteins, such as viral proteins. These peptides are produced from cytosolic proteins by proteolysis by the proteosome and are translocated into the rough endoplasmic reticulum. Such peptides, generally nine amino acids in length, are bound into the class I MHC molecules and are brought to the cell surface, where they can be recognized by CD8+ T cells expressing appropriate receptors. This gives the T cell system, particularly CD8+ T cells, the ability to detect cells expressing proteins that are different from, or produced in much larger amounts than, those of cells of the remainder of the organism (e.g., vial antigens) or mutant antigens (such as active oncogene products), even if these proteins in their intact form are neither expressed on the cell surface nor secreted. Paul W E, "Chapter 1: The immune system: an introduction." Fundamental Immunology, $4^{th}$ Edition, Lippincott-Raven Publishers, Philadelphia (1999).

T cells can also be classified based on their function as helper T cells; T cells involved in inducing cellular immunity; suppressor T cells; and cytotoxic T cells.

Helper T Cells

Helper T cells are T cells that stimulate B cells to make antibody responses to proteins and other T cell-dependent antigens. T cell-dependent antigens are immunogens in which individual epitopes appear only once or a limited number of times such that they are unable to cross-link the membrane immunoglobulin (Ig) of B cells or do so inefficiently. B cells bind the antigen through their membrane Ig, and the complex undergoes endocytosis. Within the endosomal and lysosomal compartments, the antigen is fragmented into peptides by proteolytic enzymes and one or more of the generated peptides are loaded into class II MHC molecules, which traffic through this vesicular compartment. The resulting peptide/class II MHC complex is then exported to the B-cell surface membrane. T cells with receptors specific for the peptide/class II molecular complex recognize this complex on the B-cell surface. Paul W E, "Chapter 1: The immune system: an introduction." Fundamental Immunology, 4$^{th}$ Edition, Lippincott-Raven Publishers, Philadelphia (1999).

B-cell activation depends both on the binding of the T cell through its TCR and on the interaction of the T-cell CD40 ligand (CD40L) with CD40 on the B cell. T cells do not constitutively express CD40L. Rather, CD40L expression is induced as a result of an interaction with an APC that expresses both a cognate antigen recognized by the TCR of the T cell and CD80 or CD86. CD80/CD86 is generally expressed by activated, but not resting, B cells so that the helper interaction involving an activated B cell and a T cell can lead to efficient antibody production. In many cases, however, the initial induction of CD40L on T cells is dependent on their recognition of antigen on the surface of APCs that constitutively express CD80/86, such as dendritic cells. Such activated helper T cells can then efficiently interact with and help B cells. Cross-linkage of membrane Ig on the B cell, even if inefficient, may synergize with the CD40L/CD40 interaction to yield vigorous B-cell activation. The subsequent events in the B-cell response, including proliferation, Ig secretion, and class switching (of the Ig class being expressed) either depend or are enhanced by the actions of T cell-derived cytokines. Paul W E, "Chapter 1: The immune system: an introduction." Fundamental Immunology, 4$^{th}$ Edition, Lippincott-Raven Publishers, Philadelphia (1999).

CD4+ T cells tend to differentiate into cells that principally secrete the cytokines IL-4, IL-5, IL-6, and IL-10 ($T_{H2}$ cells) or into cells that mainly produce IL-2, IFN-γ, and lymphotoxin ($T_{H1}$ cells). The $T_{H2}$ cells are very effective in helping B-cells develop into antibody-producing cells, whereas the $T_{H1}$ cells are effective inducers of cellular immune responses, involving enhancement of microbicidal activity of monocytes and macrophages, and consequent increased efficiency in lysing microorganisms in intracellular vesicular compartments. Although the CD4+ T cells with the phenotype of $T_{H2}$ cells (i.e., IL-4, IL-5, IL-6 and IL-10) are efficient helper cells, $T_{H1}$ cells also have the capacity to be helpers. Paul W E, "Chapter 1: The immune system: an introduction." Fundamental Immunology, 4$^{th}$ Edition, Lippincott-Raven Publishers, Philadelphia (1999).

T Cells Involved in Induction of Cellular Immunity

T cells also may act to enhance the capacity of monocytes and macrophages to destroy intracellular microorganisms. In particular, interferon-gamma (IFN-γ) produced by helper T cells enhances several mechanisms through which mononuclear phagocytes destroy intracellular bacteria and parasitism including the generation of nitric oxide and induction of tumor necrosis factor (TNF) production. The $T_{H1}$ cells are effective in enhancing the microbicidal action because they produce IFN-γ. By contrast, two of the major cytokines produced by $T_{H2}$ cells, IL-4 and IL-10, block these activities. Paul W E, "Chapter 1: The immune system: an introduction." Fundamental Immunology, 4$^{th}$ Edition, Lippincott-Raven Publishers, Philadelphia (1999).

Suppressor or Regulatory T (Treg) Cells

A controlled balance between initiation and downregulation of the immune response is important to maintain immune homeostasis. Both apoptosis and T cell anergy (a tolerance mechanism in which the T cells are intrinsically functionally inactivated following an antigen encounter) (Schwartz, R H, Annu Rev Immunol. 21: 305-334 (2003)) are important mechanisms that contribute to the downregulation of the immune response. A third mechanism is provided by active suppression of activated T cells by suppressor or regulatory CD4+ T (Treg) cells. Kronenberg, M, Rudensky A, Nature. 435(7042): 598-604 (2005). CD4+ Tregs that constitutively express the IL-2 receptor alpha (IL-2Rα) chain (CD4+CD25+) are a naturally occurring T cell subset that are anergic and suppressive. Taams L S, et al., Eur J Immunol. 31(4): 1122-1131 (2001). Depletion of CD4$^+$CD25$^+$ Tregs results in systemic autoimmune disease in mice. Furthermore, transfer of these Tregs prevents development of autoimmune disease. Human CD4$^+$CD25$^+$ Tregs, similar to their murine counterpart, are generated in the thymus and are characterized by the ability to suppress proliferation of responder T cells through a cell-cell contact-dependent mechanism, the inability to produce IL-2, and the anergic phenotype in vitro. Human CD4$^+$CD25$^+$ T cells can be split into suppressive (CD25$^{high}$) and nonsuppressive (CD25$^{low}$) cells, according to the level of CD25 expression. A member of the forkhead family of transcription factors, FOXP3, has been shown to be expressed in murine and human CD4$^+$CD25$^+$ Tregs and appears to be a master gene controlling CD4$^+$CD25$^+$ Treg development. Battaglia M, et al., J Immunol. 177(12): 8338-8347 (2006).

Cytotoxic T Lymphocytes (CTL)

The CD8+ T cells that recognize peptides from proteins produced within the target cell have cytotoxic properties in that they lead to lysis of the target cells. The mechanism of CTL-induced lysis involves the production by the CTL of perforin, a molecule that can insert into the membrane of target cells and promote the lysis of that cell. Perforin-mediated lysis is enhanced by a series of enzymes produced by activated CTLs, referred to as granzymes. Many active CTLs also express large amounts of fas ligand on their surface. The interaction of fas ligand on the surface of CTL with fas on the surface of the target cell initiates apoptosis in the target cell, leading to the death of these cells. CTL-mediated lysis appears to be a major mechanism for the destruction of virally infected cells.

The term "modify" as used herein means to change, vary, adjust, temper, alter, affect or regulate to a certain measure or proportion in one or more particulars.

The term "modulate" as used herein means to regulate, alter, adapt, or adjust to a certain measure or proportion.

The term "monitor" is used herein to refer to observing, recording, detecting, watching for purposes of control, keeping track of, or checking continually.

As used herein, the terms "oral" or "orally" refer to the introduction into the body by mouth whereby absorption occurs in one or more of the following areas of the body: the mouth, stomach, small intestine, lungs (also specifically referred to as inhalation), and the small blood vessels under the tongue (also specifically referred to as sublingually). The term "pharmaceutical composition" as used herein refers to a preparation comprising a pharmaceutical product, drug, metabolite, or active ingredient.

The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord), or infusion techniques. A parenterally administered composition of the described invention is delivered using a needle, e.g., a surgical needle. The term "surgical needle" as used herein, refers to any needle adapted for delivery of fluid (i.e., capable of flow) compositions of the described invention into a selected anatomical structure. Injectable preparations, such as sterile injectable aqueous or oleaginous suspensions, can be formulated according to the known art using suitable dispersing or wetting agents and suspending agents.

The term "predict" as used herein refers to being able to foretell with precision of calculation, knowledge, or inference from facts or experience.

The term "preserve" as used herein refers to keeping up, maintaining, sustaining, or conserving.

Priming

The term "unprimed cells" (also referred to as virgin, naïve, or inexperienced cells) as used herein refers to T cells and B cells that have generated an antigen receptor (TCR for T cells, BCR for B cells) of a particular specificity, but have never encountered the antigen. The term "priming" as used herein refers to the process whereby T cells and B cell precursors encounter the antigen for which they are specific.

For example, before helper T cells and B cells can interact to produce specific antibody, the antigen-specific T cell precursors must be primed. Priming involves several steps: antigen uptake, processing, and cell surface expression bound to class II MHC molecules by an antigen presenting cell, recirculation and antigen-specific trapping of helper T cell precursors in lymphoid tissue, and T cell proliferation and differentiation. Janeway, C A Jr., Semin Immunol. 1(1): 13-20 (1989). Helper T cells express CD4, but not all CD4 T cells are helper cells. Janeway, C A Jr., Semin Immunol. 1(1): 13-20 (1989). The signals required for clonal expansion of helper T cells differ from those required by other CD4 T cells. The critical antigen-presenting cell for helper T cell priming appears to be a macrophage; and the critical second signal for helper T cell growth is the macrophage product interleukin 1 (IL-1). Janeway, C A Jr., Semin Immunol. 1(1): 13-20 (1989). If the primed T cells and/or B cells receive a second, costimulatory signal, they become activated T cells or B cells.

The term "progression" as used herein refers to the course of a disease as it becomes worse or spreads in the body.

The term "progression-free survival" (PFS) as used herein refers to the length of time during and after the treatment of a disease that a patient lives with the disease but it does not get worse.

The term "proliferation" as used herein refers to expansion of a population of cells by the continuous division of single cells into identical daughter cells, leading to a multiplying or increasing in the number of cells.

The term "RAD" or "ras-related protein associated with diabetes" as used herein refers to a member of the Ras/GTPase superfamily that is highly expressed in heart, lung and skeletal muscle. RAD overexpression is believed to attenuate insulin-stimulated glucose uptake without altering expression or insulin-stimulated translocation of the Glut4 glucose transporter. Rad has been shown to interact with skeletal muscle β-tropomyosin, suggesting that RAD may participate in regulation of the cytoskeleton. Rad has been shown to inhibit Rho associated coil-coil kinase.

"Rectal" or "rectally" as used herein refers to introduction into the body through the rectum where absorption occurs through the walls of the rectum.

The term "reduce" or "reducing" as used herein refers to the limiting of an occurrence of a disorder in individuals at risk of developing the disorder.

The term "regimen" is used herein to refer to a regulated course of treatment intended to preserve or restore health or to attain a result.

The term "Rho" as used herein refers to a subfamily of proteins related to the RAS subgroup thought to be involved in cell transformation and the regulation of morphology and function of dendritic cells. Non-limiting examples of Rho proteins include RhoA, RhoB and RhoC, RhoG, RhoH, RhoQ, RhoU RhoV, Rnd1, 2 and 3 (e.g., RhoE), and RAC1, 2, 3 and 4.

The term "RhoE" (also known as "Rnd3") as used herein refers to a member of the Rnd subgroup of the Rho family of GTPases that appears to act as a negative regulator of cytoskeletal organization leading to loss of adhesion.

The term "ROCK" as used herein refers to Rho associated coil-coil kinase. There are two ROCK proteins, ROCK I and ROCK II. The GeneBank accession number for human ROCK I is EF445027.1. The GeneBank accession number for human ROCK II is NP_004841.

The term "ROCK inhibitor" as used herein refers to any molecule that decreases the function of a ROCK protein.

The term "stimulate" in any of its grammatical forms as used herein refers to inducing activation or increasing activity.

As used herein, the terms "subject" or "individual" or "patient" are used interchangeably to refer to a member of an animal species of mammalian origin, including humans. The term "a subject in need thereof" is used to refer to a subject having, or at risk of having a GVHD disease, disorder or condition.

The term "symptom" as used herein refers to a phenomenon that arises from and accompanies a particular disease or disorder and serves as an indication of it.

The term "syndrome," as used herein, refers to a pattern of symptoms indicative of some disease or condition.

The term "therapeutic agent" as used herein refers to a drug, molecule, nucleic acid, protein, metabolite, composition or other substance that provides a therapeutic effect. The term "active" as used herein refers to the ingredient, component or constituent of the compositions of the described invention responsible for the intended therapeutic effect. The terms "therapeutic agent" and "active agent" are used interchangeably herein. The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50 which describes the dose in a particular dosage that is therapeutically effective for a particular disease manifestation in 50% of a population.

The terms "therapeutic amount", "therapeutically effective amount", an "amount effective", or "pharmaceutically effective amount" of an active agent is used interchangeably to refer to an amount that is sufficient to provide the intended benefit of treatment. According to some embodiments, an effective amount of the active agent(s) that can be employed according to the described invention generally ranges from about 0.10 mg/m$^2$ body surface area to about 0.49 mg/m$^2$ body surface area per dose, administered daily. According to some embodiments, an effective amount of the active agent(s) that can be employed according to the described invention generally ranges from about 0.50 mg/m$^2$ body surface area to about 0.99 mg/m$^2$ body surface area per dose, administered daily. According to some embodiments, an effective amount of the active agent(s) that can be employed according to the described invention generally ranges from about 1.00 mg/m$^2$ body surface area to about 2.00 mg/m$^2$ body surface area per dose, administered daily. According to some embodiments, an effective amount of the active agent(s) that can be employed according to the described invention generally ranges from about 2.01 mg/m² body surface area to about 5.00 mg/m² body surface area per dose, administered daily. According to some embodiments, an effective amount of the active agent(s) that can be employed according to the described invention generally ranges from about 5.01 mg/m² body surface area to about 10.00 mg/m² body surface area per dose, administered daily. According to some embodiments, an effective amount of the active agent(s) that can be employed according to the described invention generally ranges from about 10.01 mg/m² body surface area to about 20.00 mg/m² body surface area per dose, administered daily. According to some embodiments, an effective amount of the active agent(s) that can be employed according to the described invention generally ranges from about 20.01 mg/m² body surface area to about 40.00 mg/m² body surface area per dose, with administered daily. According to some embodiments, an effective amount of the active agent(s) that can be employed according to the described invention generally ranges from about 40.01 mg/m² body surface area to about 60.00 mg/m² body surface area per dose, administered daily. According to some embodiments, an effective amount of the active agent(s) that can be employed according to the described invention generally ranges from about 60.01 mg/m² body surface area to about 80.00 mg/m² body surface area per dose, administered daily. According to some embodiments, an effective amount of the active agent(s) that can be employed according to the described invention generally ranges from about 80.01 mg/m² body surface area to about 100.00 mg/m² body surface area per dose, administered daily. According to some embodiments, an effective amount of the active agent(s) that can be employed according to the described invention generally ranges from about 100.01 mg/m² body surface area to about 120.00 mg/m² body surface area per dose, administered daily. According to some embodiments, an effective amount of the active agent(s) that can be employed according to the described invention generally ranges from about 120.01 mg/m² body surface area to about 140.00 mg/m² body surface area per dose, administered daily. According to some embodiments, an effective amount of the active agent(s) that can be employed according to the described invention generally ranges from about 140.01 mg/m² body surface area to about 160.00 mg/m² body surface area per dose, administered daily. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods. Additionally, the terms "therapeutic amount", "therapeutically effective amount" and "pharmaceutically effective amount" includes prophylactic or preventative amounts of the compositions of the described invention. In prophylactic or preventative applications of the described invention, pharmaceutical compositions or medicaments are administered to a patient susceptible to, or otherwise at risk of, a disease, disorder or condition in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition. It is generally preferred that a maximum dose be used, that is, the highest safe dose according to some medical judgment. The terms "dose" and "dosage" are used interchangeably herein.

The term "therapeutic effect" as used herein refers to a consequence of treatment, the results of which are judged to be desirable and beneficial. A therapeutic effect can include, directly or indirectly, the arrest, reduction, or elimination of a disease manifestation. A therapeutic effect can also include, directly or indirectly, the arrest reduction or elimination of the progression of a disease manifestation.

For any therapeutic agent described herein the therapeutically effective amount may be initially determined from preliminary in vitro studies and/or animal models. A therapeutically effective dose may also be determined from human data. The applied dose may be adjusted based on the relative bioavailability and potency of the administered compound. Adjusting the dose to achieve maximal efficacy based on the methods described above and other well-known methods is within the capabilities of the ordinarily skilled artisan.

General principles for determining therapeutic effectiveness, which may be found in Chapter 1 of Goodman and Gilman's The Pharmacological Basis of Therapeutics, 10th Edition, McGraw-Hill, New York (2001), incorporated herein by reference, are summarized below.

Pharmacokinetic principles provide a basis for modifying a dosage regimen to obtain a desired degree of therapeutic efficacy with a minimum of unacceptable adverse effects. In situations where the drug's plasma concentration can be measured and related to the therapeutic window, additional guidance for dosage modification can be obtained.

Drug products are considered to be pharmaceutical equivalents if they contain the same active ingredients and are identical in strength or concentration, dosage form, and route of administration. Two pharmaceutically equivalent drug products are considered to be bioequivalent when the rates and extents of bioavailability of the active ingredient in the two products are not significantly different under suitable test conditions.

The term "therapeutic window" refers to a concentration range that provides therapeutic efficacy without unacceptable toxicity. Following administration of a dose of a drug, its effects usually show a characteristic temporal pattern. A lag period is present before the drug concentration exceeds the minimum effective concentration ("MEC") for the desired effect. Following onset of the response, the intensity of the effect increases as the drug continues to be absorbed and distributed. This reaches a peak, after which drug elimination results in a decline in the effect's intensity that disappears when the drug concentration falls back below the MEC. Accordingly, the duration of a drug's action is determined by the time period over which concentrations exceed the MEC. The therapeutic goal is to obtain and maintain concentrations within the therapeutic window for the desired response with a minimum of toxicity. Drug response below the MEC for the desired effect will be subtherapeutic, whereas for an adverse effect, the probability of toxicity will increase above the MEC. Increasing or decreasing drug dosage shifts the response curve up or down the intensity scale and is used to modulate the drug's effect. Increasing the dose also prolongs a drug's duration of action but at the risk of increasing the likelihood of adverse effects. Accordingly, unless the drug is nontoxic, increasing the dose is not a useful strategy for extending a drug's duration of action.

Instead, another dose of drug should be given to maintain concentrations within the therapeutic window. In general, the lower limit of the therapeutic range of a drug appears to be approximately equal to the drug concentration that produces about half of the greatest possible therapeutic effect, and the upper limit of the therapeutic range is such that no more than about 5% to about 10% of patients will experience a toxic effect. These figures can be highly variable, and some patients may benefit greatly from drug concentrations that exceed the therapeutic range, while others may suffer significant toxicity at much lower values. The therapeutic goal is to maintain steady-state drug levels within the therapeutic window. For most drugs, the actual concentrations associated with this desired range are not and need not be known, and it is sufficient to understand that efficacy and toxicity are generally concentration-dependent, and how drug dosage and frequency of administration affect the drug level. For a small number of drugs where there is a small (two- to three-fold) difference between concentrations resulting in efficacy and toxicity, a plasma-concentration range associated with effective therapy has been defined.

In this case, a target level strategy is reasonable, wherein a desired target steady-state concentration of the drug (usually in plasma) associated with efficacy and minimal toxicity is chosen, and a dosage is computed that is expected to achieve this value. Drug concentrations subsequently are measured and dosage is adjusted if necessary to approximate the target more closely.

In most clinical situations, drugs are administered in a series of repetitive doses or as a continuous infusion to maintain a steady-state concentration of drug associated with the therapeutic window. To maintain the chosen steady-state or target concentration ("maintenance dose"), the rate of drug administration is adjusted such that the rate of input equals the rate of loss. If the clinician chooses the desired concentration of drug in plasma and knows the clearance and bioavailability for that drug in a particular patient, the appropriate dose and dosing interval can be calculated.

The term "topical" refers to administration of a composition at, or immediately beneath, the point of application. The phrase "topically applying" describes application onto one or more surfaces(s) including epithelial surfaces. Although topical administration, in contrast to transdermal administration, generally provides a local rather than a systemic effect, as used herein, unless otherwise stated or implied, the terms topical administration and transdermal administration are used interchangeably.

The term "transplantation" as used herein, refers to removal and transfer of cells, a tissue or an organ from one part or individual to another.

As used herein the term "treating" includes abrogating, substantially inhibiting, slowing or reversing the progression of a condition, substantially ameliorating clinical symptoms of a condition, or substantially preventing the appearance of clinical symptoms of a condition. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "tumor" as used herein refers to a diseases involving abnormal cell growth in numbers (proliferation) or in size with the potential to invade or spread to other parts of the body (metastasis).

The term "tumor burden" or "tumor load" are used interchangeably herein refers to the number of cancer cells, the size of a tumor, or the amount of cancer in the body.

The terms "vascularized composite allotransplant", "VCA", "composite tissue allograft", and "CTA" are used interchangeably herein to refer to the transplantation of several tissue types, including but not limited to, integumentary, musculoskeletal, cutaneous, and hematopoietic elements, in a patient with severe tissue defects and/or disfigurements such as disfiguring facial injuries, extremity amputations and other composite tissue defects. As used herein, the term "composite" refers to multiple tissue types essential for function. Non-limiting examples of multiple tissue types include skin, muscle, nerves and blood vessels.

Administration

According to some embodiments, the described invention provides a therapeutic amount of one or more ROCK inhibitor compounds as an active ingredient of a pharmaceutical composition. ROCK inhibitor compounds include, but are not limited to, telmisartan (Micardis®, Boehringer Ingelheim), HA-1077 (Fasudil®, Asahi-Kasei Pharmaceuticals, Inc.), Y-27632, Y-39983 and Wf-536 (Mitsubishi Pharmaceuticals), SLx-2119 (Surface Loix, Inc.), Azabenzimidazole-aminofurazans (GlaxoSmithKline), DE-104 (Santen Pharmaceuticals), H-1152P (Kowa Pharmaceuticals), XD-4000 (Xcellsyz, Ltd), HMN-1152 (Nagoya University), 4-(1-aminoalkyl)-N-(4-pyridyl) cyclohexane-carboxamide, BA-210, BA-207, BA-215, BA-285, BA-1037 (BioAxone Therapeutics), Ki-23095 (Kirin Brewery Co.), VAS-012 (VasGene Therapeutics), quinazoline (Bayer AG) and the like.

According to some embodiments, the step of administering comprises administering the composition orally, topically, parenterally, buccally, sublingually, by inhalation, or rectally. According to some embodiments, the administering step comprises administering the composition orally. According to some embodiments, the administering step comprises administering the composition topically. According to some embodiments, the administering step comprises administering the composition parenterally. According to some embodiments, the administering step comprises administering the composition buccally. According to some embodiments, the administering step comprises administering the composition sublingually. According to some embodiments, the administering step comprises administering the composition by inhalation. According to some embodiments, the administering step comprises administering the composition rectally.

According to some embodiments, the composition is in the form of a tablet, a pill, a gel, an injectable solution, an aerosol, a troche, a lozenge, an aqueous suspension, an oily suspension, a dispersible powder, a granule, a bead, an emulsion, an implant, a cream, a patch, a capsule, a syrup, a suppository or an insert. According to some embodiments, the composition is in the form of a tablet. According to some embodiments, the composition is in the form of a pill. According to some embodiments, the composition is in the form of a gel. According to some embodiments, the composition is in the form of an injectable solution. According to some embodiments, the composition is in the form of an aerosol. According to some embodiments, the composition is in the form of a troche. According to some embodiments, the composition is in the form of a lozenge. According to some embodiments, the composition is in the form of an aqueous suspension. According to some embodiments, the composition is in the form an oily suspension. According to some embodiments, the composition is in the form of a dispersible powder. According to some embodiments, the composition is in the form of a granule. According to some embodiments, the composition is in the form of a bead.

According to some embodiments, the composition is in the form of an emulsion. According to some embodiments, the composition is in the form of an implant. According to some embodiments, the composition is in the form of a cream. According to some embodiments, the composition is in the form of a patch. According to some embodiments, the composition is in the form of a capsule. According to some embodiments, the composition is in the form of a syrup. According to some embodiments, the composition is in the form of a suppository. According to some embodiments, the composition is in the form of an insert.

The compositions of the described invention can be administered orally, topically, parenterally, buccally, sublingually, by inhalation or insufflation (either through the mouth or through the nose), rectally, or by any means known to the skilled artisan. According to some embodiments, the composition of the described invention is a liquid solution, a suspension, an emulsion, a tablet, a pill, a capsule, a sustained release formulation, a delayed release formulation, a powder, or a suppository. The composition can be formulated with traditional binders and carriers such as triglycerides.

The composition can be administered in pharmaceutically acceptable solutions, which may routinely contain pharmaceutically acceptable concentrations of salt, buffering agents, preservatives, compatible carriers, adjuvants, and optionally other therapeutic agents.

Oral Administration

The compositions of the described invention may be in a form suitable for oral use, for example, as tablets, troches, lozenges, aqueous or oily suspensions, dispersible powders or granules, emulsions, hard or soft capsules or syrups or elixirs. For oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like.

Moreover, when desired or needed, suitable binders, lubricants, disintegrating agents and coloring agents also may be incorporated in the mixture. Powders and tablets may be comprised of from about 5 to about 95 percent of the composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Compositions intended for oral use can be prepared according to any known method, and such compositions may contain one or more agents selected from the group consisting of sweetening agents, flavoring agents, coloring agents, and preserving agents in order to provide pharmaceutically elegant and palatable preparations.

Tablets may contain the active ingredient(s) in admixture with non-toxic pharmaceutically-acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch or alginic acid; binding agents, for example, starch, gelatin or acacia; and lubricating agents, for example, magnesium stearate, stearic acid or talc. The tablets may be uncoated or they may be coated by known techniques, for example, to delay disintegration and absorption in the gastrointestinal tract and thereby provide a sustained action over a longer period, to protect the composition from oxidation or photodegradation; or for controlled release. For example, a time delay material such as glyceryl monostearate or glyceryl distearate can be employed.

Compositions of the described invention also may be formulated for oral use as hard gelatin capsules, where the active ingredient(s) is(are) mixed with an inert solid diluent, for example, calcium carbonate, calcium phosphate or kaolin, or soft gelatin capsules wherein the active ingredient(s) is (are) mixed with water or an oil medium, for example, peanut oil, liquid paraffin, or olive oil.

Liquid form preparations include solutions, suspensions and emulsions wherein the active ingredient(s) is (are) in admixture with excipients suitable for the manufacture of aqueous suspensions and emulsions. Such excipients are suspending agents, for example, sodium carboxymethylcellulose, methylcellulose, hydroxypropylmethylcellulose, sodium alginate, polyvinylpyrrolidone, gum tragacanth, and gum acacia; dispersing or wetting agents may be a naturally-occurring phosphatide such as lecithin, or condensation products of an alkylene oxide with fatty acids, for example, polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. As an example may be mentioned water or water-propylene glycol solutions for parenteral injections or addition of one or more coloring agents, one or more flavoring agents, and one or more sweetening agents, such as sucrose or saccharin and pacifiers for oral solutions, suspensions and emulsions.

Compositions of the described invention may be formulated as oily suspensions by suspending the active ingredient in a vegetable oil, for example arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions can be preserved by the addition of an antioxidant such as ascorbic acid.

Compositions of the described invention may be formulated in the form of dispersible powders and granules suitable for preparation of an aqueous suspension by the addition of water. The active ingredient in such powders and granules is provided in admixture with a dispersing or wetting agent, suspending agent, and one or more preservatives. Suitable dispersing or wetting agents and suspending agents are exemplified by those already mentioned above. Additional excipients, for example, sweetening, flavoring and coloring agents also can be present.

The compositions of the invention also may be in the form of an emulsion. An emulsion is a two-phase system prepared by combining two immiscible liquid carriers, one of which is disbursed uniformly throughout the other and consists of globules that have diameters equal to or greater than those of the largest colloidal particles. The globule size must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil. Thus, the compositions of the invention may be in the form of an oil-in-water emulsion. The oily phase can be a vegetable oil, for example, olive oil or arachis oil, or a mineral oil, for example a liquid paraffin, or a mixture thereof. Suitable emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate. The emulsions also may contain sweetening and flavoring agents.

The compositions of the invention also may be formulated as syrups and elixirs. Syrups and elixirs may be formulated with sweetening agents, for example, glycerol, propylene glycol, sorbitol or sucrose. Such formulations also may contain a demulcent, a preservative, and flavoring and coloring agents. Demulcents are protective agents employed primarily to alleviate irritation, particularly mucous membranes or abraded tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

For buccal administration, the compositions of the described invention may take the form of tablets or lozenges formulated in a conventional manner.

There are three general methods of tablet preparation: the wet-granulation method; the dry-granulation method; and direct compression. The method of preparation and the added ingredients are selected to give the tablet formulation the desirable physical characteristics allowing the rapid compression of tablets. After compression, the tablets must have a number of additional attributes such as appearance, hardness, disintegration ability, appropriate dissolution characteristics, and uniformity, which also are influenced both by the method of preparation and by the added materials present in the formulation.

According to some embodiments, the tablet is a compressed tablet (CT). Compressed tablets are solid dosage forms formed with pressure and contain no special coating. Generally, they are made from powdered, crystalline, or granular materials, alone or in combination with binders, disintegrants, controlled-release polymers, lubricants, diluents and colorants.

According to some embodiments, the tablet is a sugar-coated tablet. These are compressed tablets containing a sugar coating. Such coatings may be colored and are beneficial in covering up drug substances possessing objectionable tastes or odors and in protecting materials sensitive to oxidation.

According to some embodiments, the tablet is a film-coated tablet. These compressed tablets are covered with a thin layer or film of a water-soluble material. Numerous polymeric substances with film-forming properties may be used.

According to some embodiments, the tablet is an enteric-coated tablet. These Compressed tablets are coated with substances that resist solution in gastric fluid but disintegrate in the intestine.

According to some embodiments, the tablet is a multiple compressed tablet. These tablets are made by more than one compression cycle. Layered tablets are prepared by compressing additional tablet granulation on a previously compressed granulation. The operation may be repeated to produce multilayered tablets of two or three layers. Press-coated tablets (dry-coated) are prepared by feeding previously compressed tablets into a special tableting machine and compressing another granulation layer around the preformed tablets.

According to some embodiments, the tablet is a controlled-release tablet. Compressed tablets can be formulated to release the drug slowly over a prolonged period of time. Hence, these dosage forms have been referred to as prolonged-release or sustained-release dosage forms.

According to some embodiments, the tablet is a tablet for solution. These compressed tablets may be used to prepare solutions or to impart given characteristics to solutions.

According to some such embodiments, the tablet is an effervescent tablet. In addition to the drug, these tablets contain sodium bicarbonate and an organic acid such as tartaric acid or citric acid. In the presence of water, these additives react, liberating carbon dioxide that acts as a disintegrator and produce effervescence.

According to some embodiments, the tablet is a buccal and or sublingual tablet. These are small, flat, oval tablets intended for buccal administration and that by inserting into the buccal pouch may dissolve or erode slowly.

According to some embodiments, the tablet is a molded tablet or tablet triturate.

According to some embodiments, the tablet comprises a compressed core comprising at least one component of the described formulation and a membrane forming composition. Formulations utilizing membrane forming compositions are known to those of skill in the art. (see, e.g., Remington's Pharmaceutical Sciences, 20th Ed. (2000).) Such membrane forming compositions may include, for example, a polymer, such as, but not limited to, cellulose ester, cellulose ether, and cellulose ester-ether polymers, an amphiphilic triblock copolymer surfactant, such as ethylene oxide-propylene oxideethylene oxide, and a solvent, such as acetone, which forms a membrane over the core. The compressed core may contain a bi-layer core including a drug layer and a push layer.

Non-Oral Administration

The term "non-oral administration" represents any method of administration in which a composition is not provided in a solid or liquid oral dosage form, wherein such solid or liquid oral dosage form is traditionally intended to substantially release and or deliver the drug in the gastrointestinal tract beyond the mouth and/or buccal cavity. Such solid dosage forms include conventional tablets, capsules, caplets, etc., which do not substantially release the drug in the mouth or in the oral cavity. It is appreciated that many oral liquid dosage forms such as solutions, suspensions, emulsions, etc., and some oral solid dosage forms may release some of the drug in the mouth or in the oral cavity during the swallowing of these formulations. However, due to their very short transit time through the mouth and the oral cavities, the release of drug from these formulations in the mouth or the oral cavity is considered de minimus or insubstantial. Accordingly, it is understood that the term "non-oral" includes parenteral, transdermal, inhalation, implant, and vaginal or rectal formulations and administrations. Further, implant formulations are to be included in the term "non-oral," regardless of the physical location of implantation. Particularly, implantation formulations are known which are specifically designed for implantation and retention in the gastrointestinal tract. Such implants are also considered to be non-oral delivery formulations, and therefore are encompassed by the term "non-oral."

Rectal Administration

The compositions of the described invention may be in the form of suppositories for rectal administration of the composition, such as for treating pediatric fever. The terms "rectal" or "rectally" as used herein refer to introduction into the body through the rectum where absorption occurs through the walls of the rectum. These compositions can be prepared by mixing the drug with a suitable nonirritating excipient such as cocoa butter and polyethylene glycols which are solid at ordinary temperatures but liquid at the rectal temperature and will therefore melt in the rectum and release the drug. When formulated as a suppository the compositions of the invention may be formulated with traditional binders and carriers, such as triglycerides.

According to some embodiments, the tablet is a compressed suppository or insert. For preparing suppositories, a low melting wax such as a mixture of fatty acid glycerides, such as cocoa butter, is first melted, and the active ingredient is dispersed homogeneously therein by stirring or similar mixing. The molten homogeneous mixture is then poured into convenient sized molds, allowed to cool and thereby solidify.

Parenteral Administration

The compositions of the described invention may be in the form of a sterile injectable aqueous or oleaginous suspension. Injectable preparations, such as sterile injectable aqueous or oleaginous suspensions, may be formulated according to the known art using suitable dispersing or wetting agents and suspending agents.

The sterile injectable preparation may also be a sterile injectable solution or suspension in a nontoxic parenterally acceptable diluent or solvent, for example, as a solution in 1, 3-butanediol. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion (mixture) in which a finely-divided species is combined with another species, with the former being so finely divided and mixed that it does not rapidly settle out. In everyday life, the most common suspensions are those of solids in liquid water. Among the acceptable vehicles and solvents that may be employed are water, Ringer's solution, and isotonic sodium chloride solution. In addition, sterile, fixed oils are conventionally employed as a solvent or suspending medium. For parenteral application, particularly suitable vehicles consist of solutions, preferably oily or aqueous solutions, as well as suspensions, emulsions, or implants. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension also may contain suitable stabilizers or agents, which increase the solubility of the compounds to allow for the preparation of highly concentrated solutions. Alternatively, the active compounds may be in powder form for constitution with a suitable vehicle, e.g., sterile pyrogen-free water, before use.

The active agent, when it is desirable to deliver it locally, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Suitable liquid or solid pharmaceutical preparation forms are, for example, microencapsulated, and if appropriate, with one or more excipients, encochleated, coated onto microscopic gold particles, contained in liposomes, pellets for implantation into the tissue, or dried onto an object to be rubbed into the tissue. Such pharmaceutical compositions also may be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The pharmaceutical compositions are suitable for use in a variety of drug delivery systems. For a brief review of methods for drug delivery, see Langer R. "New methods of drug delivery." Science. 249(4976): 1527-1533 (1990), which is incorporated herein by reference.

Injectable depot forms are made by forming microencapsulated matrices of a described inhibitor in biodegradable polymers such as polylactide-polyglycolide. Depending upon the ratio of inhibitor to polymer and the nature of the particular polymer employed, the rate of drug release may be controlled. Such long acting formulations may be formulated with suitable polymeric or hydrophobic materials (for example as an emulsion in an acceptable oil) or ion exchange resins, or as sparingly soluble derivatives, for example, as a sparingly soluble salt. Examples of other biodegradable polymers include poly(orthoesters) and poly(anhydrides). Depot injectable formulations also are prepared by entrapping the inhibitor of the described invention in liposomes or microemulsions, which are compatible with body tissues.

The locally injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Formulations for parenteral administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

The pharmaceutical agent or a pharmaceutically acceptable ester, salt, solvate or prodrug thereof may be mixed with other active materials that do not impair the desired action, or with materials that supplement the desired action. Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation may be enclosed in ampoules, disposable syringes or multiple dose vials made of glass or plastic. Administered intravenously, particular carriers are physiological saline or phosphate buffered saline (PBS).

Delivery by Inhalation or Insufflation

The compositions of the described invention may be in the form of a dispersible dry powder for delivery by inhalation or insufflation (either through the mouth or through the nose). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. The composition of the described invention is placed within a suitable dosage receptacle in an amount sufficient to provide a subject with a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. Nos. 4,227,522; 4,192,309; and 4,105,027. Suitable containers also include those used in conjunction with Glaxo's Ventolin® Rotohaler brand powder inhaler or Fison's Spinhaler® brand powder inhaler. Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). Each of these references is incorporated herein by reference.

Topical Administration

The compositions of the described invention also may be deliverable transdermally. The transdermal compositions may take the form of creams, lotions, aerosols and/or emulsions and can be included in a transdermal patch of the matrix or reservoir type as are conventional in the art for this purpose. The term "topical" refers to administration of an inventive composition at, or immediately beneath, the point of application. The phrase "topically applying" describes application onto one or more surfaces(s) including epithelial surfaces. Although topical administration, in contrast to transdermal administration, generally provides a local rather than a systemic effect, as used herein, unless otherwise stated or implied, the terms topical administration and transdermal administration are used interchangeably. For the purpose of this application, topical applications shall include mouthwashes and gargles.

Topical administration may also involve the use of transdermal administration such as transdermal patches or iontophoresis devices which are prepared according to techniques and procedures well known in the art. The terms "transdermal delivery system", transdermal patch" or "patch" refer to an adhesive system placed on the skin to deliver a time released dose of a drug(s) by passage from the dosage form through the skin to be available for distribution via the systemic circulation. Transdermal patches are a well-accepted technology used to deliver a wide variety of pharmaceuticals, including, but not limited to, scopolamine for motion sickness, nitroglycerin for treatment of angina pectoris, clonidine for hypertension, estradiol for postmenopausal indications, and nicotine for smoking cessation.

Patches suitable for use in the described invention include, but are not limited to, (1) the matrix patch; (2) the reservoir patch; (3) the multi-laminate drug-inadhesive patch; and (4) the monolithic drug-in-adhesive patch; TRANSDERMAL AND TOPICAL DRUG DELIVERY SYSTEMS, pp. 249-297 (Tapash K. Ghosh et al. eds., 1997), hereby incorporated herein by reference. These patches are well known in the art and generally available commercially.

Additional Components

The compositions of the described invention may further include conventional excipients, i.e., pharmaceutically acceptable organic or inorganic carrier substances suitable for parenteral application which do not deleteriously react with the active compounds. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil; fatty acid monoglycerides and diglycerides, petroethral fatty acid esters, hydroxymethylcellulose, polyvinylpyrrolidone, etc.

The compositions may be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, suitable vehicles include solutions, such as oily or aqueous solutions, as well as suspensions, emulsions, or implants.

Aqueous suspensions may contain substances which increase the viscosity of the suspension and include, for example, but not limited to, sodium carboxymethyl cellulose, sorbitol and/or dextran. Optionally, the suspension also may contain stabilizers.

These compositions also may contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

The composition, if desired, also may contain minor amounts of wetting or emulsifying agents or pH buffering agents. Oral formulations can include standard carriers such as pharmaceutical grades of mannitol, lactose, starch, magnesium stearate, sodium saccharine, cellulose, magnesium carbonate, etc. Examples of suitable buffering agents include, without limitation: acetic acid and a salt (1%-2% w/v); citric acid and a salt (1%-3% w/v); boric acid and a salt (0.5%-2.5% w/v); and phosphoric acid and a salt (0.8%-2% w/v). Suitable preservatives include benzalkonium chloride (0.003%-0.03% w/v); chlorobutanol (0.3%-0.9% w/v); parabens (0.01%-0.25% w/v) and thimerosal (0.004%-0.02% w/v).

Pharmaceutically Acceptable Carrier

The pharmaceutical compositions within the described invention contain a therapeutically effective amount of a rho kinase inhibitor compound and optionally other therapeutic agents included in a pharmaceutically-acceptable carrier. The components of the pharmaceutical compositions also are capable of being commingled in a manner such that there is no interaction which would substantially impair the desired pharmaceutical efficiency.

The therapeutically effective amount of the rho kinase inhibitor compound may be provided in particles. The particles may contain the therapeutic agent(s) in a core surrounded by a coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, etc., and any combination thereof. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules that contain the therapeutic agent(s) in a solution or in a semi-solid state. The particles may be of virtually any shape.

Both non-biodegradable and biodegradable polymeric materials may be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels as described by Sawhney, et al., the teachings of which are incorporated herein. Sawhney A S, et al., Macromolecules. 26(4): 581-587 (1993). These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. In order to prolong the effect of a drug, it often is desirable to slow the absorption of the drug from subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Use of a long-term sustained release formulations may be particularly suitable for treatment of chronic conditions. Long-term sustained release formulations are well-known to those of ordinary skill in the art and include some of the release systems described above.

Pharmaceutically Acceptable Salts

Depending upon the structure, the rho kinase inhibitor compound, and optionally at least one other therapeutic agent, may be administered per se (neat) or, depending upon the structure of the inhibitor, in the form of a pharmaceutically acceptable salt. TN-acetyl cysteine may form pharmaceutically acceptable salts with organic or inorganic acids, or organic or inorganic bases. When used in medicine the salts should be pharmaceutically acceptable, but non-pharmaceutically acceptable salts conveniently may be used to prepare pharmaceutically acceptable salts thereof.

By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002).

The salts may be prepared in situ during the final isolation and purification of the compounds described or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides, such as methyl, ethyl, propyl, and butyl chlorides, bromides and iodides; dialkyl sulfates like dimethyl, diethyl, dibutyl and diamyl sulfates; long chain halides, such as decyl, lauryl, myristyl and stearyl chlorides, bromides and iodides; arylalkyl halides, such as benzyl and phenethyl bromides, and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts may be also obtained using standard procedures well known in the art, for example by reacting with a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

According to some embodiments, the described invention provides a kit comprising a composition and a packaging material. According to some embodiments, the kit further comprises a means for administering the composition. According to some embodiments, the composition comprises at least one ROCK compound. According to some embodiments, at least one ROCK inhibitor compound is telmisartan. According to some embodiments, the packaging material is an instruction. According to some embodiments, the means for delivering the composition comprises a syringe comprising the composition. According to some embodiments, the composition of the kit further comprises a pharmaceutically acceptable excipient.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which can independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g., amounts, temperatures, etc.) but some experimental errors and deviations should be accounted for. Unless indicated otherwise, parts are by weight, molecular weight is weight average molecular weight, temperature is in degrees Centigrade, and pressure is at or near atmospheric.

Example 1

The Effect of ROCK Inhibitors on GVHD in vivo

In a previous study, B6C3 F1 mice (offspring of C57BL/6 female mice crossed with C3H male mice; obtained from Jackson Laboratory) were used as a model of GVHD in order to determine the effect of the ROCK inhibitor Fasudil® on GVHD in vivo. Iyengar S, et al., Biol Bood Marrow Transplant. 20(8): 1104-1111 (2014). These mice are commonly used as a model because they mimic the spectrum of the host immune responses in GVHD. For example, CD4 and CD8 T cells in B6C3 recipient mice respond to MHC class I and class II disparity and minor HA mismatches between donor and recipient cells (Reddy P, Ferrara J L M. Mouse models of graft-versus-host disease. 2009 Feb. 28. In: StemBook (Internet). Cambridge (Mass.): Harvard Stem Cell Institute; 2008).

Adult male C3B6 mice exposed to lethal irradiation received anti-T cell treated bone marrow transplants (ATBM) from donor C3H mice with or without added donor T cells. In some cases, mice receiving ATBM and T cells were also administered Fasudil® i.p. and p.o., Fasudil-hydrochloride, was given i.p. 200 μg twice daily, and oral fasudil-dihydrochloride was given as 1 mg/ml drinking water (~3 mg per day). This dual mode of administration was started one or two days prior to irradiation and continued for 10 days post-transplant, after which time i.p. injections were discontinued while p.o. drug was maintained for the period of observation (up to 90 days).

Figure 5:
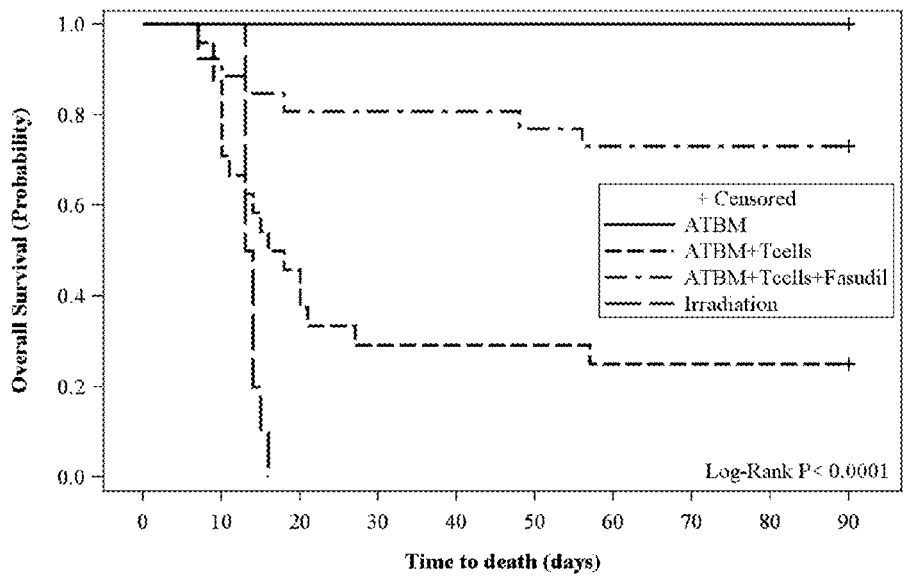
FIG. 5 diagrammatically illustrates the impact of Fasudil® on survival of C3B6 F1 mice treated with irradiation, anti-T cell-treated bone marrow (ATBM) and donor T cells.
Figure 5:
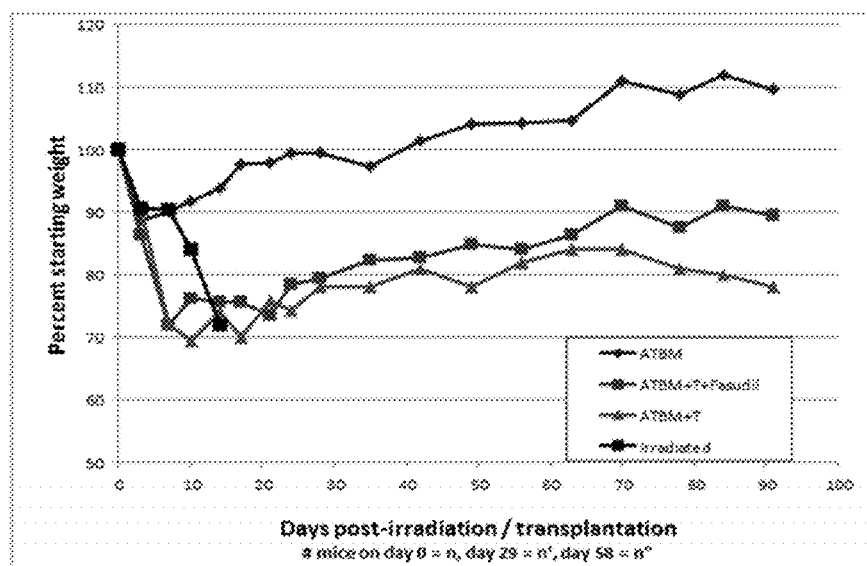

FIG. 5-A shows the results of this study, depicting groupwise Kaplan-Meier survival curves of non-transplanted irradiated mice, ATBM recipient mice, ATBM+T cells recipient mice, and ATBM+T cells+Fasudil® recipient mice at 90 days (the Fasudil® treated group (p<0.0001)). An increased survival rate was observed in ATBM+T cells+Fasudil®-treated mice (73%) compared to ATBM+T cells-treated mice (25%). These data are summarized in Table 3.

TABLE 3

Summary of 90 Day Survival Rates

| Treatment | Sample Size | Survival Rate (95% CI) |
|---|---|---|
| Irradiation | 10 | 0% |
| ATBM | 18 | 100% |
| ATBM + T cells | 24 | 25% (10%-44%) |
| ATBM + T cells + Fasudil ® | 26 | 73% (55%-88%) |

Example 2

The Effect of ROCK Inhibitors on Initial Weight Loss Associated with GVHD

It is well known that weight loss occurs in patients with GVHD. Jacobsohn D A, et al., Bone Marrow Tranplant. 29(3): 231-236 (2002). In this study, C3B6 mice were used to determine the effect of ROCK inhibitors on GVHD-associated weight loss.

C3B6 mice were treated according to Example 1. ATBM+T cells+Fasudil® recipient mice experienced roughly the same magnitude of weight loss (~25% total body weight) as ATBM+T cells recipient mice over the first three weeks post-transplant (data not shown). In most experiments, the ATBM+T cells+Fasudil® recipient mice subsequently recovered more weight than ATBM+T cells recipient mice, but less weight than ATBM only control mice (data not shown). Despite the similar initial weight losses of Fasudil® treated and untreated T cell recipients, the two groups had different rates of diarrhea. The majority (>70%) of untreated mice had loose stools for one or more days between the second and third weeks post-transplant; the period of highest mortality incidence. By comparison, less than 20% of the Fasudil® treated mice developed clinically observable diarrhea during that time. Diarrhea resolved by the fourth week among survivors in both groups.

The ATBM only control mice lost approximately 10% of their total body weight, which they recovered in two weeks (data not shown). By the time of sacrifice (at about 2 months), the ATBM only control mice reached 120% of starting weight. FIG. 5-B shows the results of this study.

Example 3

The Effect of ROCK Inhibitors on Skin Inflammation in Mice Receiving Donor T Cells Skin is most commonly affected and usually the first organ involved in GVHD. Ferrara J L M, et al., Lancet. 373(9674): 1550-1561 (2009). In this study, C3B6 mice were used to determine the effect of ROCK inhibitors on GVHD-associated skin inflammation.

C3B6 mice were treated according to Example 1. Fasudil® did not prevent skin inflammation in ATBM+T cells+Fasudil® recipient mice. Skin inflammation in C3B6 treated mice occurred in the fourth week and gradually waned over a two week-period.

Example 4

The Effect of ROCK Inhibitors on Systemic Donor Allotolerance for Host

Alloreactivity mediated by donor T cells, also known as GVTE, can produce immunologic control or eradication of residual malignancy after allogeneic transplant. Rezvani A R and Storb R F, J. Autoimmun. 30(3): 172-179 (2008). This study was performed to determine whether spleen cells from ATBM+T cells+Fasudil® recipient mice were allotolerant of C3B6 mouse host cells.

Mixed Lymphocyte Reaction (MLR)

Classically, a MLR is carried out by co-incubating lymphocytes from two strains that differ in histocompatibility genes for several days, and the proliferative response of T cells of one lymphocyte population to histocompatibility antigens of the other then measured.

Mouse IFN-γ ELISPOT

Secretion of IFN-γ by responder cells in a MLR was used as an indicator of cytotoxic T lymphocyte function (i.e., alloreactivity). Briefly, spleens from C3B6 mice treated according to Example 1 were harvested at day 10 (C3H donor T cells migrating to the spleen with few de novo generated T cells emigrating from the host thymus) or at day 84 (spleens containing newly generated T cells maturing within the host thymus; i.e., allotolerant of host B6 parental antigens) post-transplant for use as responders. Spleens from C3H, C3B6 and DBA mice (Jackson Laboratory) were harvested for use as stimulators. Spleens were homogenized and the cells were washed twice with Phosphate Buffered Saline (PBS) (Sigma Aldrich, St. Louis, Mo., Catalog No. P5493, or equivalent). Red blood cells were separated from lymphocytes using Ficoll®. Briefly, cells were transferred to 50 mL conical tubes containing 15 mL of Ficoll®-Paque PLUS (GE Healthcare, Waukesha, Wis., Catalog No. 17-1440-03) and centrifuged at 800 rcf (1,900-2,000 rpm) for 20 minutes with centrifuge break off. After centrifugation, the buffy coat layer (containing lymphocytes) was removed and transferred to a new 50 mL conical tube. Phosphate-buffered saline (PBS) without calcium and magnesium (Gibco, Life Technologies, Carlsbad, Calif., Catalog No. 10010-023 or equivalent) was added to the buffy coat layer so that the total volume in the conical tube is equal to 50 mL. The buffy coat layer in PBS was centrifuged at 250 rcf (1,200 rpm) for 10 minutes with centrifuge brake applied. After centrifugation, the PBS was aspirated and the lymphocyte pellet was resuspended in 48 mL of PBS. Lymphocytes resuspended in PBS were centrifuged at 250 rcf (1,200 rpm) for 10 minutes with centrifuge break applied. PBS was aspirated and PBMC pellet resuspended in 12.5% Bovine Serum Albumin (BSA) (Sigma-Aldrich, St. Louis, Mo., Catalog No. A9418-5G or equivalent) in RPMI medium (Sigma-Aldrich, St. Louis, Mo., Catalog No. R7388 or equivalent). Stimulator lymphocytes (from C3H, C3B6 and DBA mouse spleens) were irradiated for 2.5 minutes (2,000 RAD) in a cesium irradiator.

One-way MLRs were performed by mixing $1 \times 10^5$ lymphocytes from both stimulator and responder cells in a 96-well ELISPOT (eBioscience, San Diego, Calif., Catalog No. 88-7384, or equivalent) capture plate coated with anti-mouse IFN-γ antibody according to manufacturer's protocol. Concanavalin A (Con A) (Sigma-Aldrich, St. Louis, Mo., Catalog No. C5275, or equivalent) was added to responder cells as a positive control for stimulation of mouse T-cells. The capture plate containing one-way MLRs was incubated at 37° C., 5% $CO_2$ for 4 days. After 4 days of incubation, cells and media were aspirated from the capture plate. The capture plate was washed 3 times with ELISPOT Wash Buffer. Next, biotinylated detection antibody was diluted in Assay Diluent according to manufacturer's instructions. 100 μl/well of diluted detection antibody was added to the capture plate and the plate was incubated at room temperature for 2 hours. After incubation, detection antibody was aspirated from the wells and the capture plate was washed 4 times with ELISPOT Wash Buffer with a 1 minute incubation for each wash. Avidin-HRP reagent was diluted in Assay Diluent according to manufacturer's protocol. 100 μl/well of Avidin-HRP was added to the capture plate and the plate was incubated at room temperature for 45 minutes. Next, Avidin-HRP was aspirated from the wells and the capture plate was washed 3 times with ELISPOT Wash Buffer and 2 times with 1×PBS. AEC Substrate Solution was prepared and 100 μl/well was added to the capture plate. The plate was incubated at room temperature for 10-60 minutes (until spots developed). Next, the substrate reaction was stopped by washing the capture plate 3 times with 200 μl/well distilled water. The plate was air-dried and counted on a ELISPOT plate reader.

Table 4 summarizes the results of the MLR ELISPOT experiment. As shown in Table 4, there was no evidence of allo-tolerance to host C3B6 ten days after transplantation, as measured by IFN-γ ELISPOT after one way donor C3H vs. irradiated C3B6 stimulation in vitro. These early time point donor derived T cells appeared to respond even more robustly than control C3H T cells (e.g., 115.6 for ATBM+T cells+Fasudil® responders/C3B6 simulators; 2.3 for ATBM+T cells+Fasudil® responders/C3H stimulators). Spleens from mice receiving only antithymocyte treated bone marrow (ATBM) had no mature T cells present in their spleens as of day 10, and therefore, made no response to any of the cell stimulations, or to Concanavalin A. Mice receiving mature donor C3H mouse T cells had sufficient numbers of these T cells present in day 10 spleens to show reactivity to C3B6 and DBA mouse alloantigens. Without being limited by theory, it is believed that a much stronger response to host C3B6 compared to third party DBA stimulation reflects in vivo priming against B6 parental alloantigens. Mice receiving mature donor T cells plus Fasudil® showed no evidence of tolerance to host C3B6 stimulation, indicating the presence of clones stimulated in vivo to the B6 alloantigens present in the host environment. As expected, C3H stimulation induced almost no activation, reflecting C3H self-tolerance.

TABLE 4

Day 10 IFN-γ Secreting Spleen Cell Frequencies (per 100,000 cells) After 4 Day One-way Mixed Lymphocyte Reactions vs. Self (C3H), Host F1, or Third Party H-2$^d$ Allogeneic Stimulators

| Irradiated Stimulators | Responding Splenocytes from Hosts Receiving: | | |
|---|---|---|---|
| | ATBM only | ATBM + T cells | ATBM + T cells + Fasudil ® |
| C3H | 0 | 4.6 | 2.3 |
| C3B6F1 | 0 | 82.3 | 115.6 |
| DBA | 0 | 16 | 18 |
| Concanavalin A | 1 | 61.3 | 120.0 |

CFSE Labeling with Flow-Based Assessment

Figure 6:
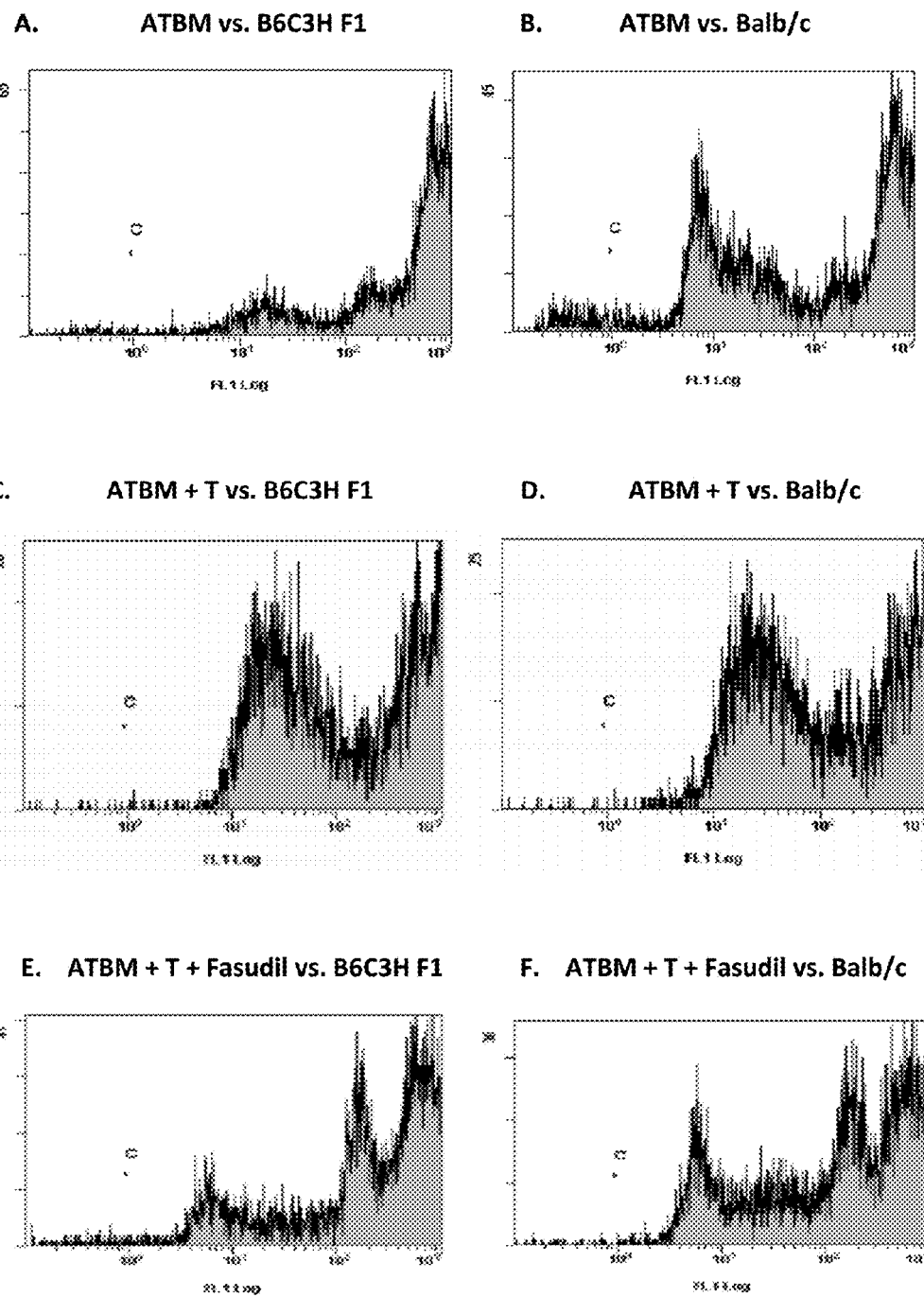
FIG. 6 is a diagram of proliferative responses of splenocytes from irradiated C3B6 hosts receiving anti-T cell-treated bone marrow (ATBM), ATBM+T cells, or ATBM+T cells+Fasudil®.
Figure 7:
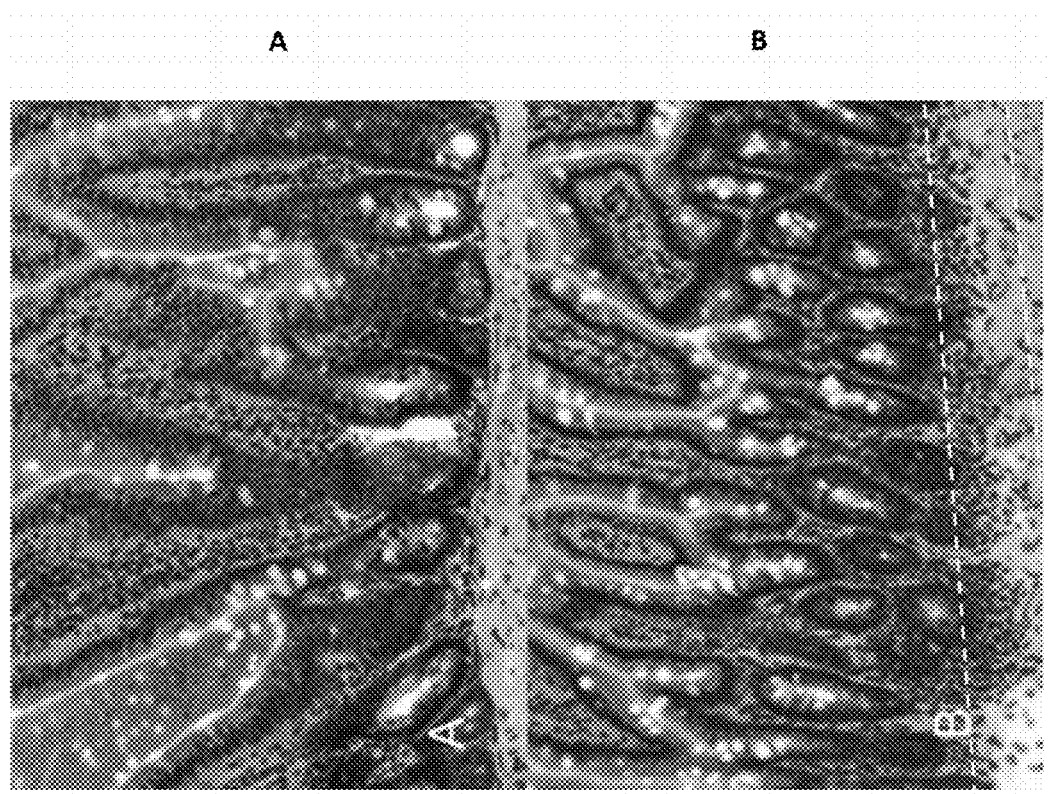
FIG. 7 shows a tissue section illustrating that Fasudil® treated mice have minimal small intestinal crypt inflammation. (A) Basilar crypts showed no infiltration. (B) Limited inflammation within dashed lines of basal layer and lamina propria, with intact crypts, in 90 day survivor Fasudil® treated mice.

Carboxyfluorescein dacetate succinimidyl ester (CFSE) labeling (Molecular Probes, Carlsbad, Calif., Catalog No. C34554, or equivalent) with flow cytometry detection was employed to assess lymphocyte cell division in response to alloantigen recognition. Briefly, lymphocytes from responders and stimulators were harvested as described above. For this experiment, sources of stimulator cells included C3H, C3B6 and Balb/c mice. Next, lymphocytes from responders were incubated in CFSE prepared according to manufacturer's protocol at 37° C. for 10 minutes. The staining was quenched by the addition of 5 volumes of ice-cold culture media (12.5% Bovine Serum Albumin (BSA) in RPMI) to the lymphocytes. Lymphocytes were incubated on ice for 5 minutes before pelleting by centrifugation. After centrifugation, the lymphocytes were washed by resuspending and pelleting 3 times in fresh culture media. One-way MLRs were performed by mixing 1×10$^5$ lymphocytes from both stimulator and CFSE responder cells in a 96-well tissue culture plate (Corning Costar, Tewksbury, Mass., Catalog No. CLS3585 or equivalent). The tissue culture plate containing one-way MLRs was incubated at 37° C., 5% $CO_2$ for 4 days. After 5 days of incubation, the cells were harvested and analyzed using a flow cytometer with 488 nm excitation and emission filters appropriate for fluorescein. The results of this experiment are shown in FIG. 6.

Spleens from day 98 survivor mice had many more lymphocytes, allowing CFSE labeling of pooled spleen cells with flow-based assessment of cell division (dilutional peaks) in response to alloantigen recognition. FIG. 6 shows that CFSE labeled splenic lymphocytes from ATBM recipients had a relatively low proportion of cells undergoing multiple rounds of division after 5 days of stimulation with irradiated host cell (FIG. 6-A), compared with the proportion of cells undergoing multiple rounds of division in response to third party allogeneic Balb/c stimulators (FIG. 6-B). The limited response to parental B6 antigens was expected from C3H stem cell derived T cells generated de novo within the F1 host thymic environment. By contrast, spleen cells from recipients of ATBM+donor T cells strongly responded to B6C3F1 stimulation (FIG. 6-C); similar in magnitude to their response to Balb/c stimulation (FIG. 6-D). Fasudil® treated recipients of ATBM+T cells also contained spleen cells that strongly responded to B6C3F1 stimulation, with multiple rounds of cell division yielding weakly fluorescent peaks (FIG. 6-E), which was comparable to their response to Balb/c (FIG. 6-F).

The results of this study indicate that ROCK inhibitors such as Fausdil® preserves alloreactivity, and thus preserves GVTE, in allogeneic bone marrow transplant recipients. Without being limited by theory, it is believed that two possible mechanisms are mediated by Rho kinase inhibition: (i) relative exclusion of alloreactive donor cells from the most sensitive and vulnerable tissues (e.g., gut); and (ii) induction of allospecific regulatory cells (i.e., the cells placed into the patient from the allogeneic bone marrow transplant which regulate immune response) homing to the most sensitive sites of GVHD. The former may be a consequence of the known ability of ROCK to interfere with cell motility and chemotaxis, while increasing the integrity and impermeability of vascular endothelium. The latter represents a newly described phenomenon whose molecular basis remains to be elucidated.

Example 5

The Effect of ROCK Inhibitors on GVHD in Vascularized Composite Allotransplants (VCA)

Rat Hindlimb Model

The rat hindlimb model can be used as a model of GVHD in order to determine the effect of Fasudil® or telmisartan on GVHD in vascularized composite allotransplants in vivo.

The rat hindlimb model, in which a parental limb is transplanted onto an F1 hybrid host, provides transplantation of precursor hematolymphoid (bone marrow) and mature (blood and lymph nodes) elements, along with transfer of their syngeneic/supportive microenvironments. This model also permits immediate engraftment of donor lymphoid cells, with development of donor-specific lymphoid chimerism. Hewitt C W et al., Transplantation. 50: 766-772 (1990); Hewitt C W et al., Transplantation. 41: 39 (1986); Hewitt C W et al., Transplant Proc. 20: 272 (1988); Hewitt C W et al., FASEB J. 3: 5233 (1989)). Chimerism produces donor-specific immune tolerance and graft versus host disease (acute and chronic GVHD) in the hybrid recipient of the parental limb. During the first 30 days post-transplantation, hybrid recipient animals become polyclonal and self- and host-specifically unresponsive in in vitro studies; results that are similar to the immune reactivity associated with GVHD in other models. Rolink A G et al., J Exp Med. 165: 1675-1687 (1987); Luzuy S et al., J Immunol. 146: 4420-4426 (1986); Wilson D B et al., Immunol Rev. 107: 159-177 (1989).

Example 6

Biomarkers of GVHD as Potential Predictors of GVHD

Plasma Proteins Detected by Enzyme Linked Immunoassay (EIA)

Progress has been made in identifying blood markers of GVHD. Levine J E, et al., Biol Blood Marrow Transplant. 18(1 Suppl): S116-S124 (2012); Paczesny S, Blood. 121(4): 585-594 (2013); Levine J E, et al., Blood. 119(16): 3854-3860 (2012); Vander Lugt M T, et al., N Engl J Med. 369(6): 529-539 (2013); Mueller T, Dieplinger B, Expert Rev Mol Diagn. 13(1): 13-30 (2013). Levine et al. showed that a panel of 6 plasma markers (elafin, IL-8, TNFR1, HGF, reg3a, IL-2Ra) significantly correlated with non-responsive GVHD and non-relapse mortality (NRM). Levine J E, et al., Biol Blood Marrow Transplant. 18(1 Suppl): S116-S124 (2012). More recently, the same group, using a more extensive panel, partially overlapping with their previous one, found that essentially full predictive power was provided by a single marker, ST2 (suppression of tumorigenicity 2), a recently described member of the IL-1R family, which binds IL-33, thereby driving T cells toward a Th1 effector phenotype. Vander Lugt M T, et al., N Engl J Med. 369(6): 529-539 (2013); Mueller T, Dieplinger B, Expert Rev Mol Diagn. 13(1): 13-30 (2013). High ST2 levels in the first two weeks post-HCT were strongly predictive of non-relapse mortality (NRM) in patients with IT GVHD, but not with skin GVHD only. The Paneth cell regeneration marker, reg3a, had independent and additive predictive value for IT GVHD. Ferrara J L, et al., Blood. 118(25): 6702-6708 (2011). This is consistent with very recent findings from models showing that early immune mediated destruction of Paneth cells in the intestinal villous crypts eliminates their production of beneficial alpha-defensins, leading, in turn, to altered gut flora, with overgrowth by *E. coli, C. difficile*, seeding of organs, and septic complications causing death. Ferrara J L, et al., Blood. 118(25): 6702-6708 (2011); Holler E, et al., Int J Inflam. 2010: 814326 (2010); Penack O, et al., Blood. 115(10): 1865-1872 (2010); Eriguchi Y, et al., Blood. 120(1): 223-231 (2012); Cooke K R, et al., J Clin Invest. 107(12): 1581-1589 (2001). In a somewhat analogous, but converse manner, Levine at al. found that plasma elafin levels rose at the onset of skin GVHD, but not IT GVHD, and were predictive of NRM. Levine J E, et al., Biol Blood Marrow Transplant. 18(1 Suppl): S116-S124 (2012). By contrast with elafin or reg3a and ST-2, ceruloplasmin plasma levels between days 7-28 post-HCT were highly significant predictors of both skin and IT GVHD. Lv M, et al., PLoS One. 8(3):e58735 (2013).

Endotoxin as a Potential Biomarker of GVHD

Given the importance of the IT microbiome and tissue disruption in intestinal GVHD, there has been great interest throughout many fields of medicine, in monitoring the release of lipopolysaccharide (LPS) or its toxic Lipid A moiety in the blood. Unfortunately, measurement of LPS or Lipid A in blood, plasma, or serum is fraught with difficulties, due to the presence of various binding proteins and cells, with varying rates of dissociation under different conditions. An Endotoxin Activity Assay (EAA™, Spectral Diagnostics, Inc.) can measure Lipid A endotoxin in whole blood with sufficient sensitivity, specificity, and reproducibility to be FDA approved for detection of endotoxin in whole blood. Romaschin A D, et al., Crit Care. 16(6): 248 (2012); Hilmi I, et al., J Organ Dysfunction. 5(4): 254-260 (2009); Sanada Y, et al., J Surg Res. 180(2): 349-355 (2013); Marshall J C, et al., J Infect Dis. 190(3): 527-534 (2004); Ikeda T, et al., Innate Immun. 20(8): 881-887 (2014). The EAA uses the biological response of neutrophils in a subject's blood to an immunological complex of endotoxin and exogenous antibody as a measure of endotoxin activity in the subject; the EAA reacts specifically with LPS of Gram negative bacteria, and does not cross-react with cell wall constituents of Gram positive bacteria and other microorganisms. Monitoring blood LPS with an EAA may be used as a predictive/correlative tool for predicting and monitoring acute GVHD.

Example 7

GVHD and the Microbiome

Changes in stool bacteria (increased Lactobacilli species, decreased Clostridia species) can be correlated with acute GVHD in both humans and mice. See Jenq R R, et al., J Exp Med. 209(5): 903-911 (2012). In allogeneic renal transplants, Fricke et al. also found longitudinal alterations in stool, oral, and urinary microbiota. Fricke W F, et al, Am J Transplant. 14(2): 416-427 (2014). Urine samples tested positive for a diverse flora in one third of cases, with no symptomatic evidence of UTI. Disruptions in the IT microbiome may correlate strongly with IT GVHD. Evidence is accumulating that gut function influences skin health. Arck et al., have reviewed their own data and others' documenting improvement in mouse skin inflammation following the oral administration of probiotics. Arck P, et al., Exp Dermatol. 19(5): 401-405 (2010).

Measurement of ROCK Activity In Vivo

ROCK activity in vivo can be a marker for GVHD. ROCK also may be suppressed by telmisartan independently of, or concomitantly with suppression of GVHD. ROCK phosphorylation of a myosin binding subunit (MBS) of Myosin Phosphatase within peripheral blood mononuclear cells (PBMCs) is monitored by Western blotting. The relative amount of phosphorylated (Threonine 853 and Threonine 696) MBS: total MBS in cell lysates is monitored using anti-phospho-MYPT1 (thr696), and anti-phospho-MYPT1 (thr853) mAbs (Millipore, Billerica, Mass., USA). Total ROCK II in cells using anti-ROCK2 antibodies (AbCam, Cambridge, Mass., USA) treated with telmisartan is quantified. After blotting for specific proteins, membranes are stripped and blotted with glutaraldehyde 3-phosphate dehydrogenase (GAPDH) antibody for protein normalization. Samples are obtained from baseline, post-engraftment after treatment with telmisartan (~6, 10, and 14 weeks post-HCT), and at two time points after stopping telmisartan, and assays are run on batched cryopreserved samples.

Study Rationale and Overview

In humans, as in mice, IT GVHD is the main cause of death within the first 100 days of HCT. Reshef R, et al., N Engl J Med. 367(2): 135-145 (2012). A single clinical trial has tested the concept of selective suppression of IT GVHD, using the CCR5 blocker, maraviroc, which effectively targets a significant proportion of donor T cells homing to the IT. There were no acute deaths among treated patients, but there was a 20% increase in cancer relapse at 1 year, when compared with historical controls. While this did not reach statistical significance, it raises questions about the specificity of CCR5+ cell targeting and loss of systemic alloreactivity at the doses used.

Telmisartan, which has anti-inflammatory PPARγ agonistic and Rho kinase (ROCK) inhibitory mechanisms of action, will be tested in this trial. Telmisartan will be used for the initial 100 days post-transplant, which is considered the acute period for GVHD. The phase I/II trial with telmisartan is modeled loosely on the maraviroc trial. Primary endpoints are drug tolerability, Grade III and IV GVHD, non-relapse mortality (NRM, including Grade V GVHD), primary or secondary graft failure, and cancer progression or relapse at 100 and 180 days.

A secondary (exploratory) goal of this study is to examine the correlation of various blood biomarkers with the onset of GVHD.

The blood markers to be assessed are ST2 and reg3a (which have been associated with IT GVHD), elafin (associated with skin GVHD) and ceruloplasmin (previously correlated with both gut and skin GVHD). Additionally, the EAA will be used. Confirmation of one or more biomarkers' association with GVHD would allow more timely use of intensified immune suppressive drugs, ideally for shorter periods, thereby decreasing GVHD and toxicity.

The ratio of certain Treg and Teff subsets in peripheral blood will be examined. While there is no question that such subsets are crucial for the outcome of GVHD, it has been difficult to use them as peripherally circulating markers, since they rapidly leave the blood stream and lodge in bone marrow or tissue sites of potential GVHD. CD4+FoxP3+CD73+ and CD4+FoxP3+CD39+ T regulatory cells (Tregs) will be monitored, as potential peripheral markers of protection from GVHD; CD4+CD146+CCR5+ cells, which may be positively correlated with GVHD (Gomez A., et al. A Novel CD4+CD146+CCR5+ T-cell population is a biomarker of intestinal graft-versus-host disease. $39^{th}$ meeting of the European Group for Blood and Marrow Transplantation. Apr. 10, 2013), will also be monitored. Staining for CD8+FoxP3+CD39+ and CD8+FoxP3+CD73+ Tregs, will be conducted. Screening for a4b7+CD4+FoxP3+ Tregs that may reflect cells homing to the IT, will also be conducted.

ROCK inhibitory activity of telmisartan has been documented in rodent models. A recent study has shown a statistically significant increase in ROCK activity among stroke patients, with ROCK activity, measured as phosphorylated: total Myosin Binding Subunit, revealed to be an independent predictor of stroke in high risk ischemic patients. Cheng C I, et al., Biomed Res Int. 2014: 214587 (2014). In order to determine ROCK inhibitory activity, control and experimental samples are subjected to SDS-PAGE and subsequent transfer to polyvinylidene fluoride or comparable membranes. After transfer, the membranes are blocked (e.g., incubation in 3% bovine serum albumin at room temperature) and then incubated with rabbit primary polyclonal antibodies against phospho-specific $Thr^{853}$-myosin binding subunit (MBS) (Abcam Cambridge, Mass.) (1:2000), or MBS (Covance, Berkley, Calif.) (1:1000). The membranes are washed and incubated with labeled anti-rabbit antibodies. Immunoreactive bands are visualized with enhanced chemiluminescent detection reagents. ROCK activity is expressed as the ratio of phosphorylation levels of MBS (pMBS) in each sample per pMBS in each positive control divided by total MBS (tMBS) in each sample per tMBS in each external control.

Stool and urine microflora samples will be batch analyzed for diversity, firmaceutes: bacteroidetes: enterocci ratios, and *Clostridia:Lactobacilli* ratios. This will be a post-hoc analysis that may contribute to the growing understanding of the role of the gut microbiome in the development of GVHD.

Study Objectives
Primary Objective

The primary objective of the study is to demonstrate the utility of telmisartan at 160 mg/day, for the prevention of grade II or greater acute graft versus host disease (GVHD) in patients receiving allogeneic HCT.

Secondary Objectives

The secondary objective of the study is to assess the safety and tolerability of telmisartan at doses of 160 mg per day (adjusted downward to 80 or 40 mg/day as necessary, on an individual basis for each patient), given orally to patients receiving allogeneic HCT.

Exploratory Objectives

An exploratory objective of the study is to identify biomarkers that correlate with, or are predictive of, grade III-V GVHD.

An additional exploratory objective of the study is to identify gut and urine flora diversity (Shannon Diversity Index) and changes in the percentages of firmaceutes, bacteroidetes, and enterocci, ratio of Clostridia and Lactobacillus species over time, pre- and post-transplantation, in the presence or absence of telmisartan and/or GVHD. The healthy microbiome contains 40-50% firmaceutes, 30-40% bacteroidetes, and <10% enterocci. Some dysbiosis occurs as a result of conditioning and transplantation, with enterocci increasing to ~25%. However, during GVHD, these ratios change dramatically, with enterocci increasing to ~50%, and bacteroidetes dramatically dropping.

An additional exploratory objective of the study is to assess the level of ROCK activity in peripheral blood mononuclear cells, on and off telmisartan treatment, in the presence or absence of GVHD.

A further exploratory objective of the study is to measure percentages of lymphocyte subsets, described above, and associated with GVHD or suppression of GVHD.

Study Population

The study population will consist of 60 patients undergoing allogeneic HCT for treatment of hematologic malignancies meeting the following criteria. Subject eligibility will be documented by a qualified member of the study team.

Eligibility Criteria
Inclusion Criteria

Subjects must meet all of the following inclusion criteria to be eligible for enrollment into the study:

1. Diagnosis of:
    Acute myeloid or lymphoid leukemia in remission,
    Myelodysplastic syndrome,
    Chronic lymphoid leukemia,
    Non-Hodgkin lymphoma,
    Hodgkin lymphoma,
    Chronic myeloid leukemia in chronic or accelerated phase,
    Myeloproliferative disorder, or
    Multiple myeloma
2. Undergoing allogeneic HSC transplantation from a related or unrelated donor matched at least at 7 of 8 of the HLA-A, -B, -C, and DR loci ("8/8" or "7/8" match)

3. Undergoing allogeneic HSC transplantation after a myeloablative TBI-, busulfan-, or (non-myeloablative) melphalan-based pre-transplant conditioning regimen. Regimens for transplantation will include at one of the following agents, given in conjunction with fludarabine or cyclophosphamide:

Busulfan 130 mg/m$^2$ iv daily×2 (reduced intensity) or 4 days

TBI 150 cGy bid×8 doses (1200 Gy)

Melphalan 140 mg/m$^2$. (Although melphalan is not a myeloablative regimen, it results in clinically significant mucositis and patients receiving this medication will be of considerable interest in the analysis of these data.)

4. Male or female patient age 18 years or older
5. Karnofsky performance status ≥70% at time of initiation of pre-transplant conditioning
6. Transplantation-specific co-morbidity score of <3 at time of initiation of pre-transplant conditioning
7. Patients taking antihypertensive medications (including telmisartan) are eligible but the patient must discontinue treatment at least 48 hours prior to first dose of study medication
8. Capable of giving informed consent and having signed an informed consent form.

Exclusion Criteria

Subjects who meet any of the following exclusion criteria will not be eligible for enrollment in this study:

1. Inability to provide informed consent
2. Subjects with known heart failure, advanced renal impairment requiring renal replacement therapy, or liver failure although these patients would most likely not be eligible for HCT.
3. Subjects taking ACE inhibitors, potassium supplements, or spironolactone (or any other potassium-sparing diuretics) who cannot discontinue use prior to initiation of study treatment OR who require a high-potassium diet
4. Patient unable to discontinue current hypertension medication for medical or other reasons for two days prior to starting telmisartan
5. Chronic symptomatic hypotension, volume depletion.

Recruitment Procedures

Patients who are already scheduled to undergo HCT for a hematologic malignancy (as per eligibility criteria) will be recruited by the trial site. Once a potential subject's eligibility has been determined via review of medical records, the subject will be approached for participation by the PI, sub-I, or another qualified member of the research team. The patient will be given a copy of the informed consent form to review. No recruitment materials (e.g., flyers, advertisements) will be used to recruit patients into this study. Patients will not be offered financial or other material incentives to participate in this study.

All patients enrolled in this study must have first met all the eligibility criteria for transplantation in accordance with the treatment plan being used. A conference will be held with the patient and family to discuss this research study. All potential risks associated with participation in this study will be discussed as objectively as possible. From their prior discussions with the transplant team, patients will already have been made aware of the risk of GVHD resulting from allogeneic HCT.

The issue of how patients on this study may be directly benefited by this treatment protocol, as it is designed to reduce the incidence and severity of GVHD, will be discussed. It will be explained that participation in this study is voluntary. Patients can choose not to participate in this study and still undergo their scheduled allogeneic transplant. All patients who meet the eligibility requirements will be offered the option to participate in this transplant protocol.

Methods

Study Design

Overall Study Design

This is single-center, open-label, prospective study of telmisartan for the prevention of acute GVHD in approximately 60 subjects undergoing allogeneic HCT for treatment of a hematologic malignancy. Subjects will receive 160 mg Micardis brand telmisartan (Boehringer-Ingelheim) in the form of two 80 mg pills, taken together, once daily, starting 2 days prior to HCT (day −2). Systolic and Diastolic Blood pressure will be monitored at least twice daily while in the hospital. Patient who develop severe hypotension (≥grade 3) will have their doses adjusted accordingly. Once the patient is discharged post-HCT, treatment will continue in the outpatient setting. Treatment will continue through Day +98 post-HCT for a total of 101 days (Day −2 to Day +98). After treatment discontinuation on or before day +98 post-HCT, subjects will be followed for up to 6 months (Day +180) for primary and secondary endpoints.

Study Endpoints

Efficacy Endpoints

Efficacy endpoints will be based on Grade III-IV GVHD criteria as per the 1994 Consensus Conference on Acute GVHD (CCAG) Grading criteria. Przepiorka D, et al., Bone Marrow Transplant. 15(6):825-828 (1995).

Safety Endpoints

The safety endpoints are as follows: 1) grade III-IV hypotension as per the National Cancer Institute's Common Terminology Criteria for Adverse Events version 4.0 (CT-CAE); 2) relapse/progression of disease; 3) primary graft delay, defined as ANC<500×3 consecutive draws at 28 days, and <5% donor CD3 T cell chimerism at day 28 and/or day 56; 4) primary graft failure, defined as ANC<500 at 56 days×3 consecutive draws and <5% donor CD3 T cell chimerism at day 84; 5) secondary graft failure (loss of engraftment), defined as loss of ANC>500 after 3 days of ANC>500, or loss of chimerism subsequent to detection of chimerism; and 6) non-relapse mortality (occurance of unexpected, study drug-related).

Exploratory Endpoints

The exploratory endpoints are as follows: 1) ST2 EIA (Presage, Critical Diagnostics); 2) Reg3a EIA; 3) ceruloplasmin EIA; 4) elafin EIA; 5) endotoxin activity assay (EAA, Spectral Diagnostics); 6) gut and urine microbiome sequencing of 16S rRNA DNA, to generate Shannon Diversity index and ratio of Clostridia:Lactobacilli, and firmacutes vs. bacteroidetes vs. Enterococci species; 7) PBMC ROCK activity as measured by ratio of Phosphorylated:Total MBS in cryopreserved PBMCs, ROCK enzyme protein levels by WB; and 8) percentages of CD4+ and CD8+ cells expressing FoxP3 and CD73 or CD39, percentages of CD4+CD146+CCR5+ cells, and percentages of a4b7 cells expressing CD39 or CD73.

Treatment Schedule

Telmisartan Dosing

Subjects will be asked to discontinue any antihypertensive medications they may be taking at least 48 hours prior to first dose of study medication.

For the purposes of this study, a commercial supply of Micardis® brand (Boehringer Ingelheim) of telmisartan tablets will be used due to the superior release kinetics of Micardis® compared to several generic brands, and to ensure uniformity of product during the trial. Patel P A, Patravale V B, Int J Pharm Sci Res. 1(8): 282-292 (2010). The standard, oral route of administration for telmisartan (Micardis®) will be used. The dose of 160 mg used in this study has been assessed in multiple clinical studies and has shown no statistical increase in anti-hypertensive effect or adverse side effects. Forclaz, A, et al., Hypertension. 41(1), 31-36 (2003); Schumacher H, Mancia G, Blood Press Suppl. 1:32-40 (2008); Sharpe M, et al., Drugs. 61(10):1501-1529 (2001); Bähr I N, et al., Hypertension. 58(4):725-732 (2011); Chetty V T, et al., Blood Pressure. 23(1): 54-60 (2014); White W B, J Clin Hypertens. 4: 20-25 (2002). All subjects will receive 160 mg telmisartan administered as two 80 mg tablets taken together p.o. once daily starting two days prior to HCT (Day −2) and continuing for 101 days (until Day +98 post-HCT), unless discontinued early from treatment. Subjects will be instructed to take their study medication at approximately the same time every day, before bedtime, or upon waking, but there are no strict requirements for the timing of administration.

Treatment Compliance

Most patients will be discharged within 2-3 weeks following HCT. Upon discharge patients will be given drug diaries to complete as they take their daily study medication at home. Subjects will be instructed to bring their study medication and drug diaries to all follow-up appointment. Compliance will be monitored by the study team during the treatment period. Missed days of medication will be noted. Five missed doses over any 2 week period for reasons other than hypotension or other side effects will be considered non-compliance. Patients who are non-compliant prior to 28 days post-HCT will be withdrawn from the study. Subjects who are non-compliant after 28 days post-HCT will be allowed to continue on study treatment with counseling on compliance.

Dose Modifications

Blood pressure will be monitored at least twice daily while in the hospital. A transient hypotensive response is not a contraindication to further treatment, which usually can be continued without difficulty once the blood pressure has stabilized. Subjects who develop grade 3 or 4 hypotension as defined by CTCAEv4, will skip one daily dose of telmisartan and resume dosing the following day at 80 mg/day. Subjects who experience grade 3 or 4 hypotension on 80 mg/day will again skip one daily dose of telmisartan and resume dosing the following day at 40 mg/day. Subjects who experience grade 3 or 4 hypotension on 40 mg/day, and cannot tolerate re-initiation of 40 mg/day after a one drug hiatus, will be discontinued from study treatment. Whenever a dose reduction has occurred, patients who tolerate the reduced dose for one week will be increased to the next highest dose. If that dose is also tolerated for one week, the dose will again be increased until the original 160 mg/day dose is achieved. If a reescalation results in reappearance of hypotension or other drug-related side effects, the medication will be stopped for one day, and the subject will receive the previous tolerated dose (as detailed above) for the remainder of the trial.

Restricted Medications and Measures

Antihypertensives

Antihypertensives other than telmisartan must be discontinued at least three days prior to transplant. Patients who remain hypertensive after 4 weeks despite the use of telmisartan will have appropriate additional antihypertensive medications (such as hydrochlorothiazide) gradually introduced for the period of the study. If telmisartan and hydrochlorothiazide are insufficient to control hypertension during the study, additional compatible antihypertensive medications may be added.

Agents that Increase the Risk of Renal Failure

Hyperkalemia may occur in patients on telmisartan, particularly in patients with advanced renal impairment, heart failure, on renal replacement therapy, or on potassium supplements, potassium-sparing diuretics, potassium-containing salt substitutes or other drugs that increase potassium levels. Potassium-sparing diuretics such as spironolactone, and angiotensin-converting-enzyme (ACE) inhibitors will be discontinued prior to start of study and will not be permitted in conjunction with telmisartan during the study due to potential interactions leading to renal toxicity. Potassium supplements will also be discontinued, and re-started gradually if need is indicated by electrolyte monitoring. Foods high in potassium will be limited to safe levels during the period of telmisartan administration except as specifically allowed by the physician monitoring the patient's electrolyte status.

In patients who are elderly, volume-depleted (including those on diuretic therapy), or with compromised renal function, co-administration of NSAIDs, including selective COX-2 inhibitors, with telmisartan, may result in deterioration of renal function, including possible acute renal failure. These effects are usually reversible. Caution will be taken when administering NSAIDs to study subjects, and renal functions will be monitored.

Impaired Hepatic Function

As the majority of telmisartan is eliminated by biliary excretion, patients with biliary obstructive disorders or hepatic insufficiency can be expected to have reduced clearance. Hepatic function will be closely monitored as part of the standard of care for HCT patients, and increased LFTs or bilirubin will be carefully followed. Careful consideration should be taken before administering any medications that have known hepatic toxicity, especially in patients who experience hepatic insufficiency pre- or post-HCT (e.g., as a result of grade III or IV GVHD).

Continuation of Telmisartan Following Cessation of Study Dosing

Subjects who are baseline hypertensive and wish to continue on some dose of telmisartan as their primary antihypertensive therapy beyond the study treatment period (Day +98 post-HCT) will be permitted to do so after consultation with their treating physician. The subject will be switched from study supply of telmisartan (Micardis®) to the appropriate commercial telmisartan agent.

Subject Discontinuation

Discontinuation from Study Treatment

Any subject who prematurely discontinues from study treatment should still be followed through Day +180 Post HCT for primary, secondary, and exploratory outcomes. Adverse events (AEs) leading to treatment discontinuation of a subject will be followed until resolution, return to baseline, or until the event is considered chronic.

A subject should be withdrawn from the study treatment if, in the opinion of the investigator, it is medically necessary, or if it is the wish of the subject. However every effort should be made to keep the subject on study treatment, especially in cases where the dose or schedule of study treatment can be modified. Subjects who discontinue from study treatment should still complete end of treatment study procedures. Subjects may be discontinued from study treatment for any of the following reasons: 1) ≥grade 3 hypotension at the 40 mg/day dose level after one attempt at restarting this dose following a 1 day drug hiatus; 2) onset or persistence of any treatment related adverse events (AEs) that, in the opinion of the study physician, warrant discontinuation; 3) non-compliance, defined as five missed doses over any 2 weeks period, for reasons other than hypotension or other side effects, within 28 days post-HCT; 4) significant protocol deviation that would render the subject unevaluable; 5) voluntary withdrawal of consent; or 6) pregnancy or plan to become pregnant.

Replacement of Subjects

The study will enroll a total of 60 evaluable subject defined as subjects who remain on telmisartan treatment through Day +28 post-HCT. Patients who discontinue telmisartan before day +28 post-HCT will be replaced by an additional subjects until a total of 60 evaluable subjects is reached. Those who discontinue telmisartan after day +28 post-HCT will not be replaced and will be continued to be followed through the 180 day study period. Subjects who discontinue telmisartan at any time will continue all other study assessments and time points.

Study Evaluations and Assessments

The study design is outlined below in Table 5 Schedule of Events. HCT patients are typically discharged prior to the first weekly visit after Day +7. If a subject remains hospitalized post-HCT for any visit after Day +7, all attempts should be made to complete study required assessments at the appropriate timepoints. Discharge procedure to be performed when appropriate. Day +98 only indicates end of treatment and does not constitute a study visit. No additional assessments are required on Day +98 unless the Day +100 visit occurs 2 days early, as permitted.

TABLE 5

Schedule of Events

| Study Day (relative to HCT) | Screening Day −30 to Day −3 | Treatment Period | | | | | | | | | | | Follow-Up Period | |
|---|---|---|---|---|---|---|---|---|---|---|---|---|---|---|
| | | Inpatient | | | | Inpatient or Outpatient[1] | | | | | | | | |
| | | Day −2 | Day −1 | Day 0 (HCT) | Day +7 | At Discharge | Weekly[2] | Day +28[2] | Weekly[2] | Day +56[2] | Day +70[2] | Day +84[2] | Day +98 | Day +100[2] | Day +180[3] |
| Informed Consent | X | | | | | | | | | | | | | | |
| Confirm Eligibility | X | | | | | | | | | | | | | | |
| Demographics | X | | | | | | | | | | | | | | |
| Complete Medical History | X | | | | | | | | | | | | | | |
| Physical Exam | X | | | Daily During Hospitalization | | | X | X | X | X | X | X | | X | X |
| Height & Weight | X | | | | | | | | | | | | | | |
| Vital Signs (BP, respirations, heart rate, temp) | X | | | | | | | | | | | | | | |
| Blood Pressure Monitoring | | | | Twice/Daily During Hospitalization | | | X | X | X | X | X | X | | X | X |
| Hematology[4] | X | | | Daily During Hospitalization | | | X | X | X | X | X | X | | X | X |
| Serum Chemistries[5] | X | | | | | X | X | X | X | X | X | X | | X | X |
| CD3 Chimerism (serum) | | | | | | | | X | | X | | X | | | |
| CD34 Chimerism (bone marrow) | | | | | | | | | | | | X | | | |
| GVHD Assessment | | | | | | | X | X | X | X | X | X | | X | X |
| Endotoxin Activity Assay | | X[6] | X[6] | X | | | X | X | X | X | | X | | | |
| Blood Samples for Exploratory Studies | | X | X | X | | | X | X | X | X | X | X | | X | X |
| Stool Samples for Exploratory Studies[7] | | X | X | X | | | X | X | X | X | X | X | | X | X |
| Urine Samples for Exploratory Studies[7] | | X | X | X | | | X | X | X | X | X | X | | X | X |
| HCT | | | | X | | | | | | | | | | | |

TABLE 5-continued

Schedule of Events

| | Screening | Treatment Period | | | | | | | | | | | Follow-Up Period | |
|---|---|---|---|---|---|---|---|---|---|---|---|---|---|---|
| Study Day | Day −30 | Inpatient | | | | Inpatient or Outpatient[1] | | | | | | | | |
| (relative to HCT) | to Day −3 | Day −2 | Day −1 | Day 0 (HCT) | Day +7 | At Discharge | Weekly[2] | Day +28[2] | Weekly[2] | Day +56[2] | Day +70[2] | Day +84[2] | Day +98 | Day +100[2] | Day +180[3] |
| Dispense Study Drug | | | | | | X | | X | | X | | X | | | |
| Administer Study Drug | | | | | | Daily from Day −2 to Day +98 | | | | | | | | | |
| Provide Subject Diary | | | | | | X | | | | | | | | | |
| Review Treatment Compliance | | | | | | | X | X | X | X | X | X | X | | |
| Review Concomitant Medications | X | | | | | | | Continuous | | | | | | | |
| Record Adverse Events | | | | | | | | Continuous | | | | | | | |

[1]All post-HCT outpatient visits are approximate and should coincide with the subject's standard post-transpland follow-up visits. If subject is still or re-hospitalized, all attempts should be made to complete study required assessments at the appropriate timepoints
[2]±3 days
[3]±7 days
[4]CBC w. diff and platelets
[5]Chemistry panel with magnesium
[6]Prior to telmisartan administration
[7]If subject is able to provide sample
Please note, all days are in relation to the day(s) following HCT, and not in relation to the initiation of the study drug.

Screening

Prior to commencement of the screening assessments, the patient must have given full informed consent and have signed the study informed consent forms. Once the consent has been signed and dated by the patient, a qualified member of the study team will confirm that subjects meets all eligibility criteria. Screening assessments, including complete medical history, physical exam, height and weight assessment, vital signs (including blood pressure, heart rate, respiratory rate, and temperature), hematology, and serum chemistries must occur within 28 days prior to initiation of study treatment. Most, if not all screening assessments will be part of the patient's routine workup for HCT. Therefore, any study required procedures already performed as part of the subject's routine medical care, even those done before informed consent was signed, may be used to fulfill screening requirements as long as they were performed within the 28 day window.

Telmisartan Dispensing and Administration

Dosing with telmisartan will begin on Day −2 prior to HCT. Prior to hospital discharge, a month supply of study drug will be dispensed and the subject will be instructed how to take study drug at home. The subject will also be given a drug diary to denote when study drug was taken at home. Additional supply of study drug will be dispensed at Day +28, Day +56, and Day +84 visits. The supply of study drug at discharge, Day +28, and Day +56 visits will include enough tablets to last until the subsequent dispensing visit (28 days plus 3 extra days to account for ±3 day variation in timing of visits). If the subject has tablets of study drug remaining at a dispensing visit, they will be instructed to finish their prior bottle of study drug before beginning the next bottle. At the Day +84 visit, just enough study drug will be dispensed to last until Day +98, taking into account any remaining tablets from the Day +56 visit.

The subject will be instructed to bring current supply of study drug and drug diary to each visit.

Safety Evaluations

Physical examinations and CBC with differential and platelets will be performed daily while in the hospital and at all subsequent visits. Chemistry panels plus magnesium will be performed at Day +7 and all subsequent study visits. Blood pressure will assessed twice daily while the subject is hospitalized and at all subsequent visits. Additional assessments may be performed both pre- and post-discharge as per standard medical care for patients undergoing HCT. The results of these assessments will be recorded only if they constitute an adverse event. Serum CD3 chimerism will be assessed at Day +28, Day +56, and Day +84. Bone marrow CD34 chimerism will be assessed at Day +84. GVHD will be assessed both as a safety (grades III and IV) and as an efficacy (grades II-IV) criterion.

Efficacy Assessments

GVHD status will be assessed at all study time points after Day +7 according to 1994 CCAG Grading. Additional GVHD assessments may be performed at clinic visits not required by the study as per standard medical care for patients undergoing HCT. During these visits, positive GVHD findings will be recorded and graded as per study criteria.

Exploratory Studies

Exploratory studies will be carried out, and the results of these analyses will be correlated retrospectively with patients' outcomes. These exploratory studies will not contribute to the management of patients in this study.

Blood

Approximately 2 ml of whole blood will be collected in EDTA anticoagulated tubes for Endotoxin Activity Assay (EAA) at Day −2, Day −1, and Day +7 PRIOR to administration of study drug. Additional samples will be collected at all subsequent study visits prior to Day +56 (excluding day of discharge). The 2 ml blood sample for EAA must be delivered to the research laboratory within 1 hour of being drawn.

Approximately 5 ml of whole blood will be collected in serum collection (red top) tubes for ST2, Reg3a, Elafin, and Ceruloplasmin EIA samples. Another ~30 ml of EDTA anticoagulated blood will be obtained for ROCK substrate phosphorylation, lymphocyte subset proportions, and T regulatory and T effector subsets analysis at all study time points (excluding Day 0 and day of discharge). Samples will be sent to the research labs for processing and batch storage within 2 hours, and preferably at the time of the EAA transport (i.e., within one hour of draw).

Stool and Urine Samples

Stool and clean-catch urine samples for microbiome analysis will be collected at Day −1, Day −2, Day +7 and all subsequent visits until Day +100. Kits for stool and urine collection will be provided to subjects prior to each visit. While all attempts should be made to collect these samples at all required time points, a subject can forego collection at an individual collection if they cannot provide a stool or urine sample due to decreased performance status, malnutrition/dehydration, or other medical reasons.

Methods for Assessing Endpoints

Efficacy Endpoints

Graft vs. Host Disease

Acute GVHD will be scored using the clinical criteria codified at the 1994 CCAG grading, summarized in Table 6. Note that Grade I involves only skin, Grade II can involve liver and bowel, and need not involve skin, Grade III involves skin and liver, and/or gut, and Grade IV involves skin, liver, and gut.

TABLE 6

GVHD Grading and Staging Extent of Organ Involvement

| Stage | Skin | Liver | Gut |
|---|---|---|---|
| 1 | Rash on <25% of skin[a] | Bilirubin 2-3 mg/dl[b] | Diarrhea > 500 ml/day[c] or persistent nausea[d] |
| 2 | Rash on 25-50% of skin | Bilirubin 3-6 mg/dl | Diarrhea > 1000 ml/day |
| 3 | Rash on >50% of skin | Bilirubin 6-15 mg/dl | Diarrhea > 1500 ml/day |
| 4 | Generalized erythroderma with bullous formation | Bilirubin >15 mg/dl | Severe abdominal pain with or without ileus |
| Grade[e] | | | |
| I | Stage 1-2 | None | None |
| II | State 3 or | Stage 1 or | Stage 1 |
| III | — | Stage 2-3 or | Stage 2-4 |
| IV[f] | Stage 4 | Stage 4 | — |

[a]Use "Rule of Nines" or burn chart to determine extent of rash.
[b]Range given as total bilirubin. Downgrade one stage if an additional cause of elevated bilirubin has been documented.
[c]Volume of diarrhea applies to adults. Downgrade one stage if an additional cause of diarrhea has been documented.
[d]Persistent nausea with histological evidence of GVHD in the stomach or duodenum.
[e]Criteria for grading given as minimum degree of organ involvement required to confer that grade.
[f]Grade IV may also include lesser organ involvement with an extreme decrease in performance.

Safety Endpoints

Exams and Laboratory Assessments

Physical exam, vital signs, CBC, and Chemistry panels reflect the standard of care for patients undergoing HCT. Exams and tests will be performed according to standard clinical trial protocol. Any deviations from baseline measurements will be noted and assessed for severity and causality. Hematologic abnormalities determined to be related to the subject's disease or HCT will not be recorded as adverse events.

Non-Relapse Mortality (NRM)

Death due to any cause, in the absence of evidence of recurrent cancer, will be scored as NRM. This would include grade 5 GVHD, which would be noted. Historically <5% NRM in the first month post-transplant has been observed, so early deaths in this study would be concerning.

Engraftment

Appearance and rise in peripheral blood neutrophils will be monitored on a daily basis for the first 2 weeks, and then twice weekly. Absolute neutrophil counts that never reach 500 in the first 28 days and/or platelet counts that drop below 20,000 and remain below that number during the 28 day period will be considered "late engraftment" until repeat evaluation at days 56 and 84 and scored as a primary failure to engraft if no engraftment occurs by those time points. Chimerism analysis of peripheral blood CD3+ cells is routinely assessed at 28, 56, and 84 days after transplantation, and will also be used in the definition of engraftment (5% donor CD3 cells), as described above. These data will be collected for retrospective analysis. Failure to engraft, or loss of engraftment within the first month post-transplant has been rare.

Cancer Relapse/Progression

Depending on the cancer for which HCT is performed, appropriate monitoring for reappearance or progression of tumor will be employed by the transplant teams caring for the patients enrolled into this study. Cancer relapse in the first months post-transplantation has been extremely rare. Most relapse occurs after 6 months post-transplant, which is beyond the formal period of data collection for this trial, although we attempt to follow all transplant patients at our clinic indefinitely.

Exploratory Endpoints

Endotoxin activity assay, ST2, reg3a, elafin, ceruloplasmin are all potential biomarkers for imminent or early GVHD. They will be analyzed retrospectively for correlations with GVHD. Thus, they will not contribute to the management of patients in this study.

Endotoxin Activity (EA) will be monitored by the whole blood EA assay (EAA™) from Spectral Diagnostics (Toronto, Calif.), which has been CE (European Community) and FDA approved for the detection of endotoxin in blood of patients admitted to rule out sepsis (validated and approved for day of admission only). Unlike the other serum proteins being assayed, the EAA will be performed in fresh whole blood in our laboratory, within 2 hours of being drawn.

ST2 will be measured by batch assay of stored serum, using the Presage™ EIA kit from Critical Diagnostics (San Diego, Calif.), that has received CE (European Community) and FDA approval for monitoring cardiac disease. Mueller T, Dieplinger B. Expert Rev Mol Diagn. 13(1): 13-30 (2013). It has very recently been shown to correlate strongly with the imminent onset of GVHD as well, although it is not FDA approved as yet for this indication. Vander Lugt M T, et al. N Engl J Med. 369(6): 529-539 (2013).

Reg3a will be measured by batch assay of stored serum by EIA (AbNova) or Luminex multiplex, depending on relative costs at time of batch assay. Elafin (also called Trappin 2 and Skalp) will be assayed by EIA (R&D) or Luminex multiplex, depending on relative costs at time of batch assay. Ceruloplasmin will be assayed by EIA (Abcam). ROCK substrate phosphorylation (myosin phosphatase myosin binding subunit Threonine 853): The ratios of P-MBS to total MBS in lymphocytes of patients will be recorded.

Lymphocyte subset proportions: The subsets outlined previously will be measured by flow cytometry after staining with appropriate monoclonal Abs. T regulatory and T effector subsets will be enumerated by standard 4-color flow cytometry.

Stool and Urine Microbiomes samples will be processed for amplification of 16S rRNA coding DNA and sequenced by NexGen technology with subsequent analysis of phylogeny proportions based on this sequencing.

Statistical Considerations

Data Management

Data pertaining to the subject's medical history, HCT course and outcome, and clinical follow-up will be abstracted from multiple sources including medical records, and various databases. Any study required data not available from an existing source will be recorded on study specific source document worksheets. All data will be entered into a study specific, password-protected database accessible only by qualified members of the research team. Periodic audits of study data will be performed in conjunction with standard corporate compliance protocols. Coded data from exploratory studies will be recorded in laboratory notebooks prior to inclusion in the study database.

All subjects will be assigned a study specific identification number (ID#). All study data will be recorded using the subject's ID#. A key linking ID#'s with subject identities, accessible only by qualified members of the research team, will be kept separate from study data.

Sample Size

Enrollment of 60 subjects for this pilot study is based on the available patient population undergoing allogeneic HCT, expected rates of enrollment, and the historical data set from the past 3 years' allogeneic HCT experience, as well as the published literature from many centers performing allogeneic HCT for the same underlying diseases, and using similar preparative regimens.

Statistical Analysis Plan

The statistical calculation used to determine power for sample sizes (Z test of proportions) takes the currently available 3 year trial data as the historical control data set. In reviewing these data, as currently available, it appears that the trial data rates of severe GVHD, NRM, and cancer relapse are considerably lower (i.e. better patient outcomes) than the national averages from published studies. Updated trial data will be used for final determinations of significance as it becomes available at time of study completion. The final and complete trial historical data may show GVHD, NRM, and relapse rates closer to the higher nationally reported rates, which would increase the power of our sample size to detect efficacy. However, for purposes of this proposal, it should be noted that the low rates of negative outcomes for the past 3 years' trial experience set stringent criteria for demonstration of efficacy in reduction of severe acute GVHD, NRM. This is reflected in Table 7, which shows that at day 100, no more than 3 of the 60 subjects can have Grade III-V GVHD (includes grade V GVHD related NRM). This threshold increases to 5 subjects at day 180.

TABLE 7

Number of Patents Required by Two-tailed Z-test for Significantly ($p < 0.05$) increased or decreased primary endpoints at day 100 and day 180 vs. 2011-2013 historic controls (n = 149)

| | | | | |
|---|---|---|---|---|
| Interim safety analysis: | | | | |
| | | | # patients out of 20 affected for statistically significant | |
| Day | Endpoint | 3-Year Historic (%) | increased* | decreased |
| 100 | NRM[a] | (15) | 7 | N/A (because 0/20 gives p > 0.05) |
| | Relapse | (12) | 6 | N/A |
| | III, IV[b] | (9) | 5 | N/A |
| | graft failure[c] | (7) | 5 | N/A |
| Efficacy Analyses: | | | | |
| | | | # patients out of 60 affected for statistically significant | |
| | | | increased | decreased |
| 100 | NRM | | 17 | 3 |
| | Relapse | | 15 | 1 |
| | III, IV | | 12 | 0 |
| | graft failure | | 11 | 0 |
| | | | # patients out of 60 affected for statistically significant | |
| | | | increased | decreased |
| 180 | NRM | (20) | 20 | 5 |
| | Relapse | (18) | 19 | 4 |
| | III, IV | (8) | 11 | 0 |
| | graft failure | (7) | 11 | 0 |

* The indicated number of patients for any single event would trigger termination of the trial.
[a]non-relapse mortality (includes grade V GVHD);
[b]grade III or IV GVHD;
[c]ANC < 500 and/or platelets < 20,000 x 3 consecutive determinations after day 42, and/or <5% donor chimerism on day 84.

For primary endpoint analysis, historic GVHD data are available on 178 allogeneic transplants, of whom 46 (26)% experienced grade III or IV acute GVHD. All other allogeneic transplantees (74%) had grade II GVHD. Based on these data, if 8 or fewer of the total 60 study participants experience grade III-IV acute GVHD during the course of the study, a protective effect for this criterion will have been demonstrated, with a p<0.05, based on a one-way Z test for a decreased proportion.

For sample size and power calculation considerations, if the proportion P=0.26 as the rate of Grade III-IV GVHD in the current standard treatment and a one-sided exact test of the proportion and significance level of 0.05 is used, assuming a 9/60 (15%) rate of Grade III-IV GVHD is achievable with telmisartan treatment will have 58.8% power to detect this effect. Testing for a 12% rate would achieve 82.2% power. Using the recommended level of significance (0.025) for a one-sided test, assuming the grade III-IV GVHD by day 100 is 0.15, would have power of 44.4% of detecting this effect. At the 2.5% level, testing if the rate is less than 0.11, will have 79.0% power of detecting. Testing if the rate of grade III-IV in telmisartan treated transplantees is 0.10, will have 85.8% power of detecting this effect using the 2.5% level of significance.

Thus, with respect to grade II acute GVHD, if 37 or fewer patients of the 60 have grade II or lower acute GVHD, a drug effect at p<0.05 will have been demonstrated using a one-way Z test of proportions.

In summary, with only 26% of patients during the past 3 years exhibiting grade III or IV acute GVHD, no more than 7 cases of grade III or IV acute GVHD (~12%) would have to be seen by the completion of the study in order to conclude that severe acute GVHD had been reduced. Considering that 74% of patients during the past 3 years experienced grade II acute GVHD, a reduction to 60% (36 of 60 patients) is required to achieve significance.

For exploratory endpoint biomarkers other than microbiota 16S rRNA sequences, multivariate modification of cumulative incidence statistics of Fine and Gray will be used to evaluate the univariate and multiple effects of primary markers or secondary markers on endpoints. The cumulative incidence of primary endpoints of Grade III-IV GVHD at any time among all patients in the study will be based on the initial systemic diagnosis and treatment. Cox regression analyses will be used to identify exploratory study parameters as risk factors for Grade III-IV GVHD. Exploratory

TABLE 8

Numeric Results for testing H0: P = P0 versus H1: P < P0 using the PASS13 sample size software Test Statistic: Exact Test

| Power | N | Proportion Given H0 (P0) | Proportion Given H1 (P1) | Target Alpha | Actual Alpha | Beta | Reject H0 If R ≤ This |
|---|---|---|---|---|---|---|---|
| 0.8584 | 60 | 0.2600 | 0.1000 | 0.0250 | 0.0140 | 0.1416 | 8 |
| 0.7899 | 60 | 0.2600 | 0.1100 | 0.0250 | 0.0140 | 0.2101 | 8 |

For incidence of Grade II GVHD, historical data reported a rate of incidence of 74%. At 5% level of significance, a one-sided exact test of whether telmisartan can attain lower levels of 62% (37/60), would achieve 63.2% power of detecting. A lower incidence rate of 60% will be detected with 74.5% power. Using the recommended level of significance (0.025) a one-sided exact test of whether Telmisartan can attain the lower incidence rate of 62% will achieve a power of 52.8% to detect this effect. A one-sided exact test of whether the grade II GVHD incidence rate of 0.50 (30/60) can be attained by Telmisartan will have 97.4% power to detect this effect. A one-sided exact test of whether the incidence rate of 60% is possible with telmisartan will achieve power of 65.1%. A one-sided exact test of whether the grade II GVHD incidence rate of 0.57 can be attained by Telmisartan will have 80.5% power to detect this effect.

assays with a P value ≤0.05 for association with Grade III-IV GVHD in univariate testing will be entered in a multivariate Cox regression model.

Additionally, for each parameter, pairwise comparisons will be made between each pre-transplant and post-transplant time point. Statistical comparisons between GVHD(+) and GVHD(−) groups will be performed using a $\chi^2$ or Fisher's exact test for categorical variables or the non-parametric Mann-Whitney U test for continuous variables. Mean values obtained from ELISA assays performed on pre- and post-transplant samples will be compared with the non-parametric Mann-Whitney U test for continuous variables. Next, the change in each blood factor at a given time relative to before the conditioning regimen was initiated will be compared using a paired t-test in GVHD (+) and GVHD (−) groups.

TABLE 9

Numeric Results for testing H0: P = P0 versus H1: P < P0 using the PASS13 sample size software Test Statistic: Exact Test

| Power | N | Proportion Given H0 (P0) | Proportion Given H1 (P1) | Target Alpha | Actual Alpha | Beta | Reject H0 If R ≤ This |
|---|---|---|---|---|---|---|---|
| 0.9741 | 60 | 0.7400 | 0.5000 | 0.0250 | 0.0242 | 0.0259 | 37 |
| 0.8448 | 60 | 0.7400 | 0.5600 | 0.0250 | 0.0242 | 0.1552 | 37 |
| 0.8047 | 60 | 0.7400 | 0.5700 | 0.0250 | 0.0242 | 0.1953 | 37 |
| 0.7587 | 60 | 0.7400 | 0.5800 | 0.0250 | 0.0242 | 0.2413 | 37 |
| 0.6507 | 60 | 0.7400 | 0.6000 | 0.0250 | 0.0242 | 0.3493 | 37 |
| 0.5904 | 60 | 0.7400 | 0.6100 | 0.0250 | 0.0242 | 0.4096 | 37 |
| 0.5275 | 60 | 0.7400 | 0.6200 | 0.0250 | 0.0242 | 0.4725 | 37 |

For 16S rRNA data, statistical analysis will follow the methods outlined above and detailed in Jenq et al. (Jenq R R, et al. J Exp Med. 209(5): 903-911 (2012)). Briefly, for determining diversity, phylogenetic classification, dissimilarity, microbial chaos and UniFrac PCoA, Operational Taxonomic Unit (OTU)-based microbial diversity will be estimated by calculating the Shannon diversity index (Magurran, A. E. 2004. Measuring Biological Diversity. Blackwell Pub., Malden, Ma. 2004) using MOTHUR open software. Phylogenetic classification will be performed for each sequence, using the Bayesian classifier algorithm described (Wang, Q., G. M. Garrity, J. M. Tiedje, J. R. Cole. 2007. Naive Bayesian classifier for rapid assignment of rRNA sequences into the new bacterial taxonomy. Appl. Environ. Microbiol. 73:5261-5267. doi:10.1128/AEM.00062-07) with bootstrap cutoff at 60%. A phylogenetic tree will be inferred using clearcut on the 16S sequence alignment generated by MOTHUR. Microbial chaos is quantified by mean Bray-Curtis time index, calculated as follows: Bray-Curtis dissimilarity index (Magurran, 2004) between temporally adjacent samples will be quantified using MOTHUR and divided by the length of the time interval (in days) between samples, starting with the samples obtained before the transplant and all samples obtained until end of study. Unweighted UniFrac on the resulting tree (Lozupone, C., M. Hamady, R. Knight. 2006. UniFrac—an online tool for comparing microbial community diversity in a phylogenetic context. BMC Bioinformatics. 7:371. doi: 10.1186/1471-2105-7-371) will be analyzed by Principal Coordinates Aanalysis performed on the resulting matrix of distances between each pair of samples.

For statistical comparisons, Shannon diversity index for intervals will be compared using unpaired two-sided Student's t tests with a more stringent cut-off of 0.0125 given multiple comparisons, by the Bonferroni correction for multiple time periods of independent comparisons. Comparisons of bacterial populations will use paired two-sided Wilcoxon matched pairs test for individual patients. Other comparisons will employ two-sided Mann-Whitney tests. Given the final sample size (dependent on patient compliance with request for samples) rigorous statistical inference may be limited by confounding factors that can affect microbiome readouts in addition to GVHD. These include the exact combination and dosage of antibiotics, the underlying disease, patient nutrition, diarrhea, etc. This assessment will be made post hoc. To avoid over-interpretation of data, the analysis will be limited to data description and visualization.

Interim Safety Analysis
Safety Monitoring

Stopping rules based on the three year historical data for 5 criteria:
(i) non-relapse mortality (NRM), (ii) Relapse, (iii) Graft Failure or (iv) Delay, Drug Intolerance, and (v) Grade III-IV GVHD have been generated. These rules and the operating characteristics for the algorithms are presented below.

Stopping Rules

The stopping rules for each of the adverse events (non-relapse mortality (NRM), relapse, graft failure, intolerance to Telmisartan and Grade III or IV GVHD) by day 100 are described. Each of the 5 toxicities is monitored at 1% Type I error (i.e., the probability of stopping by chance the trial when in fact the toxicity rate observed in historical data is true). Thus, the repeated significance test maintains the level of the toxicity through all the monitoring points to be 1%. Jointly, all 5 toxicities have $(1-(1-0.01)^5)=0.049$ probability of stopping the trial by chance when the null hypotheses are true.

Non-Relapse Mortality (NRM) at 100 Days

If the non-relapse mortality (NRM) rate in patients receiving Telmisartan exceeds 22%, then the study will be stopped. The operating characteristics of the stopping rule are described below. Based on historical data from the cancer center registry, 15% incidence of NRM is considered expected and incidence greater than 22% is considered unacceptable.

Using repeated significance testing (Jennison and Turnbull) with 15.0% as lower proportion and 22.0% as higher proportion, 1% alpha level, and 80% power for early termination, shape parameter of the boundary, delta=0.2, with priority on alternative hypothesis and continuous monitoring, the following stopping guidelines were computed by the toxbdry function in the Clinfun package in R 3.2.0 (Table 10).

TABLE 10

Stopping Boundaries for NRM at 100 days using continuous monitoring

| Monitoring Look | Number of Patients at Monitoring Look | Stop if Number of Toxicities is at least |
|---|---|---|
| 1 | 2 | 2 |
| 2 | 7 | 3 |
| 3 | 12 | 4 |
| 4 | 18 | 5 |
| 5 | 24 | 6 |
| 6 | 29 | 7 |
| 7 | 35 | 8 |
| 8 | 41 | 9 |
| 9 | 47 | 10 |
| 10 | 54 | 11 |
| 11 | 60 | 12 |

The trial will be terminated if 2 patients out of the first 2 patients receiving experimental drug (i.e., Telmisartan) experience NRM by day 100. If out of the first 7 patients, 3 or more have NRM by day 100 then trial will be stopped. The boundaries were obtained such that the Type I error, fixed at 1%, was spent over the multiple looks, hence the probability of stopping the trial prematurely by chance is 0.01.

TABLE 11

Operating characteristics for the stopping boundaries for NRM Day 100

| Probability Of Toxicity | Probability of crossing low bndry | Probability of stopping low bndry | Expected sample size low bndry | Probability of crossing high bndry | Probability of stopping high bndry | Expected sample size high bdnry |
|---|---|---|---|---|---|---|
| 0.15 | 0.343 | 0.338 | 47.4 | 0.340 | 0.335 | 47.5 |
| 0.164 | 0.443 | 0.436 | 44.0 | 0.440 | 0.433 | 44.0 |

TABLE 11-continued

Operating characteristics for the stopping boundaries for NRM Day 100

| Probability Of Toxicity | Probability of crossing low bndry | Probability of stopping low bndry | Expected sample size low bndry | Probability of crossing high bndry | Probability of stopping high bndry | Expected sample size high bdnry |
|---|---|---|---|---|---|---|
| 0.178 | 0.544 | 0.536 | 40.4 | 0.541 | 0.533 | 40.4 |
| 0.192 | 0.640 | 0.631 | 36.7 | 0.638 | 0.629 | 36.7 |
| 0.206 | 0.727 | 0.718 | 33.1 | 0.725 | 0.715 | 33.1 |
| 0.220 | 0.800 | 0.792 | 29.7 | 0.798 | 0.790 | 29.7 |

Bndry = boundary

Based on the operating characteristics, the probability of stopping the trial due to NRM if the level of toxicity is at high level of 22% is 0.79. The expected sample size at termination of the trial is 29.7, if Telmisartan is, in fact, more toxic than standard treatment.

Relapse at Day 100

If the incidence of relapse by day 100 in patients receiving Telmisartan exceeds 19%, then the study will be stopped. The operating characteristics of the stopping rule are described below. Based on historical data from the cancer center registry, 12% incidence of relapse is considered expected and incidence greater than 19% is considered unacceptable.

Using repeated significance testing (Jennison and Turnbull) with 12.0% as lower proportion and 19.0% as higher proportion, 1% alpha level, with priority given to the alternative hypothesis and 80% power to for early termination, shape parameter of the boundary, delta=0.2, for continuous monitoring, the following stopping guidelines were computed by the toxbdry function in the Clinfun package in R 3.2.0 (Table 12).

TABLE 12

Stopping Boundaries for Relapse at Day 100

| Monitoring Look | Number of Patients at Monitoring Look | Stop if Number of Toxicities is at least |
|---|---|---|
| 1 | 3 | 2 |
| 2 | 8 | 3 |
| 3 | 15 | 4 |
| 4 | 22 | 5 |
| 5 | 29 | 6 |
| 6 | 37 | 7 |
| 7 | 44 | 8 |
| 8 | 51 | 9 |
| 9 | 59 | 10 |
| 10 | 60 | 11 |

For this continuous monitoring scheme, the trial will be terminated if 2 or more patients out of the first 3 patients receiving experimental drug (i.e., Telmisartan) experience relapse by day 100. If out of the first 8 patients, 3 or more have relapse by day 100 then trial will be stopped, and so forth. Out of all the 15 patients that receive Telmisartan, if 4 or more patients have relapse by day 100 then the drug will be considered more toxic than standard treatment. The boundaries were obtained such that the Type I error, fixed at 1%, was spent over the multiple looks, hence the probability of stopping the trial prematurely by chance is 0.01.

TABLE 13

Operating characteristics for the stopping boundaries for Relapse by Day 100

| Probability Of Toxicity | Probability of crossing low bndry | Probability of stopping low bndry | Expected sample size low bndry | Probability of crossing high bndry | Probability of stopping high bndry | Expected sample size high bdnry |
|---|---|---|---|---|---|---|
| 0.120 | 0.312 | 0.312 | 48.4 | 0.307 | 0.307 | 48.8 |
| 0.134 | 0.418 | 0.418 | 44.8 | 0.414 | 0.414 | 45.2 |
| 0.148 | 0.527 | 0.527 | 40.8 | 0.523 | 0.523 | 41.3 |
| 0.162 | 0.631 | 0.631 | 36.9 | 0.628 | 0.628 | 37.3 |
| 0.176 | 0.724 | 0.724 | 33.0 | 0.721 | 0.721 | 33.4 |
| 0.19 | 0.801 | 0.801 | 29.4 | 0.799 | 0.799 | 29.8 |

Bndry = boundary

Based on the operating characteristics, the probability of stopping the trial due to grade 3 or 4 GVHD if the level of toxicity is at high level of 36% is 0.79. The expected sample size at termination of the trial is 31.8, if Telmisartan is, in fact, more toxic than standard treatment.

Graft Failure at Day 100 (Including Delayed Engraftment and Failure)

If the incidence of graft failure by day 100 in patients receiving Telmisartan exceeds 7.0% then the study will be stopped. The operating characteristics of the stopping rule are described below. Based on historical data from the cancer center registry, 7.0% incidence of relapse is considered expected and incidence greater than 12.0% is considered unacceptable.

Using repeated significance testing (Jennison and Turnbull) with 7.0% as lower proportion and 12.0% as higher proportion, 1% alpha level, and 80% power to for early termination, shape parameter of the boundary, delta=0.2, giving priority to the alternative hypothesis, and continuous monitoring the following stopping guidelines were computed by the toxbdry function in the Clinfun package in R 3.2.0 (Table 14).

TABLE 14

Stopping Boundaries for Graft Failure at Day 100

| Monitoring Look | Number of Patients at Monitoring Look | Stop if Number of Toxicities is at least |
|---|---|---|
| 1 | 9 | 2 |
| 2 | 21 | 3 |
| 3 | 33 | 4 |
| 4 | 45 | 5 |
| 5 | 58 | 6 |
| 6 | 60 | 7 |

The trial will be terminated if 2 or more patients out of the first 9 patients receiving experimental drug (i.e., Telmisartan) experience graft failure by day 100. If out of the first 21 patients, 3 or more have graft failure by day 100 then trial will be stopped. The boundaries were obtained such the Type I error, fixed at 1%, was spent over the multiple looks, hence the probability of stopping the trial prematurely by chance is 0.01.

TABLE 15

Operating characteristics for the stopping boundaries for Graft Failure Day 100

| Probability Of Toxicity | Probability of crossing low bndry | Probability of stopping low bndry | Expected sample size low bndry | Probability of crossing high bndry | Probability of stopping high bndry | Expected sample size high bdnry |
|---|---|---|---|---|---|---|
| 0.07 | 0.373 | 0.373 | 46.1 | 0.365 | 0.365 | 46.2 |
| 0.08 | 0.477 | 0.477 | 42.4 | 0.467 | 0.466 | 42.5 |
| 0.09 | 0.576 | 0.576 | 38.7 | 0.565 | 0.565 | 38.8 |
| 0.10 | 0.666 | 0.666 | 35.0 | 0.655 | 0.654 | 35.1 |
| 0.11 | 0.744 | 0.744 | 31.6 | 0.734 | 0.733 | 31.7 |
| 0.12 | 0.809 | 0.809 | 28.5 | 0.799 | 0.798 | 28.6 |

Bndry = boundary

Based on the operating characteristics, the probability of stopping the trial due to graft failure if the level of toxicity is at high level of 12% is 0.798. The expected sample size at termination of the trial is 28.6, if Telmisartan is, in fact, more toxic than standard treatment.

Telmisartan Intolerance (Including Angioedema and Grade III or Greater Drug-Related Adverse Events after Dose Adjustments)

5% was used as the acceptable rate of intolerance for drug treatment. Using repeated significance testing (Jennison and Turnbull) with 5.0% as lower proportion and 11.0% as higher proportion, 1% alpha level, and 80% power to for early termination, shape parameter of the boundary, delta=0.2, giving priority to the alternative hypothesis and continuous monitoring, the following stopping guidelines were computed by the toxbdry function in the Clinfun package in R 3.2.0 (Table 16).

TABLE 16

Stopping Boundaries for Intolerance to Telmisartan at Day 100

| Monitoring Look | Number of Patients at Monitoring Look | Stop if Number of Toxicities is at least |
|---|---|---|
| 1 | 8 | 2 |
| 2 | 22 | 3 |
| 3 | 38 | 4 |
| 4 | 55 | 5 |
| 5 | 60 | 6 |

The trial will be terminated if 2 or more patients out of the first 8 patients receiving experimental drug, Telmisartan, experience intolerance by day 100. If out of the first 22 patients, 3 or more have intolerance by day 100 then trial will be stopped. The boundaries were obtained such the Type I error, fixed at 1%, was spent over the multiple looks, hence the probability of stopping the trial prematurely by chance is 0.01.

TABLE 17

Operating characteristics for the stopping boundaries for Intolerance Day 100

| Probability Of Toxicity | Probability of crossing low bndry | Probability of stopping low bndry | Expected sample size low bndry | Probability of crossing high bndry | Probability of stopping high bndry | Expected sample size high bdnry |
|---|---|---|---|---|---|---|
| 0.050 | 0.222 | 0.221 | 52.3 | 0.219 | 0.218 | 52.4 |
| 0.062 | 0.350 | 0.350 | 48.1 | 0.346 | 0.345 | 48.2 |
| 0.074 | 0.483 | 0.483 | 43.5 | 0.480 | 0.477 | 43.6 |
| 0.086 | 0.608 | 0.608 | 38.9 | 0.604 | 0.601 | 39.0 |
| 0.098 | 0.714 | 0.711 | 34.4 | 0.712 | 0.708 | 34.6 |
| 0.11 | 0.800 | 0.797 | 30.4 | 0.798 | 0.794 | 30.6 |

Based on the operating characteristics, the probability of stopping the trial due to intolerance if the level of toxicity is at high level of 11% is 0.794. The expected sample size at termination of the trial is 30.6, if Telmisartan is, in fact, more toxic than standard treatment.

Grade III or Grade IV at 100 Days

If the rate of NRM in Grade 3 or 4 GVHD patients receiving Telmisartan exceeds 36% then the study will be stopped. The operating characteristics of the stopping rule are described below. Based on historical data from the cancer center registry, 26% incidence of NRM is considered expected and incidence greater than 36% is considered unacceptable.

Using repeated significance testing (Jennison and Turnbull) with 26.0% as lower proportion and 36.0% as higher proportion, 1% alpha level, and 80% power for early termination, shape parameter of the boundary, delta=0.2, with priority on alternative hypothesis and continuous monitoring, the following stopping guidelines were computed by the toxbdry function in the Clinfun package in R 3.2.0 (Table 18).

TABLE 18

Stopping Boundaries for NRM at 100 days using continuous monitoring

| Monitoring Look | Number of Patients at Monitoring Look | Stop if Number of Toxicities is at least |
| --- | --- | --- |
| 1 | 3 | 3 |
| 2 | 5 | 4 |
| 3 | 8 | 5 |
| 4 | 11 | 6 |
| 5 | 14 | 7 |
| 6 | 18 | 8 |
| 7 | 21 | 9 |
| 8 | 24 | 10 |
| 9 | 28 | 11 |
| 10 | 31 | 12 |
| 11 | 35 | 13 |
| 12 | 38 | 14 |
| 13 | 42 | 15 |
| 15 | 45 | 16 |
| 16 | 49 | 17 |
| 17 | 52 | 18 |
| 18 | 56 | 19 |
| 19 | 59 | 20 |
| 20 | 60 | 21 |

The trial will be terminated if 3 patients out of the first 3 patients receiving experimental drug, Telmisartan, experience Grade 3 or 4 GVHD by day 100. If out of the first 5 patients, 4 or more have NRM by day 100 then trial will be stopped. The boundaries were obtained such the Type I error, fixed at 1%, was spent over the multiple looks, hence the probability of stopping the trial prematurely by chance is 0.01.

TABLE 19

Operating characteristics for the stopping boundaries for NRM Day 100

| Probability Of Toxicity | Probability of crossing low bndry | Probability of stopping low bndry | Expected sample size low bndry | Probability of crossing high bndry | Probability of stopping high bndry | Expected sample size high bdnry |
| --- | --- | --- | --- | --- | --- | --- |
| 0.26 | 0.253 | 0.247 | 51.5 | 0.247 | 0.247 | 51.5 |
| 0.28 | 0.359 | 0.351 | 48.1 | 0.351 | 0.351 | 48.1 |
| 0.30 | 0.478 | 0.467 | 44.3 | 0.467 | 0.467 | 44.3 |
| 0.32 | 0.597 | 0.695 | 40.2 | 0.585 | 0.585 | 35.2 |
| 0.34 | 0.708 | 0.695 | 35.9 | 0.695 | 0.695 | 35.9 |
| 0.36 | 0.801 | 0.790 | 31.8 | 0.790 | 0.790 | 31.8 |

Bndry = boundary

Based on the operating characteristics, the probability of stopping the trial due to grade 3 or 4 GVHD if the level of toxicity is at high level of 36% is 0.79. The expected sample size at termination of the trial is 31.8, if Telmisartan is, in fact, more toxic than standard treatment.

Safety Monitoring

Adverse Events

For the purposes of this research study, an "adverse event" (AE) is any untoward medical occurrence associated with the use of a study drug, whether or not considered drug related. An AE can be a clinical event in the form of signs, symptoms, disease, or laboratory or physiological observations occurring in a study participant, regardless of causal relationship. A "pre-existing" condition is one that is present prior to study drug administration and is reported as part of the patient's medical history. A pre-existing condition should be reported as an AE only if the frequency, intensity, or character of the pre-existing condition worsens during the course of the study.

Laboratory abnormalities associated with subjects underlying disease or related to the subject's HCT will not be considered adverse events. However, a laboratory abnormality (e.g. a clinically significant change detected on clinical chemistry or hematology) that is independent from the underlying medical condition and/or HCT that requires medical or surgical intervention, or leads to study drug discontinuation, will be considered an AE.

Recording Adverse Events

All AE's will be graded according to CTCAE version 4.03. All grade 3, 4, and 5 nonhematologic adverse events will be recorded. Grade 1 and 2 adverse events will be recorded if they are: 1) potentially associated with GvHD, or 2) potentially attributable to the administration of telmisartan during the period of administration. All AEs should be recorded and, whenever possible, followed until resolution. Documented AEs should contain the following information: 1) severity grade according to CTCAEv4; 2) duration, including start and end dates or if the event is ongoing; 3) relationship to the study treatment (unrelated, possibly related, related); 4) action taken with regard to study treatment; 5) whether other medication or therapies were needed and initiated; 6) outcome (resolved, not resolved, resolved with sequelae, fatal, or unknown); and 7) whether it constitutes a series adverse event (SAE).

Serious Adverse Events

An adverse event or suspected adverse reactions is considered serious if, in the view of the investigator or sponsor, it results in any of the following outcomes: 1) death; 2) life-threatening AE (places the patient at immediate risk of death at the time of the event as it occurred; it does not include an AE that, had it occurred in a more severe form, it might have caused death); 3) persistent or significant incapacity or substantial disruption of the ability to conduct normal life functions; 4) inpatient hospitalization or prolongation of hospitalization; or 5) congenital anomaly or birth defect.

Important medical events that may not result in death, be life threatening, or require hospitalization may be considered an SAE when, based upon appropriate medical judgment, they may jeopardize the patient and may require medical or surgical intervention to prevent one of the outcomes listed in this definition above. All SAEs will be recorded and reported to the IRB and FDA according to institutional and federal policy.

Risks and Benefits Assessment

Potential Benefits

The primary benefit to patients enrolled into this study is a reduction in the incidence or severity of acute GvHD, without a diminution in the desired graft-versus-cancer effect of allogeneic HSC transplantation. A reduction in the incidence or severity of acute GvHD will result in a decrease in the use of corticosteroids used in the management of acute GvHD, and a resulting decrease in complications of corticosteroid use including immunosuppression, opportunistic viral and fungal infections, steroid myopathy, cataract formation, and avascular necrosis of the bone.

Risk/Benefits

Patients undergoing allogeneic hematopoietic stem cell transplantation using myeloablative regimens and cells from related or unrelated donors face considerable risks associated with this treatment. These risks include prolonged periods of marrow hypoplasia requiring blood component and antibiotic support. Even after engraftment, the immunological dysfunction persisting for months after transplantation can lead to opportunistic infections. A small proportion of patients will fail to achieve sustained donor cell engraftment, requiring re-conditioning and a second transplant. The primary causes of treatment failure, however, arise from acute and/or chronic GVHD and from relapse of disease.

In phase III and post-marketing safety studies, telmisartan, 80 or 160 mg per day, was found to have a very good safety profile, with the incidence of reported "poor tolerability" of only 0.5%. Michel M C, et al., Drug Saf. 27(5):335-344 (2004). In theory, due to its anti-inflammatory actions, telmisartan could increase the risks of risks of primary or secondary graft failure, delayed engraftment, early post-transplant relapse of disease. Other serious complications of allogeneic HSC transplantation could occur through unforeseen interactions with other medications or as a result of chemotherapy administration. It is unlikely, but theoretically possible, that successful reduction of acute IT GVHD could redirect allo-reactive T cells to the skin or lungs to produce higher levels of GVHD at those sites.

Informed Consent

Voluntary, written informed consent will be obtained from each subject's parents or legal guardians in accordance with GCP and federal and institutional regulations.

Investigator Responsibilities

The PI will conduct the study according to the current protocol, obtain IRB approval to conduct the study, will obtain informed consent from each study participant, will maintain and supply auditors and regulatory agencies adequate and accurate records of study activity, will report serious adverse events to the IRB, will personally conduct or supervise the study, and will ensure that colleagues participating in the study are informed about their obligations in meeting the above commitments.

Institutional Review Board Approval

The PI will submit this protocol, the consent form, any other relevant supporting information to the IRB for review and approval before study initiation.

Confidentiality

All samples and study data will be coded with each subject's ID#. The list linking subject ID# to subject identity will be accessible only to authorized members of the study team.

After careful consideration, the PI and sub-investigators have determined that all of the above criteria have been met for this study.

Study Termination

The PI reserves the right to terminate the study at any time. Conditions that may warrant termination of the study include, but are not limited to: 1) Unsatisfactory enrollment; 2) Serious and/or persistent non-compliance with the protocol and/or applicable regulatory guidelines in conducting the study; 3) IRB or DSMB decision to terminate or suspend approval; 4) Investigator fraud (altered data, omitted data, or manufactured data); 5) The incidence/severity of AEs indicates a potential health hazard to patients; and 6) Discovery of an unexpected, serious, or unacceptable risk to subjects.

SUMMARY

While the invention has been described with reference to the specific embodiments thereof, it should be understood by those skilled in the art that various changes may be made and equivalents may be substituted without departing from the true spirit and scope of the invention. In addition, many modifications may be made to adapt to a particular situation, material, composition of matter, process, process step or steps, to the objective, spirit and scope of the described invention. All such modifications are intended to be within the scope of the claims appended hereto.

What is claimed is:

1. A method for treating a patient with a tumor receiving a transplant comprising administering to the patient a therapeutic amount of a pharmaceutical composition consisting essentially of:
   (i) a Rho kinase inhibitor compound, wherein the Rho kinase inhibitor compound is telmisartan; and
   (ii) a pharmaceutically acceptable carrier,
   wherein the therapeutic amount is effective
   to attenuate an immunological complication associated with high dose cancer treatment followed by allogeneic bone marrow and stem cell transplantation caused by mature donor lymphocyte alloreactivity to host tissue antigens [graft-versus-host disease (GVHD)],
   to preserve a graft-versus-tumor effect (GVTE) characterized by an immune response to a graft recipient's tumor cells by a donor's transplanted immune cells in the bone marrow or peripheral blood of the recipient, relative to a control receiving a transplant with donor T cells but not receiving the Rho kinase inhibitor compound in (i); and
   to reduce rates of severe GVHD, non-relapse mortality (NRM), and cancer relapse.

2. The method according to claim 1, wherein the GVHD is acute.

3. The method according to claim 1, wherein the GVHD is chronic.

4. The method according to claim 1, wherein the transplant is allogeneic.

5. The method according to claim 1, wherein the transplant is xenogeneic.

6. The method according to claim 1, wherein the transplant is a bone marrow transplant.

7. The method according to claim 1, wherein the transplant is a vascularized composite allotransplant (VCA).

8. The method according to claim 1, wherein the pharmaceutical composition of claim 1 further comprises a Rho Associated Coiled-Coil Kinase (ROCK) inhibitor.

9. The method according to claim 1, wherein the pharmaceutical composition of claim 1 further comprises an angiotensin receptor blocker (ARB).

10. The method according to claim 1, wherein the pharmaceutical composition of claim 1 further comprises a peroxisome proliferator activated receptor gamma (PPARy) agonist.

11. The method according to claim 1, wherein the administering to the patient is orally.

12. The method according to claim 1, wherein the administering to the patient is parenterally.

13. The method according to claim 1, wherein the therapeutic amount of the pharmaceutical composition is effective:
(a) to increase patient survival;
(b) to preserve alloreactivity;
(c) to increase ratio of Treg:alloreactive Teffectors;
(d) to reduce tumor burden,
(e) to reduce tumor growth,
(f) to reduce tumor progression,
(g) to reduce tumor proliferation,
(h) to increase survival; or
(i) a combination thereof.

14. The method according to claim 1, wherein the tumor is a nonhematologic solid tumor.

15. The method according to claim 14, wherein the tumor is selected from the following group consisting of an adenoma, a blastoma, a carcinoma, a lymphoma, a melanoma, and a sarcoma.

16. The method according to claim 1, wherein the therapeutic amount of the pharmaceutical composition is effective to improve weight recovery following GVHD-related weight loss.

17. A method for predicting, monitoring, and reducing progression of an immunological complication associated with high dose cancer treatment followed by allogeneic bone marrow and stem cell transplantation caused by mature donor lymphocyte alloreactivity to host tissue antigens [graft versus host disease (GVHD)], in a patient with a tumor receiving a transplant comprising:
(i) obtaining pre-transplant and post-transplant liquid samples from the patient;
(ii) detecting from the pre-transplant and post-transplant liquid samples a Rho Associated Coiled-Coil Kinase (ROCK) activity, and quantifying a change of ROCK activity in the pre-transplant and post-transplant liquid samples;
(iii) predicting and correlating a degree of GVHD progression in the patient based on an increased level of a biomarker selected from the group consisting of elafin, IL-8, TNFR1, HGF, reg3a, IL-2RA, ST2, and Lipid A endotoxin in the post-transplant liquid sample compared to a level of the biomarker in the pre-transplant liquid sample; and
(iv) treating the patient with a therapeutically effective treatment regimen to reduce the GVHD progression comprising a therapeutic amount of a Rho kinase inhibitor compound while preserving a graft-versus-tumor effect (GVTE) characterized by an immune response to a graft recipient's tumor cells by a donor's transplanted immune cells in the bone marrow or peripheral blood of the recipient, wherein the Rho kinase inhibitor compound is telmisartan.

18. The method according to claim 17, wherein the liquid samples are selected from the group consisting of serum, plasma, and whole blood.

19. The method according to claim 17, wherein the therapeutically effective regimen to reduce the GVHD progression comprises administering a pharmaceutical composition comprising a therapeutic amount of a the Rho kinase inhibitor compound, wherein the therapeutically effective amount is effective: (a) to increase patient survival; (b) to preserve alloreactivity; (c) to increase the ratio of Treg:alloreactive Teffectors; (d) to reduce tumor burden, (e) reduce tumor growth, (f) reduce tumor progression, (g) reduce tumor proliferation, (h) increase survival, or (i) a combination thereof.

* * * * *